United States Patent
Lim et al.

(10) Patent No.: US 11,590,076 B2
(45) Date of Patent: Feb. 28, 2023

(54) CRYOGEL SCAFFOLD CAPABLE OF CONTROLLING DEGREE OF DEGRADATION AND SOFT BIO-INTEGRATED DEVICE IN WHICH DRUG MODULATING IMMUNOSUPPRESSIVE ACTION IN SOLID MICROENVIRONMENT IS LOADED IN SAME SCAFFOLD

(71) Applicant: Research & Business Foundation Sungkyunkwan University, Suwon-si (KR)

(72) Inventors: Yong Taik Lim, Seongnam-si (KR); Chanyoung Song, Suwon-si (KR); Phuengkham Hathaichanok, Suwon-si (KR); Long Ren, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 268 days.

(21) Appl. No.: 16/954,324

(22) PCT Filed: Dec. 14, 2018

(86) PCT No.: PCT/KR2018/015921
§ 371 (c)(1),
(2) Date: Jun. 16, 2020

(87) PCT Pub. No.: WO2019/124886
PCT Pub. Date: Jun. 27, 2019

(65) Prior Publication Data
US 2021/0161814 A1   Jun. 3, 2021

(30) Foreign Application Priority Data

Dec. 18, 2017 (KR) .................. 10-2017-0173848
Nov. 19, 2018 (KR) .................. 10-2018-0143015

(51) Int. Cl.
*A61K 9/06*     (2006.01)
*A61K 31/337*   (2006.01)
(Continued)

(52) U.S. Cl.
CPC .............. *A61K 9/06* (2013.01); *A61K 31/337* (2013.01); *A61K 31/4745* (2013.01);
(Continued)

(58) Field of Classification Search
None
See application file for complete search history.

(56) References Cited

U.S. PATENT DOCUMENTS

2014/0227327 A1* 8/2014 Bencherif ...... A61K 39/001106
424/277.1
2017/0216288 A1   8/2017 Nishikawa et al.

FOREIGN PATENT DOCUMENTS

KR   10-2013-0124798 A   11/2013

OTHER PUBLICATIONS

Chen et al. (Dual Function of Glucosamine in Gelatin/Hyaluronic acid cryogel to modulate scaffold mechanical properties and to maintain chondrogenic phenotypes for cartilage tissue engineering, International Journal of Molecular Sciences, 2016, vol. 17, No. 11, pp. 1-22). (Year: 2016).*

(Continued)

*Primary Examiner* — Melissa S Mercier
(74) *Attorney, Agent, or Firm* — NSIP Law

(57) ABSTRACT

The present invention relates to a cryogel scaffold capable of controlling the degree of degradation and a soft bio-integrated device in which a drug modulating an immunosuppressive action in solid tumor microenvironment is loaded in the scaffold.

9 Claims, 49 Drawing Sheets

(51) Int. Cl.
*A61K 31/4745* (2006.01)
*A61K 31/704* (2006.01)
*A61K 31/7068* (2006.01)
*A61K 47/32* (2006.01)
*A61K 47/34* (2017.01)
*A61K 47/36* (2006.01)
*A61K 47/42* (2017.01)
*A61K 47/46* (2006.01)
*C07K 16/28* (2006.01)

(52) U.S. Cl.
CPC ........ *A61K 31/704* (2013.01); *A61K 31/7068* (2013.01); *A61K 47/32* (2013.01); *A61K 47/34* (2013.01); *A61K 47/36* (2013.01); *A61K 47/42* (2013.01); *A61K 47/46* (2013.01); *C07K 16/2818* (2013.01); *C07K 16/2878* (2013.01)

(56) References Cited

OTHER PUBLICATIONS

Chien et al. (Glucosamine Modulates T cell Differentiation through Down Regulating N-Linked Glycosylation of CD 25, J Biol Chem Dec. 4, 2015; 290(49): 29329-29344). (Year: 2015).*
International Search Report dated Jun. 4, 2019 in corresponding International Patent Application No. PCT/KR2018/015921 (2 pages in English, 2 pages in Korean).
Chen et al., "Dual Function of Glucosamine in Gelatin/Hyaluronic Acid Cryogel to Modulate Scaffold Mechanical Properties and to Maintain Chondrogenic Phenotype for Cartilage Tissue Engineering," International Journal of Molecular Sciences, 2016, vol. 17(11), pp. 1-22.
Cho et al., "Photothermal-modulated drug delivery and magnetic relaxation based on collagen/poly(γ-glutamic acid) hydrogel," International Journal of Nanomedicine, Mar. 31, 2017, vol. 12, pp. 2607-2620.

* cited by examiner unmodified hyaluronic acid $R_1$ modified HA by carboxyl conjugation $R_2$ modified HA by hydroxyl conjugation

CRYOGEL SCAFFOLD CAPABLE OF CONTROLLING DEGREE OF DEGRADATION AND SOFT BIO-INTEGRATED DEVICE IN WHICH DRUG MODULATING IMMUNOSUPPRESSIVE ACTION IN SOLID MICROENVIRONMENT IS LOADED IN SAME SCAFFOLD

CROSS REFERENCE TO RELATED APPLICATION(S)

This application is a U.S. National Stage Application of International Application No. PCT/KR2018/015921, filed on Dec. 14, 2018, which claims the benefit under 35 USC 119(a) and 365(b) of Korean Patent Application No. 10-2017-0173848, filed Dec. 18, 2017, and Korean Patent Application No. 10-2018-0143015, filed Nov. 19, 2018, in the Korean Intellectual Property Office, the entire disclosure of which is incorporated herein by reference for all purposes.

TECHNICAL FIELD

The present invention relates to a cryogel scaffold capable of controlling degradability, and a soft bio-integrated device in which a drug for controlling an immunosuppressive action in a solid tumor microenvironment is loaded into the scaffold.

BACKGROUND ART

A porous scaffold fabricated using a biomaterial and a synthetic polymer is used in various fields. Particularly, the porous scaffold has been used as scaffolds for cell growth and tissue engineering in the biomedical field, a cell delivery system and a drug delivery system, and for purification of a biomaterial. Such a porous scaffold has been fabricated using the main ingredient of an extracellular matrix (ECM) such as alginate, gelatin, collagen or hyaluronic acid by a physical/chemical crosslinking method. Conventionally, to form a pore in the porous scaffold, a method of using a special template or porogen material has been actively used, but all of porous scaffolds fabricated by the above method have uniform degradability or have the shortcoming of having a very low swelling ratio. However, since the degradability or swelling ratios of porous scaffolds used in biological and medical fields have to be freely adjusted according to their use and purpose, recently, there have been attempts to use a low molecular weight constituent material to adjust degradability or to lower a crosslinking density. But, in this case, the porous scaffolds had the shortcoming of lowering mechanical properties. Therefore, the porous scaffolds that can control degradability and maintain mechanical properties and swelling ratios are expected to be effectively used in biological and medical fields.

Meanwhile, an anti-cancer immunotherapy method for treating cancer using the body's immune system has an advantage of minimizing side effects compared with conventional chemotherapy or radiotherapy. Among these anti-cancer immunotherapeutic methods, a cell therapeutic method of directly injecting therapeutic immune cells such as dendritic cells, natural killer cells or T cells into the body after in vitro activation has been actively studied. In addition, research on a cancer vaccine increasing an anticancer effect by activating therapeutic immune cells in the body by injecting a cancer antigen and an immune-activating material into the body is being actively conducted. However, such a cell therapeutic agent or cancer vaccine is mainly used for blood cancer-associated diseases, and has the shortcoming of having a very low therapeutic effect on most solid tumors. One of the reasons of the low therapeutic effect on solid tumors is a microenvironment that inhibits an immune function near a solid tumor. Actually, cells degrading the function of immune cells (myeloid-derived stromal cells (MDSCs), regulatory T cells (Treg) and tumor-associated macrophages (TAM)), immunosuppression-inducing cytokines or metabolites actively function in a tumor microenvironment, thereby rapidly reducing the activities of an immune-activating material and therapeutic immune cells.

In addition, dendritic cells, NK cells and T cells, which are therapeutic immune cells currently tried in clinical trials, are injected into the body intraperitoneally or through blood vessel injection. Here, a large number of the injected cells remains near the injection site, or the cells do not properly function and die in in vivo circulation. Therefore, in the actual clinical field, attempts to increase a cancer therapeutic effect are progressing by in vivo injection of a large amount, for example, 10(9) or more, of therapeutic immune cells. However, a lot of time and costs are needed to in vitro culture a large number of cells, and treatment costs are also very high. In addition, a large number of cells cultured in vitro should be used in patients within a specific period, otherwise, there is a fatal disadvantage in that the large number of therapeutic cells prepared at high cost must be disposed of.

Drugs targeting cells, cytokines or metabolites involved in an immunosuppressive action in the solid tumor microenvironment have been developed, and thus a test for the efficacy thereof is actively progressing in the clinical field. However, most of the drugs have very low stability, and when a high dose of a drug is injected into the body through intravenous injection, toxicity and side effects that can kill even immune cells responsible for an anti-cancer treatment function as well as normal cells are becoming the biggest problems.

Therefore, to increase the therapeutic effect against a solid tumor, there is a very urgent need to develop a novel therapeutic platform technique that can control an immunosuppressive factor in the solid tumor microenvironment, activate therapeutic immune cells and maintain the function of the cells. However, until now, there is no invention relating to a bio-integrated device that can control an immunosuppressive factor in the solid tumor microenvironment and maintain the activation of therapeutic immune cells at the same time.

Recently, the Mooney group at Harvard University (USA) developed a novel type of cancer vaccine, which includes GM-CSF, CpG and a cancer cell lysate in a porous scaffold fabricated using a PLGA polymer, and there is a case of applying the cancer vaccine in the cancer treatment field (U.S. Pat. No. 6,748,954 B2). In this research, to fabricate a porous scaffold, a gas-foaming process was used. In addition, the Stephan group at the Fred Hutchison Cancer Research Center (USA) simultaneously loaded therapeutic T cells and an activator into an alginate matrix to be used as cancer therapy technology. However, in the prior research, a scaffold in which a dendritic cell-activating vaccine component and therapeutic T cells are loaded was fabricated, but no immunosuppressive factor under the solid tumor microenvironment was considered. Therefore, it is urgent to develop a bio-integrated flexible device that can induce local delivery of various customized immunosuppressive factors in the solid tumor microenvironment.

Technical Problem

Disclosure

To solve the problems of the prior art described above, the present invention is directed to providing a cryogel scaffold fabricated by crosslinking at a low temperature (−4° C. or −20° C.), which can form an interconnected pore structure without using an intermediate material (template or porogen), based on various biomolecules rather than alginate actively used today, a customized soft bio-integrated device in which various drugs that can control various immunosuppressive factors degrading the efficacy of an anticancer immunotherapeutic agent in a solid tumor microenvironment are loaded, and a method of fabricating the same.

In further detail, the present invention is directed to providing a cryogel scaffold which includes a structure formed by crosslinking a first component swollen when brought into contact with an aqueous solution and thus increased in volume and a second component which is different from the first component, is crosslinkable with the first component at a low temperature and enables the control of degradability by an external stimulus after being crosslinked with the first component, and a method of fabricating the same.

In addition, the present invention is directed to providing a soft bio-integrated device, which includes a cryogel scaffold, which includes a structure formed by crosslinking a first component swollen when brought into contact with an aqueous solution and thus increased in volume and a second component enabling the control of degradability by an external stimulus after being crosslinked with the first component at a low temperature; and a drug controlling an immunosuppressive action in a solid tumor microenvironment, and a method of fabricating the same.

However, technical problems to be solved in the present invention are not limited to the above-described problems, and other problems which are not described herein will be fully understood by those of ordinary skill in the art from the following descriptions.

TECHNICAL SOLUTION

To attain the purpose of the present invention, the present invention provides a cryogel scaffold, which includes a structure formed by crosslinking a first component and a second component. The cryogel scaffold is increased in volume due to swelling when the first component is brought into contact with an aqueous solution, and can control degradability by an external stimulus after crosslinking between the first component and the second component, which is different from the first component.

In one embodiment of the present invention, the first component may include one or more components selected from the group consisting of hyaluronic acid, hyaluronic acid-methacrylate, poly(glutamic acid), poly(gamma-glutamic acid), poly(amino acid) and derivatives thereof.

In another embodiment of the present invention, the second component may include one or more components selected from the group consisting of collagen, hyaluronic acid, hyaluronic acid-aldehyde methacrylate, poly(gamma-glutamic acid), poly(amino acid), chitosan, cellulose, polyacrylate, polyacrylic acid and derivatives thereof.

In still another embodiment of the present invention, the first component may be hyaluronic acid-methacrylate (HA-MA), and the second component may be hyaluronic acid-aldehyde methacrylate (HA-ald-MA).

In yet another embodiment of the present invention, the second component may be collagen, and the first component may be poly(gamma-glutamic acid) or hyaluronic acid.

In yet another embodiment of the present invention, the first component and the second component may be included at 10:90 to 90:10, 20:80 to 80:20, 30:70 to 70:30, 40:60 to 60:40, or 50:50 w/v %.

In yet another embodiment of the present invention, the crosslinked structure of the first component and the second component may be formed at −25 to −4° C.

In yet another embodiment of the present invention, a pore diameter of the cryogel scaffold may be 20 to 900 μm.

In yet another embodiment of the present invention, the pore diameter may be adjusted by a two-step cooling technique.

In yet another embodiment of the present invention, the external stimulus may be one or more stimuli selected from a physiological condition in the body, light, a reductant and an enzyme.

In addition, the present invention provides a method of fabricating a cryogel scaffold, which includes: (a) preparing a first component solution containing a first component; (b) preparing a second component solution containing a second component; (c) preparing a mixed solution by mixing the first component solution and the second component solution; and (d) crosslinking the mixed solution at a low temperature, wherein the first component is swollen when brought into contact with an aqueous solution, thereby increasing the volume of the scaffold, and the second component, which is a compound different from the first component, is crosslinkable with the first component and enables the control of degradability by an external stimulus after being crosslinked with the first component.

In one embodiment of the present invention, the first component in step (a) may include one or more components selected from the group consisting of hyaluronic acid, hyaluronic acid-methacrylate, poly(glutamic acid), poly(gamma-glutamic acid), poly(amino acid) and derivatives thereof.

In another embodiment of the present invention, the second component in step (b) may include one or more components selected from the group consisting of collagen, hyaluronic acid, hyaluronic acid-aldehyde methacrylate, poly(gamma-glutamic acid), poly(amino acid), chitosan, cellulose, polyacrylate, polyacrylic acid and derivatives thereof.

In still another embodiment of the present invention, the first component in step (a) may be hyaluronic acid-methacrylate (HA-MA), and the second component in step (b) may be hyaluronic acid-aldehyde methacrylate (HA-ald-MA).

In yet another embodiment of the present invention, the second component in step (b) may be collagen, and the first component in step (a) may be poly(gamma-glutamic acid) or hyaluronic acid.

In yet another embodiment of the present invention, the first component or the second component in step (a) or (b) may be included in each solution at a concentration of 0.1 to 50 mg/mL.

In yet another embodiment of the present invention, crosslinking in step (d) may be performed for 3 to 24 hours at −25 to −4° C.

In yet another embodiment of the present invention, in step (d), the mixed solution may be poured into a mold and then crosslinked at a low temperature.

In addition, the present invention provides a soft bio-integrated device, which includes the cryogel scaffold and a drug for controlling an immunosuppressive action in the solid tumor microenvironment.

In one embodiment of the present invention, the drug that controls an immunosuppressive action in a solid tumor microenvironment may suppress the activity, survival or proliferation of myeloid-derived suppressor cells (MDSCs), regulatory T cells (Tregs), and/or tumor-associated macrophages (TAMs).

In another embodiment of the present invention, the drug for controlling an immunosuppressive action in a solid tumor microenvironment may serve to suppress an immunosuppressive environmental factor in the solid tumor microenvironment, or to suppress an immune checkpoint by activating T cells through direct binding in the solid tumor microenvironment.

In still another embodiment of the present invention, the soft bio-integrated device may further include one or more drugs selected from the group consisting of an anticancer agent for suppressing tumor growth, a immunosuppressive factor-controlling drug, a cancer vaccine, an immunoadjuvant, immune cells for cancer therapy, and a cytokine required for maintaining the activity of the immune cells for cancer therapy.

In yet another embodiment of the present invention, the drug suppressing the growth of a tumor may include one or more selected from the group consisting of a DNA methyltransferase inhibitor (DNMTi), a histone deacetylase inhibitor (HDACi), and an angiogenesis inhibitor.

In yet another embodiment of the present invention, the drug may be loaded in the cryogel scaffold, and the loading of the drug may be pre-fabrication loading or post-fabrication loading.

In yet another embodiment of the present invention, the pre-fabrication loading may be performed by crosslinking after the drug is mixed in a mixed solution of a first component and a second component before the structure of the cryogel scaffold is formed.

In yet another embodiment of the present invention, the post-fabrication loading may be performed by a method of immersing the cryogel scaffold in a drug, a method of dropping a drug on the cryogel scaffold, or a method of directly injecting a drug into the cryogel scaffold.

In addition, the present invention provides a method of fabricating a soft bio-integrated device, which includes: (a) preparing a first component solution containing a first component; (b) preparing a second component solution containing a second component; (c) preparing a mixed solution by mixing the first component solution, the second component solution and a drug; and (d) crosslinking the mixed solution at a low temperature, wherein the first component is swollen when brought into contact with an aqueous solution, thereby increasing the volume of the scaffold, and the second component, which is a compound different from the first component, is crosslinkable with the first component and enables the control of degradability by an external stimulus after being crosslinked with the first component, and the drug is a drug for controlling an immunosuppressive action in a solid tumor microenvironment.

In addition, the present invention provides a method of fabricating a soft bio-integrated device, which includes: (a) preparing a first component solution containing a first component; (b) preparing a second component solution containing a second component; (c) preparing a mixed solution by mixing the first component solution and the second component solution; (d) fabricating a cryogel scaffold by crosslinking the mixed solution at a low temperature; and (e) loading a drug into the cryogel scaffold, wherein the first component is swollen when brought into contact with an aqueous solution, thereby increasing the volume of the scaffold, and the second component, which is a compound different from the first component, is crosslinkable with the first component and enables the control of degradability by an external stimulus after being crosslinked with the first component, and the drug is a drug for controlling an immunosuppressive action in a solid tumor microenvironment.

In one embodiment of the present invention, the first component in step (a) may include one or more components selected from the group consisting of hyaluronic acid, hyaluronic acid-methacrylate, poly(glutamic acid), poly(gamma-glutamic acid), poly(amino acid) and derivatives thereof.

In another embodiment of the present invention, the second component in step (b) may include one or more components selected from the group consisting of collagen, hyaluronic acid, hyaluronic acid-aldehyde methacrylate, poly(gamma-glutamic acid), poly(amino acid), chitosan, cellulose, polyacrylate, polyacrylic acid and derivatives thereof.

In still another embodiment of the present invention, the first component in step (a) may be hyaluronic acid-methacrylate (HA-MA), and the second component in step (b) may be hyaluronic acid-aldehyde methacrylate (HA-ald-MA).

In yet another embodiment of the present invention, the second component in step (b) may include collagen, and the first component of step (a) may be poly(gamma-glutamic acid) or hyaluronic acid.

In yet another embodiment of the present invention, in step (a) or (b), the first component or the second component may be included in each solution at 0.1 to 50 mg/mL.

In yet another embodiment of the present invention, the mixed solution in step (c) may further include arginylglycy-laspartic acid (RGD peptide) or an extracellular material (ECM)-derived material, and as a non-limiting example of the ECM-derived material, collagen, elastin or gelatin may be used.

In yet another embodiment of the present invention, the mixed solution in step (c) may further include one or more drugs selected from the group consisting of an anticancer agent for suppressing the growth of a tumor, a immunosuppressive factor-controlling drug, a cancer vaccine, an immunoadjuvant, immune cells for cancer therapy, and a cytokine required for maintaining the activity of the immune cells for cancer therapy.

In yet another embodiment of the present invention, in step (d), the mixed solution may be poured into a mold, and then crosslinked at a low temperature.

In yet another embodiment of the present invention, the crosslinking in step (d) may be performed for 3 to 24 hours at −25 to −4° C.

In yet another embodiment of the present invention, in step (e), one or more drugs selected from the group consisting of an anticancer agent for suppressing the growth of a tumor, a immunosuppressive factor-controlling drug, a cancer vaccine, an immunoadjuvant, immune cells for cancer therapy, and a cytokine required for maintaining the activity of the immune cells for cancer therapy may be further loaded into a cryogel scaffold.

In addition, the present invention provides a method of treating a solid tumor, which includes inserting the soft bio-integrated device into a subject.

According to one embodiment of the present invention, the insertion may be performed by a surgical procedure, and the soft bio-integrated device may be inserted into a site from which solid tumor tissue has been removed.

Advantageous Effects

As a cryogel scaffold according to the present invention is fabricated by mixing two or more components having different degradabilities and crosslinking the mixed product at a low temperature, it can have degradability and/or a swelling ratio, which is(are) suitable for a use and a purpose without affecting mechanical properties, by adjusting concentrations of the components and a mixing ratio thereof. Therefore, due to the cryogel scaffold capable of adjusting degradability, it is expected to expand a field where the cryogel scaffold is used. In addition, the apoptosis of residual cancer cells and cancer cell metastasis can be suppressed by loading an anticancer drug into the cryogel scaffold, removing tumor tissue and then implanting the soft bio-integrated device according to the present invention, and particularly, by loading a drug for controlling an immunosuppressive action into a solid tumor microenvironment, the soft bio-integrated device according to the present invention is effective in cancer treatment in the solid tumor microenvironment exhibiting a low therapeutic effect by an immunosuppressive action.

MODES OF THE INVENTION

Figure 1A:
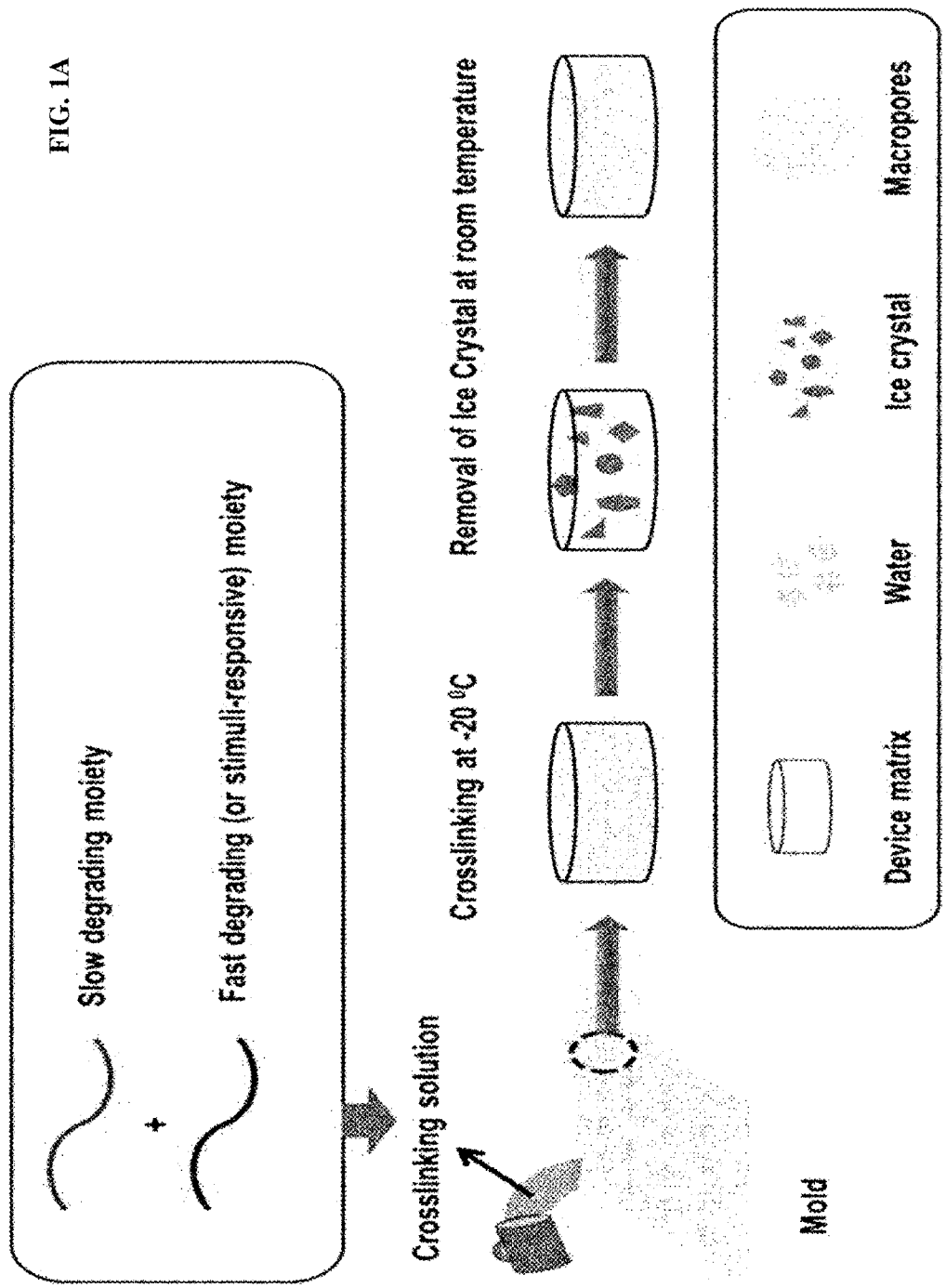
FIG. 1A illustrates a process of fabricating a cryogel scaffold capable of controlling degradability, which includes a material containing two or more components with different degradabilities under physiochemical conditions.

The inventors had made an earnest effort to study a method of fabricating a cryogel scaffold satisfying degradability and/or a swelling ratio, which are required in each field, for wide use of the cryogel scaffold in various fields, and confirmed that a cryogel scaffold fabricated by mixing two or more components with different degradabilities in a suitable ratio and crosslinking the mixed product at a low temperature may adjust the degradability and/or the swelling ratio according to components included therein, the concentration of each component and a mixing ratio of the components, and the mechanical properties of the scaffold may be maintained and its degradability may be adjusted using the chemical structures of components constituting the cryogel scaffold, physiological conditions and various external stimuli. Thus, the present invention was completed.

In addition, the inventors had made an earnest effort to study the development of a porous scaffold used in the biomedical field, particularly, for cancer treatment, confirming that a soft bio-integrated device fabricated by loading a drug into a cryogel scaffold enabling adjustment of the degradability, particularly, has an excellent effect in solid tumor treatment. Thus, the present invention was completed.

The cryogel scaffold of the present invention includes a structure formed by crosslinking a first component swollen when brought into contact with an aqueous solution, thereby increasing the volume of the scaffold, and a second component, which is different from the first component, can be crosslinked with the first component at a low temperature and control degradability by an external stimulus after being crosslinked with the first component.

In addition, the cryogel scaffold of the present invention may be fabricated by (a) preparing a solution containing a first component swollen when brought into contact with an aqueous solution, thereby increasing the volume of the scaffold; (b) preparing a solution containing a second component which is different from the first component, is crosslinkable with the first component and enables the control of degradability by an external stimulus after being crosslinked with the first component; (c) preparing a mixed solution by mixing the first component solution and the second component solution; and (d) crosslinking the mixed solution at a low temperature.

In the present invention, the first component constituting the cryogel scaffold is a hydrophilic material, and is not limited as long as it is swollen by being brought into contact with an aqueous solution to increase the volume of the scaffold, and preferably includes one or more components selected from the group consisting of poly-N-vinylcaprolactam, hydroxyethylmethacrylate (HEMA), gelatin, collagen, hyaluronic acid, cellulose, chitosan, polysaccharides, polyvinyl alcohol-tetraethylortho silicate-alginate-calcium oxide (PTAC), chitosan-agarose-gelatin (CAG), carrageenan, polyacrylate, polyacrylonitrile, polyacrylamide, agarose, alginate, carboxymethyl cellulose (CMC), hydroxypropyl methylcellulose (HPMC), polyethylene glycol, poly(hydroxyethyl methacrylate), poly(vinyl alcohol), casein, poly(amino acid), poly(glutamic acid), poly(gamma-glutamic acid) and fibrinogen, more preferably, one or more components selected from the group consisting of hyaluronic acid, hyaluronic acid-methacrylate, poly(glutamic acid), poly(gamma-glutamic acid), poly(amino acid), and derivatives thereof (derivatives), and even more preferably, is selected from the group consisting of hyaluronic acid-methacrylate, collagen, hyaluronic acid and derivatives thereof.

In addition, in the present invention, the second component constituting the cryogel scaffold is not limited as long as it is different from the first component, is crosslinkable with the first component and enables the control of degradability by an external stimulus after being crosslinked with the first component, and preferably includes one or more components selected from the group consisting of poly-N-vinylcaprolactam, hydroxyethylmethacrylate (HEMA), gelatin, collagen, hyaluronic acid, cellulose, chitosan, polysaccharide, polyvinyl alcohol-tetraethylorthosilicate-alginate-calcium oxide (PTAC), chitosan-agarose-gelatin (CAG), carrageenan, polyacrylate, polyacrylonitrile, polyacrylamide, agarose, alginate, carboxymethyl cellulose (CMC), hydroxypropyl methylcellulose (HPMC), polyethylene glycol, poly(hydroxyethyl methacrylate), poly(vinyl alcohol), casein, poly(amino acid), poly(glutamic acid), poly(gamma-glutamic acid) and fibrinogen, and more preferably include one or more components selected from the group consisting of collagen, hyaluronic acid, hyaluronic acid-aldehyde methacrylate, poly(gamma-glutamic acid), poly(amino acid), chitosan, cellulose, polyacrylate, polyacrylic acid and derivatives thereof.

Non-limiting examples of the derivatives that may be included in the first component or the second component in the present invention include thiolated hyaluronic acid (HA), HA-tyramine, HA-adipic dihydrazide and HA-hexamethylenediamine.

In addition, in the present invention, the second component enables the control of degradability by the chemical structure of a component, physiological conditions and various external stimuli after being crosslinked with the first component by a physical/chemical technique, and the physical/chemical technique for crosslinking with the first component is preferably crosslinking at a low temperature, but the present invention is not limited thereto.

In the present invention, the external stimulus that controls degradability may be one or more stimuli selected from the group consisting of a physiological condition in the body, light, a reductant and an enzyme, but the present invention is not limited thereto.

The cryogel scaffold is irradiated with light as the external stimulus to excite a photosensitizer included in the scaffold, thereby generating reactive oxygen species (ROS), the reductant is not limited as long as it degrades a disulfide bond between the first component and the second component, and as a non-limiting example, dithiothreitol (DDT) is used.

In the present invention, a first component and/or a second component, which constitute(s) the cryogel scaffold, may be included at 10:90 to 90:10, 20:80 to 80:20, 30:70 to 70:30, 40:60 to 60:40, or 50:50 w/v %, thereby adjusting degradability of the scaffold, and the first component and/or the second component may include a functional group (stimuli-responsive functional group) enabling the control of degradability by the stimulus, but the present invention is not limited thereto.

In an exemplary embodiment of the present invention, a cryogel scaffold in which the first component is hyaluronic acid-methacrylate and the second component is hyaluronic acid-aldehyde methacrylate was fabricated, and in another exemplary embodiment, a cryogel scaffold in which the second component is collagen and the first component is poly(gamma-glutamic acid) and/or hyaluronic acid was fabricated, confirming that degradability of the cryogel scaffold varies according to a mixing ratio of the first component and the second component. Specifically, it was confirmed that, as the composition ratio of the hyaluronic acid-aldehyde methacrylate increases, the degradation rate of the collagen/hyaluronic acid cryogel scaffold dramatically increases. In a cryogel scaffold containing collagen/hyaluronic acid, when the concentration of each material is 10 to 20 mg/ml or more, it was confirmed that the degradation rat is dramatically delayed, and in a cryogel scaffold including poly(gamma-glutamic acid), poly(gamma-glutamic acid) has resistance to an enzyme present in the body such as collagenase or hyaluronase, and when it is included at 0.1 to 90 wt %, it was confirmed that the time for degrading the scaffold may significantly decrease.

The term "cryogel" used herein refers to a porous hydrogel prepared at 0° C. or less (subzero temperature). The cryogel may have an interconnected pore structure, and the pore diameter may be adjusted to 20 to 900 μm by a two-step cooling technique.

The cryogel scaffold of the present invention may be fabricated without using a special template or porogen material.

The present invention provides a soft bio-integrated device, which includes the cryogel scaffold, and one or more drugs selected from the group consisting of a drug for controlling an immunosuppressive action in a solid tumor microenvironment, an anticancer agent for suppressing a tumor or the growth of cancer cells, a drug for controlling a immunosuppressive factor, a cancer vaccine, an immunoadjuvant, immune cells for cancer therapy, and a cytokine required for maintaining the activity of the immune cells for cancer therapy.

The soft bio-integrated device of the present invention may be fabricated by loading a drug into the cryogel scaffold, and the drug may be loaded before and/or after the formation of the structure of a scaffold. The loading method may be performed by a method of dropping a drug on the scaffold, or a method of directly injecting a drug into the cryogel scaffold, but there is no limitation on the method as long as the drug can be released from the soft bio-integrated device.

The soft bio-integrated device of the present invention may be fabricated by (a) preparing a solution containing a first component swollen when brought into contact with an aqueous solution, thereby increasing the volume of the scaffold; (b) preparing a solution containing a second component which is different from the first component, is crosslinkable with the first component and enables the control of degradability by an external stimulus after being crosslinked with the first component; (c) preparing a mixed solution by mixing the first component solution, the second component solution and a drug; and (d) crosslinking the mixed solution at a low temperature.

In addition, the soft bio-integrated device of the present invention may be fabricated by (a) preparing a solution containing a first component swollen when brought into contact with an aqueous solution, thereby increasing the volume of the scaffold; (b) preparing a solution containing a second component which is different from the first component, is crosslinkable with the first component and enables the control of degradability by an external stimulus after being crosslinked with the first component; (c) preparing a mixed solution by mixing the first component solution and the second component solution; (d) fabricating a cryogel scaffold by crosslinking the mixed solution at a low temperature; and (e) loading a drug into the cryogel scaffold.

The drug loaded into the fabrication of the soft bio-integrated device may be one or more drugs selected from the group consisting of a drug for controlling an immunosuppressive action in a solid tumor microenvironment, an anticancer agent for suppressing a tumor or the growth of cancer cells, a drug for controlling a immunosuppressive factor, a cancer vaccine, an immunoadjuvant, immune cells for cancer therapy, and a cytokine required for maintaining the activity of the immune cells for cancer therapy, but the present invention is not limited thereto.

The drug for controlling an immunosuppressive action in the solid tumor microenvironment may suppress the activity, survival or proliferation of MDSCs, Tregs, and/or TAMs, non-limiting examples of the drug for suppressing the activation, survival or proliferation of MDSCs may include tadalafil, sildenafil, L-AME, nitroaspirin, celecoxib, NOHA, bardoxolone methyl, D,L-1-methyl-tryptophan, 5-fluorouracil, gemcitabine, 17-DMAG, peptide-Fc fusion proteins, ATRA, vitamin A, vitamin D3, vitamin E, GR1 antibodies, zoledronic acid, sunitinib, axitinib, decetaxel, sorafenib, cucurbitacin B, JSI-124, anti IL-17 antibodies, anti-glycan antibodies, anti-VEGF antibodies, bevacizumab, antracycline, tasquinimod, imatinib and cyclophosphamide, non-limiting examples of the drug for suppressing the activation, survival or proliferation of Tregs may include anti-CD25 antibodies (daclizumab), basiliximab, LMB-2, denileukin diftitox (Ontak), bivalent IL-2 fusion toxin, anti-TGF-beta antibodies, fresolimumab, TGF-betaR kinase inhibitors, LY2157299, soluble TGF-betaR I/II, ipilimumab, tremelimumab, pembrolizumab, nivolumab, TIM-3 antibodies, LAG-3 antibodies, anti-CD39 antibodies, anti-73 antibodies, A(2A)R inhibitors, celecoxib, indomethacin, diclofenac, ibuprofen, TNFR2 antibodies, anti-GITR antibodies, bevacizumab, anti-OX40 (CD134) antibodies, soluble GITR ligand, blockades for chemokine receptors (CCR4, 5, 6 and 10), cyclophosphamide, sunitinib, fludarabine, PI3K p110 (delta) inhibitors, cliniMACs, mogamulizumab, fingolimod, regulators for miRNA (miR-155, miR-146a and miR-181a), 5-aza-2-deoxycytidine, paclitaxel, imatinib, sorafenib, cyclosporin A, tacrolimus, dasatinib, poly-G-oligonucleotide, TLR8 ligands, gemcitabine and 5-fluorouracil, and non-limiting examples of the drug for suppressing the activity, survival or proliferation of TAMs may be CCL2/CCR2 inhibitors (Yondelis and RS102895), M-CSF or M-CSFR inhibitors (anti-M-CSF antibodies, JNJ-28312141 and GW2580), chemoattractants (CCLS, CXCL-12 and VEGF), inhibitors of receptors of the biomaterials, HIFs inhibitors, bisphosphonates, clodronate, dasatinib, anti-FR-beta antibodies, *Shigella flexneri*, legumain, and drugs for inducing CD1d expression.

In addition, the drugs for controlling an immunosuppressive action in the solid tumor microenvironment may serve to suppress an immunosuppressive environmental factor in the solid tumor microenvironment, and the immunosuppressive environmental factor includes cytokines and metabolites, which induce immunosuppression in the solid tumor microenvironment. Non-limiting examples of the immunosuppressive environmental factors include resiquimod (R837), transforming growth factor beta (TGF-β), nitro aspirin, cycloxygenase-2 (COX2), indoleamine 2,3-dioxygenase (IDO), phosphodiesterase-5 (PDE-5), and interleukin 10 (IL-10).

In addition, the drug for controlling an immunosuppressive action in the solid tumor microenvironment may include coactivators that play the role of activating T cells through direct binding in the solid tumor microenvironment. The coactivators may target OX40, CD137, CD27 and CD40, and non-limiting examples of the coactivators include RG7888, urelumab, varlilumab and BMS-986090.

In addition, the drugs for controlling an immunosuppressive action in the solid tumor microenvironment may serve to suppress an immune checkpoint by activating T cells through direct binding in the solid tumor microenvironment, and non-limiting examples of the immune checkpoints include PD-1, PDL-1 CTLA-4, LAG-3, TIM-3, and CEACAM1. Therefore, the drugs serving to suppress an immune checkpoint may include PD-1, PDL-1 CTLA-4, LAG-3, TIM-3, and/or CEACAM1 antibodies, and the antibodies may include ipilimumab, nivolumab, atezolizumab, BMS-986016, TSR-022, and CM-24, but the present invention is not limited thereto.

In addition, the drugs for suppressing a tumor or the growth of cancer cells, that is, anticancer agents, may include one or more selected from the group consisting of DNA methyltransferase inhibitors (DNMTis), histone deacetylase inhibitors (HDACis), and angiogenesis inhibitors, non-limiting examples of the DNMTis include 5-azacytidine, 5-aza-2-deoxycytidine, decitabine, SGI-110, zebularine, CP-4200, cladribine, fludarabine, clofarabine, procainamide, procaine, hydralazine, disulfiram, RG108, nanaomycin A, genistein, equol, curcumin, EGCG, resveratrol, and parthenolide, non-limiting examples of the HDACis include vorinostat, abexinostat, suberoylanilide, hydroxamic acid, belinostat, panobinostat, romidepsin, valproic acid, entinostat, givinostat, resminostat, quisinostat, pracinostat, dacinostat, pyroxamide, CHR-3996, CBHA, trichostatin A, oxamflatin, MC1568, tubacin, PCI-30451, tacedinaline, mocetinostat, chidamide, BML-210, M344, butyrate, sodium butyrate, trapoxin A, apicidin, nicotinamide, splitomicin, EX-527, dihydrocoumarin, tenovin-D3, AGK2, AEM1, AEM2, cambinol, sirtinol, salermide, tenovin-6, TMP-269, psammaplin A, nexturastat A, and RGFP966, and non-limiting examples of angiogenesis inhibitors include bevacizumab (Avastin), itraconazole, carboxyamidotriazole, TNP-470, fumagillin, CM101, IFN-alpha, IL-12, platelet factor-4, suramin, SU5416, thrombospondin, VEGFR antagonists, angiostatic steroids, heparin, cartilage-derived angiogenesis inhibitory factors, matrix metalloproteinase inhibitors, angiostatin, endostatin, 2-methoxyestradiol, tecogalan, tetrathiomolybdate, thalidomide, prolactin, alpha(v)beta(3) inhibitors, linomide, ramucirumab, tasquinimod, ranibizumab, sorafenib (Nexavar), sunitinib (Sutent), pazopanib (Votrient), and everolimus (Afinitor).

In the present invention, the drugs for suppressing the growth of a tumor or cancer cells may be drugs for improving characteristics of an M1 macrophage, drugs for suppressing a mechanism of helping M2 macrophage-based cancer cell growth, or target drugs that can increase an anticancer effect by targeting macrophages in the solid tumor microenvironment, non-limiting examples of the drugs for improving the characteristics of an M1 macrophage include NF-kB agonists such as a TLR agonist, anti-CD40 antibodies, thiazolidinediones, tasquinimod, anti-IL-10R antibodies, anti-IL-10 antibodies, oligonucleotides (Anti-IL-10R, Anti-IL-10), STAT1 agonists such as interferon, SHIP and GM-CSF capable of inducing an M1 pathway, IL-12, and thymosin alpha1, non-limiting examples of the drugs for suppressing a mechanism of helping the M2 macrophage-cancer cell growth include STAT3 inhibitors such as sunitinib, sorafenib, WP1066, corosolic acid, oleanolic acid, STAT6 inhibitors and inhibitors of M2 pathways (c-Myc, PPAR-alpha/gamma, PI3K, KLF4, HIFs, Ets2, DcR3 and mTOR), HRG, CuNG, MDXAA, silibinin, and PPZ, and non-limiting examples of the target drugs for increasing an anticancer effect by targeting a macrophage in the solid tumor microenvironment include paclitaxel, docetaxel, 5-fluorouracil, alendronate, doxorubicin, simvastatin, hydrazinocurcumin, amphotericin B, ciprofloxacin, rifabutin, rifampicin, efavirenz, cisplatin, theophyline, Pseudomonas exotoxin A, zoledronic acid, trabectedin, siltuximab (anti-IL-6 antibodies), dasatinib, CpG-ODN, interferon-alpha, beta, gamma, GM-CSF, IL-12, thymosin alpha-1, sunitinib, bisphosphonates, 5,6-dimethylxanthenone-4-acetic acid, silibinin, CCL2-CCR2 inhibitors (PF-04136309, trabectedin and carlumab), CSF1-CSF1R signaling blockers (BLZ945, PLX3397, emactuzumab (RG7155), AMG-820, IMC-CS4, GW3580 and PLX6134) and ligands of toll-like receptor 7 (imiquimod and 852A), NF-kB inhibitors (N-acetyl-1-cystein, vitamin C, bortezomib, aspirin, salicylates, indolecarboxamide derivatives, quinazoline analogues, thalidomide and, prostaglandin metabolites), HIF-1 inhibitors 2ME2, 17-AAG, camptothecin, topotecan, pleurotin, 1-methylpropyl, 2-imidazolyl disulfide and YC-1), and CXCR4 agonists (AMD3100, AMD1498, ALX40-4C, T22, T140, CGP64222 and KRH-1636).

More specifically, the TGF-beta inhibitors may include SB-505124 and/or LY-364974, the nitro aspirins may include NCX 4040, the COX-2 inhibitors may include celecoxib, the IDO inhibitors may include indoximod and NLG919, and the PDE-5 inhibitors may include tadalafil (Cialis), but the present invention is not limited thereto.

The "cancer vaccine" used herein is not limited as long as it includes a cancer cell-specific antigen, and specifically, may include one or more selected from the group consisting of proteins, peptides, DNA and RNA, which are isolated from lysates of cancer cells, and preferably, include cancer cell-specific antigens isolated from lysates of cancer cells in a region into which the soft bio-integrated device of the present invention will be implanted, but the present invention is not limited thereto.

The "immunoadjuvant" used herein is not limited as long as it is a material that activates the immune function of a subject, and non-limiting examples may include toll-like receptor agonists (TLR agonist), saponin, antiviral peptides, inflammasome inducers, NOD ligands, cytosolic DNA sensor (CDS) ligands, and stimulators of interferon genes (STING) ligand, and the toll-like receptor agonists refer to components that can induce a signaling reaction by a TLR signaling pathway as a direct ligand or through the indirect generation of endogenous or exogenous ligands. The toll-like receptor agonists may be natural or synthetic toll-like receptor agonists, and include a combination of one or two or more toll-like agonists, but the present invention is not limited thereto. The term "immunoadjuvant" used herein may be interchangeably used with an "immune-activating adjuvant" and an "immunoactivator."

The toll-like agonists may cause a signaling reaction through TLR-1, and may include, for example, tri-acylated lipopeptides (LPs); phenol-soluble modulin; *Mycobacte-*

*rium tuberculosis* LP; S-(2,3-bis(palmitoyloxy)-(2-RS)-propyl)-N-palmitoyl-(R)-Cys-(S)-Ser-(S)-Lys(4)-OH; *Borrelia burgdorfei* LP; trihydrochloride (Pam3Cys) LPs that mimic the acetylated amino terminus of OspA LP, and combinations thereof, and the toll-like agonist may be a TLR-2 agonist such as Pam3Cys-Lip; a TLR-3 agonist such as poly IC type (Poly (I:C), Poly(ICLC) or Poly(IC12U)) or Ampligen; a TLR-4 agonist such as an envelope protein construct of *Shigella flexneri*, or AGP, CRX-527, MPLA, PHAD, 3D-PHAD, GLA or a combination thereof; a TLR-5 agonist such as flagellin or a fragment thereof; a TLR-7 or TLR-8 agonist such as an imidazoquinoline molecule (imiquimod, R837, resiquimod, R848), VTX-2337, CRX642, imidazoquinoline covalently binding to a phosphorous- or phospholipid group or a combination thereof; and a TLR-9 agonist such as an immunostimulatory oligonucleotide, particularly, an immunostimulatory oligonucleotide including one or more CpG motifs, but the present invention is not limited thereto.

In addition, the saponin may be selected from the group consisting of QS21, Quil A, QS7, QS17, β-escin, digitoninum and combinations thereof, the anti-viral peptide may include KLK, the inflammasome inducer may be trehalose-6,6-dibehenate (TDB), the NOD ligand may be M-TriLYS (NOD2 agonist-synthetic muramyl tripeptide) or an NOD2 agonist (N-glycosylated muramyl dipeptide), the CDS ligand may be Poly(dA:dT), and the STING ligand may be cGAMP, di-AMP or di-GMP, but the present invention is not limited thereto.

In addition, the immunoactivator is a material having two types of agonists, and may be CL401 (Dual TLR2 & TLR7 agonist) and CL429 (Dual TLR2 & NOD2 agonist), but the present invention is not limited thereto.

In addition, the immunoactivator may be selected from the group consisting of Pam3Cys-Lip, Poly(I:C), CRX-527, MPLA, flagellin, imiquimod, resiquimod, CpG, QS21, Mur-NAc-Ala-D-isoGln-Lys (M-TriLys), trehalose-6,6-dibehenate (TDB), 8837, Poly(dA:dT), cGAMP and combinations thereof, but the present invention is not limited thereto.

The "immune cells for cancer therapy" used herein is not limited as long as they are activated by a cancer vaccine to recognize a cancer antigen, and may particularly include one or more cells selected from the group consisting of dendritic cells, natural killer cells and T cells.

The immune cells for cancer therapy, which are loaded into the soft bio-integrated device of the present invention, may have activity like that in vitro, and may significantly improve therapeutic efficacy of inhibiting the growth of cancer or preventing the recurrence and/or metastasis of cancer.

The "cytokine required for maintaining the activity of immune cells for cancer therapy" used herein is a material helping in maintaining and increasing the activity of the immune cells for cancer therapy, and when loaded into the soft bio-integrated device of the present invention to be inserted into a subject, may effectively have an anticancer immune function in a subject only with a smaller number of immune cells than when only immune cells for cancer therapy are directly injected into the subject.

In addition, the soft bio-integrated device may further include a material which is inserted in vivo to increase adhesion to a cell, and may more stably and continuously release a drug at an implantation site by including the material that can increase adhesion. The material capable of increasing adhesion may be arginylglycylaspartic acid (RGD peptide) or an extracellular material (ECM)-derived material, and non-limiting examples of the ECM-derived materials may include collagen, elastin and gelatin.

The soft bio-integrated device of the present invention enables sustained release of a loaded drug, but the present invention is not limited thereto.

The soft bio-integrated device of the present invention may include a cryogel scaffold whose degradability is adjusted, thereby regulating the release behavior of a drug required for maintaining the control of an immunosuppressive factor and immunoactivation and/or significantly increasing an effective duration by the adjustment of degradability.

The soft bio-integrated device may be inserted into a subject to be used in treatment of a solid tumor, and the insertion of the soft bio-integrated device may be performed by a surgical procedure, and specifically, may be implanted near a site of solid tumor tissue or near a site from which solid tumor tissue has been removed.

The "subject" used herein may be a mammal such as a rat, livestock, mouse or a house, and specifically, may be a companion dog, a race horse or a human, in need of treatment of a solid tumor, and preferably, a human Hereinafter, to help in understanding the present invention, exemplary examples will be suggested. However, the following examples are merely provided to more easily understand the present invention, and not to limit the present invention.

EXAMPLES

Example 1

Fabrication of Cryogel Scaffold Including Hyaluronic Methacrylate (HA-MA) and Hyaluronic Aldehyde Methacrylate (HA-ald-MA)

Figure 2:
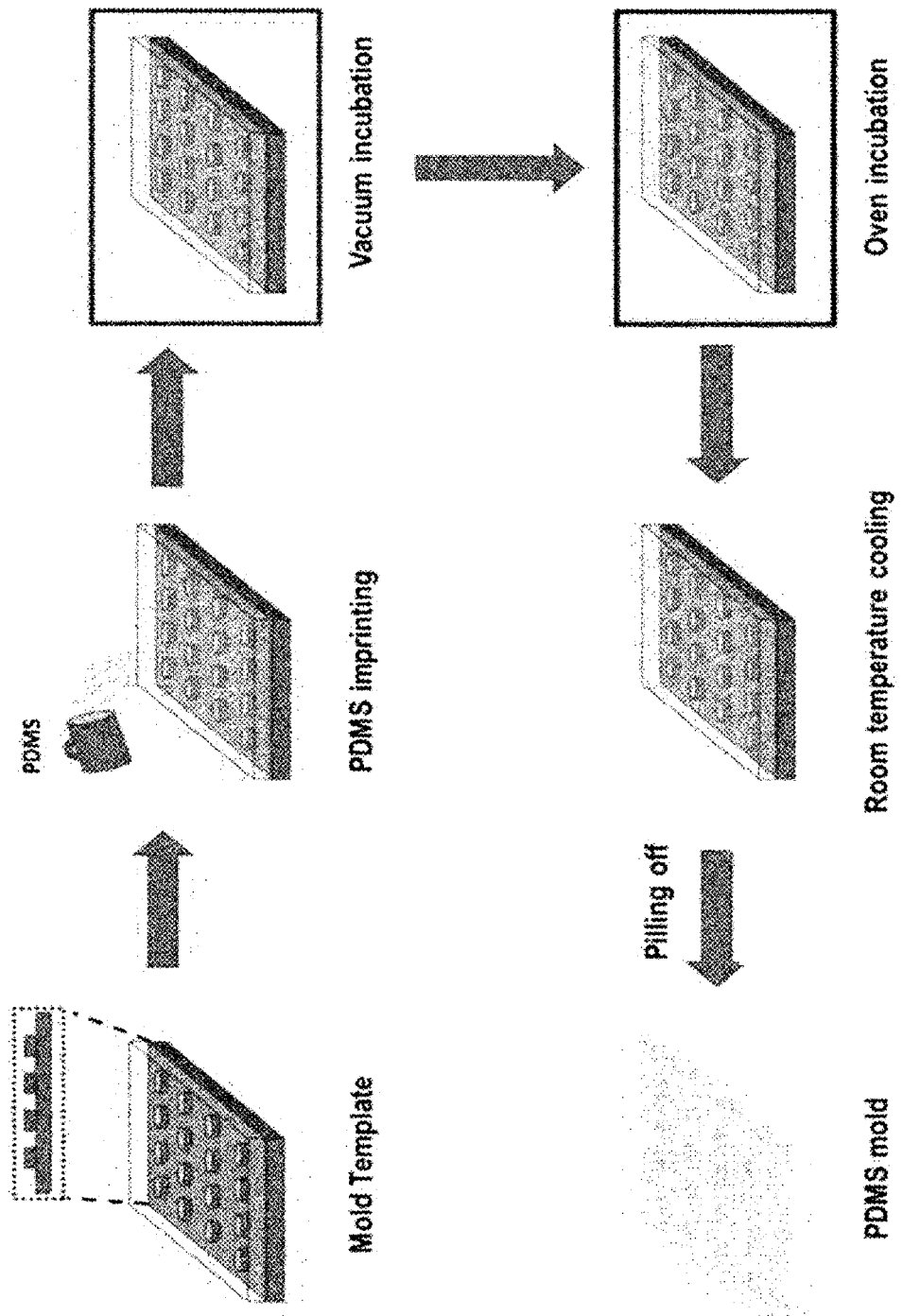
FIG. 2 illustrates a process of manufacturing a mold capable of forming the structure of a scaffold to fabricate a cryogel scaffold.
Figure 3:
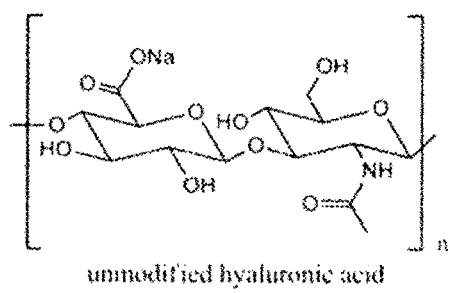
FIG. 3 illustrates a chemical crosslinking reaction for fabricating a hyaluronic acid-based cryogel scaffold.
Figure 3:
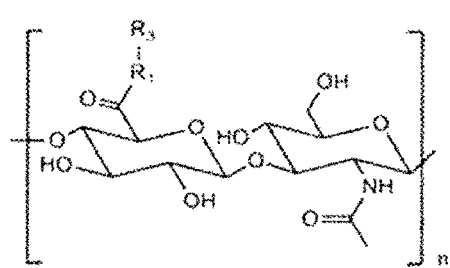
Figure 3:
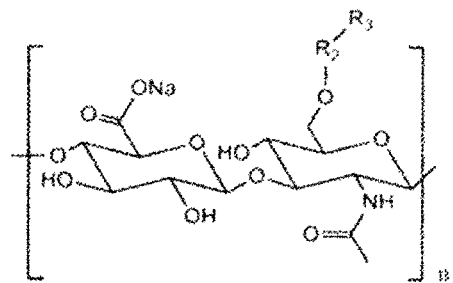
Figure 3:
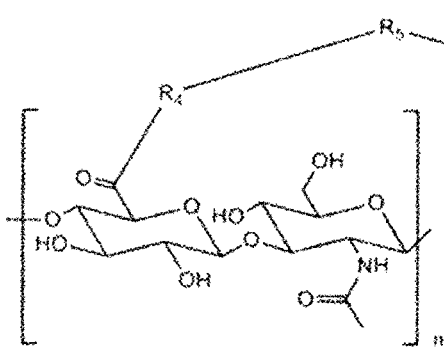
Figure 3:
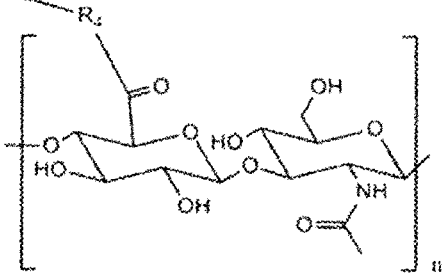
Figure 4:
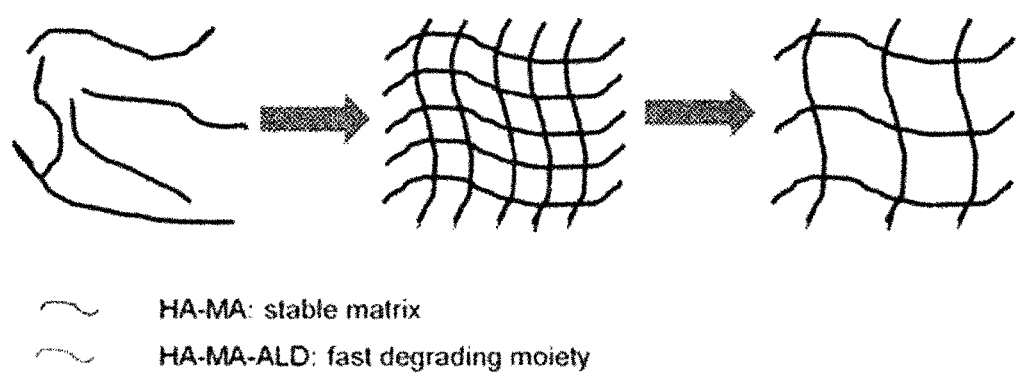
FIGS. 4 and 5 illustrate a method of fabricating a cryogel scaffold capable of adjusting degradability, which includes HA-MA and MA-ald-MA, and adjustment of degradability thereof.
Figure 5:
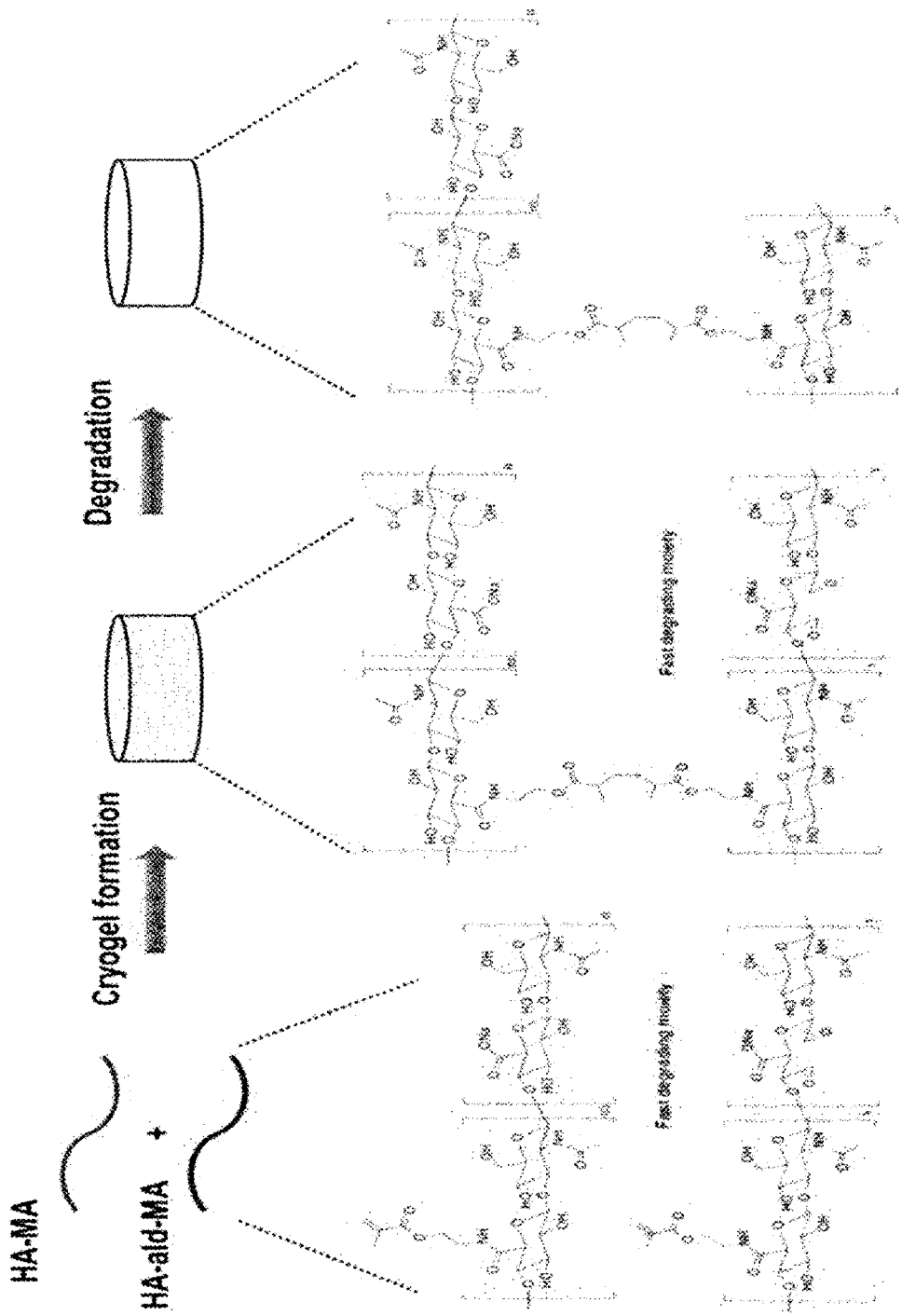
Figure 11:
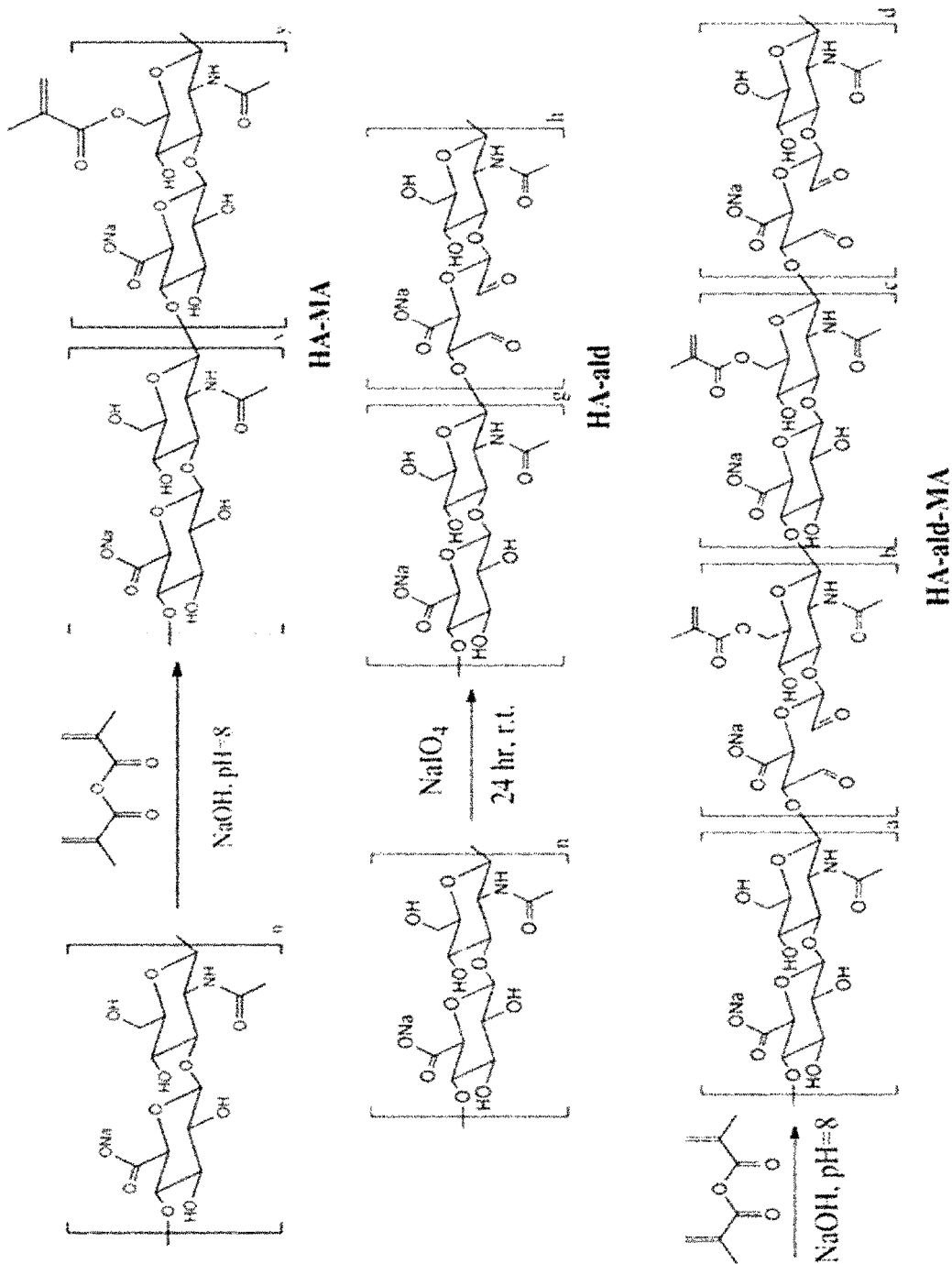
FIG. 11 illustrates a process of synthesizing hyaluronic acid-methacrylate (HA-MA) and hyaluronic acid-aldehyde methacrylate (HA-ald-MA).
Figure 12A:
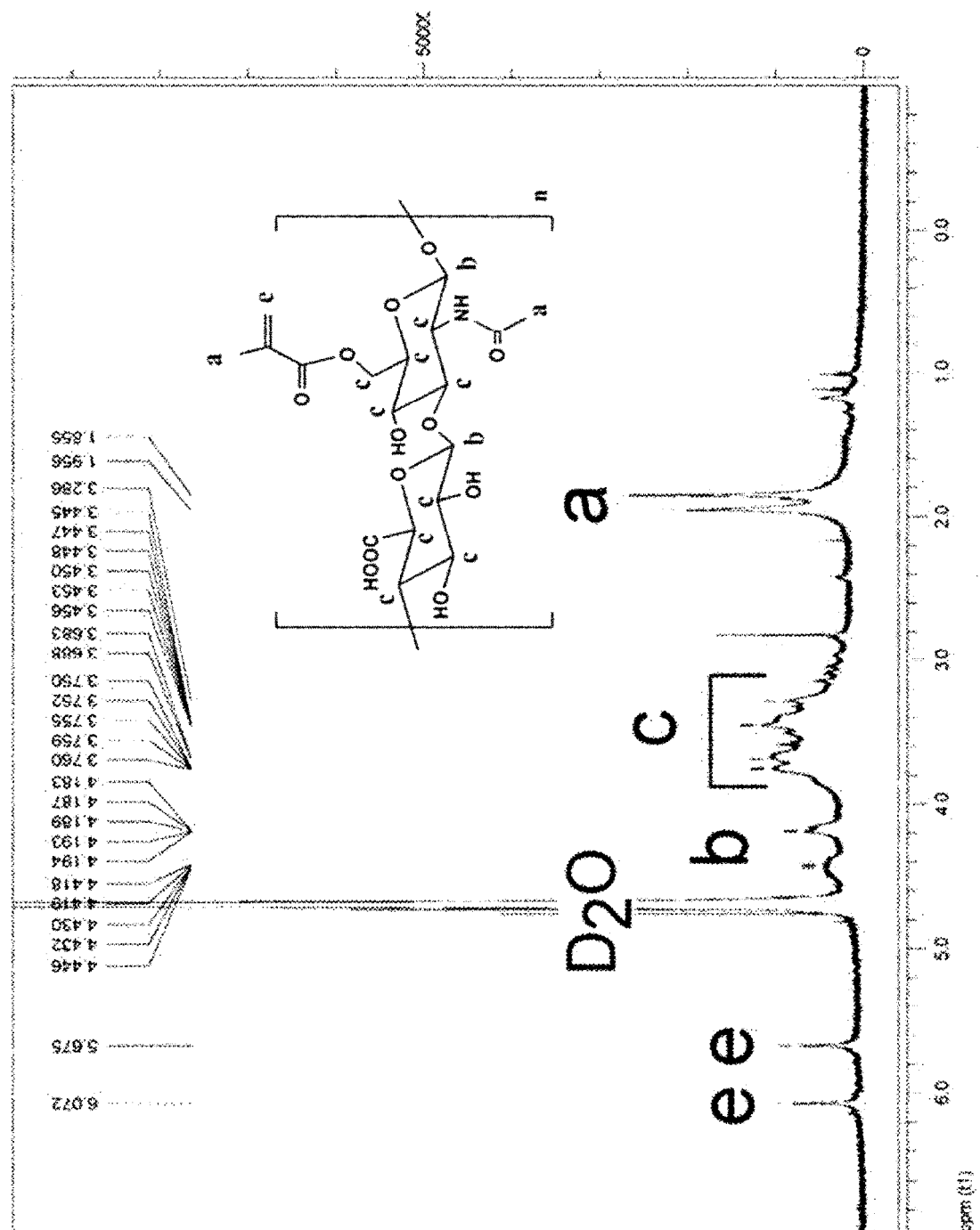
FIGS. 12A to 12D are H-NMR spectra of HA-MA (A)+HA-ald-MA (B) blend-based cryogel scaffolds, respectively.
Figure 12B:
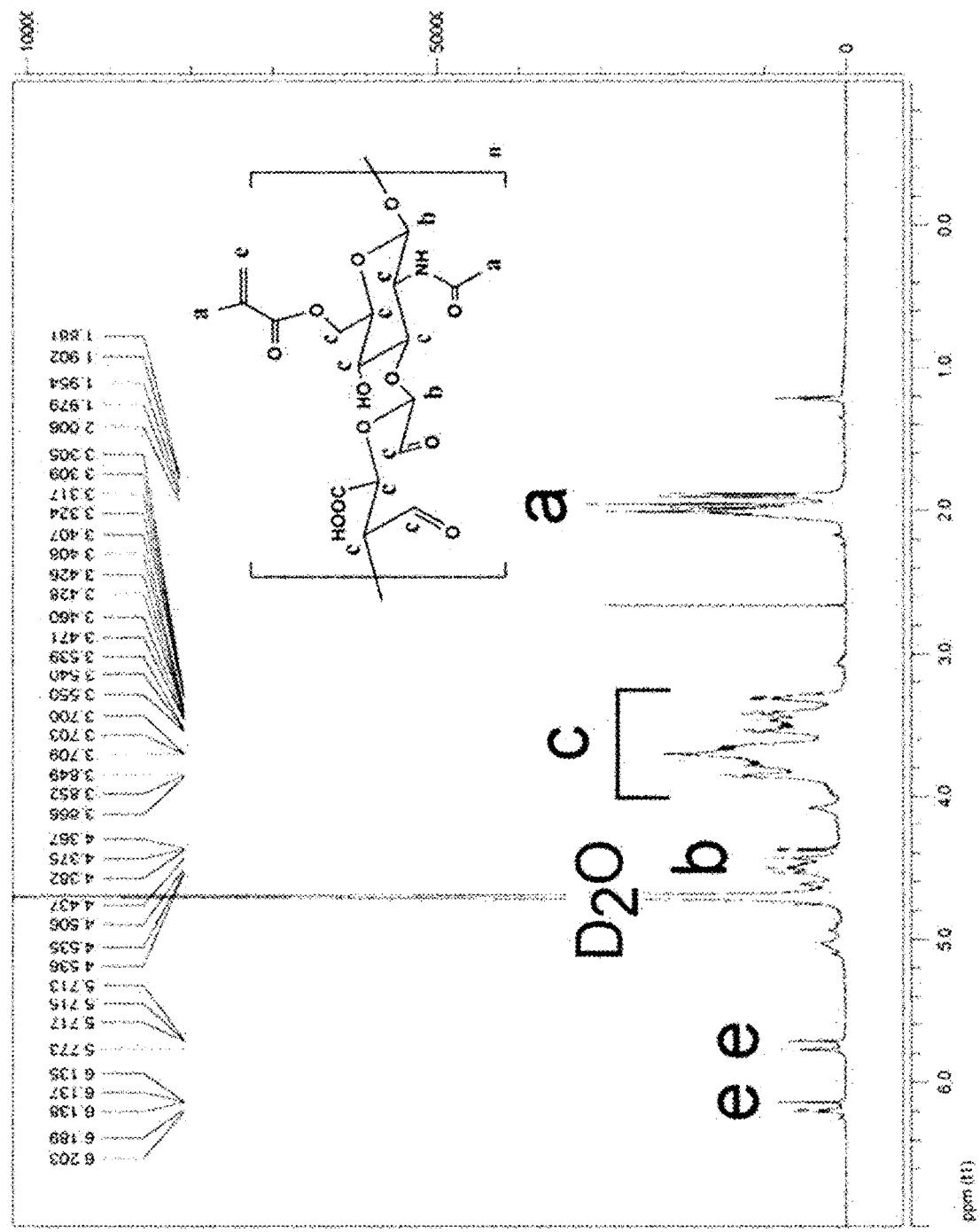
Figure 12C:
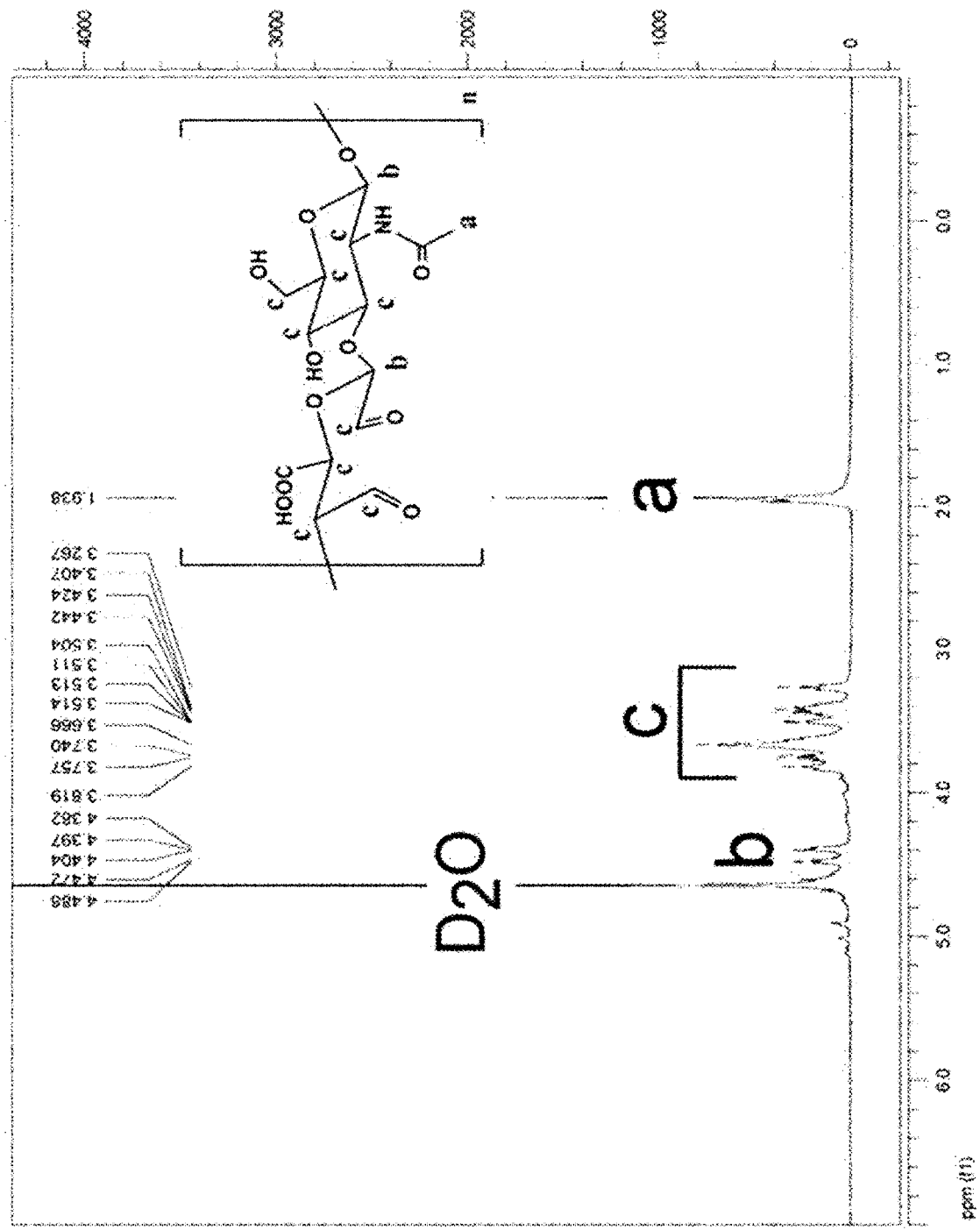
Figure 12D:
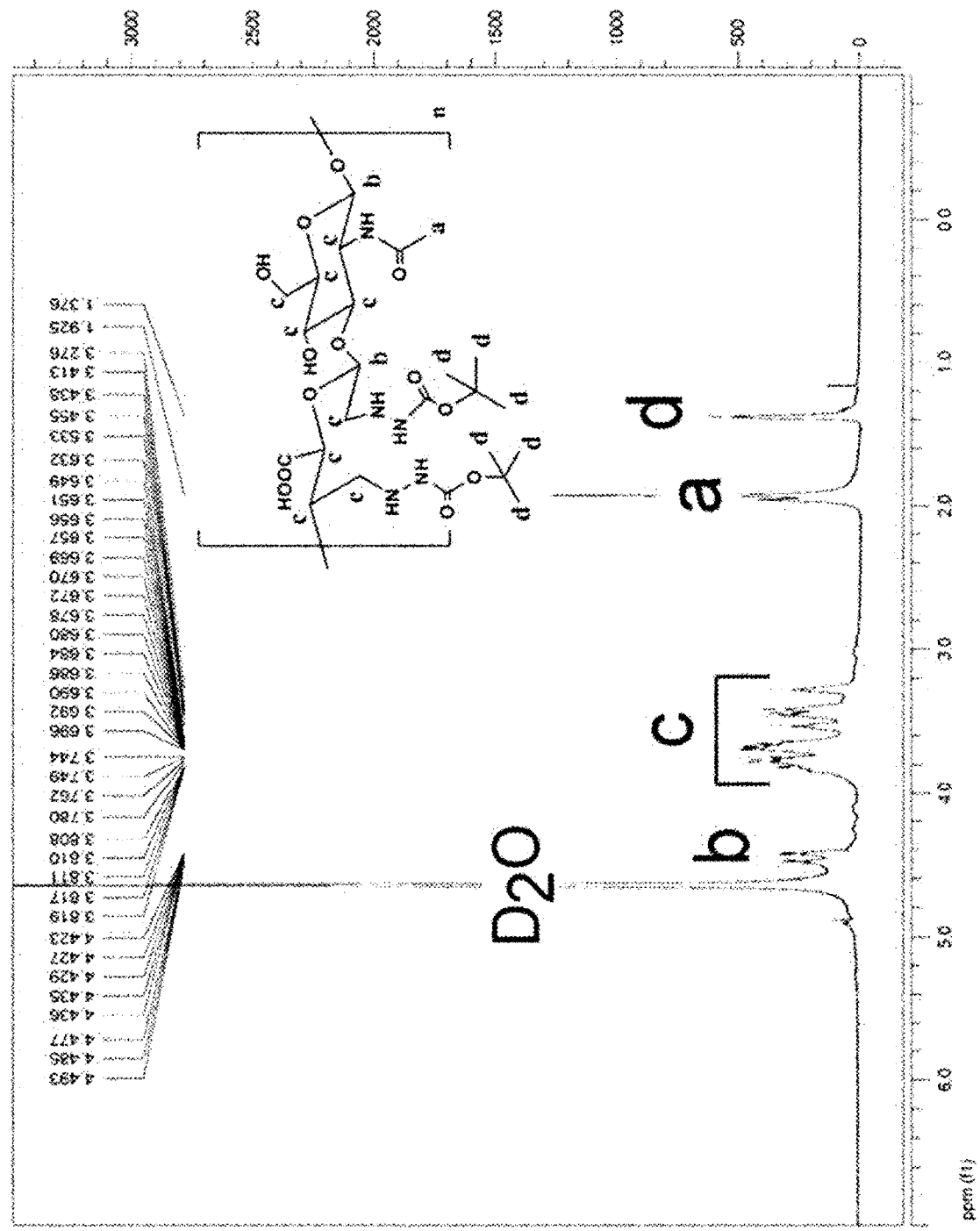

As shown in FIG. 1A, a first component and a second component, which have different degradabilities, were mixed in an aqueous solution under physiochemical conditions, the resulting solution was poured into a mold manufactured by a method shown in FIG. 2, frozen at a low temperature and slowly crosslinked, and then ice crystals were removed using a freeze-drying method, thereby fabricating a cryogel scaffold having cross-linked pores. In this example, the first component was hyaluronic acid-methacrylate (HA-MA), and the second component was hyaluronic acid-aldehyde methacrylate (HA-ald-MA). The schematic diagram of the synthesis of HA-MA and HA-ald-MA is shown in FIG. 11, and specifically, the synthesis of HA-MA and HA-ald-MA and the fabrication of the cryogel scaffold including HA-MA/HA-ald-MA were performed as follows.

1-1. HA-MA Synthesis

Hyaluronic acid (HA, 500 kDa, Bioland, Chungnam, South Korea) was dissolved in 100 mL of distilled water at a concentration of 10 mg/mL, and 3.85 g of methacrylic anhydride (MA, Sigma-Aldrich, South Korea) was added. In addition, pH was adjusted to 8 using 5N sodium hydroxide, and the resulting solution was stirred in a dark place at room temperature, dialyzed (12-14 KDa cutoff) in distilled water for 48 hours and freeze-dried, thereby preparing HA-MA.

1-2. HA-ald Synthesis

Hyaluronic acid (HA, 500 kDa, Bioland, Chungnam, South Korea) was dissolved in 100 mL distilled water at a concentration of 10 mg/mL, and 534 mg of sodium periodate (NaIO$_4$, Sigma-Aldrich, South Korea) was added, and then the resulting solution was stirred for 24 hours in a dark place at room temperature for a sufficient oxidation reaction. In addition, to terminate the oxidation reaction, 1 g of ethylene glycol (Sigma-Aldrich, South Korea) was added and stirred at room temperature for 1 hour, and the resulting solution was dialyzed (12-14 KDa cutoff) in distilled water for 48 hours and freeze-dried, thereby preparing HA-ald.

1-3. HA-ald-MA Synthesis 1 g of the HA-ald prepared by the method of Example 1-2 was dissolved in 100 mL of distilled water, and 3.85 g of methacrylic anhydride (MA, Sigma-Aldrich, South Korea) was added. Subsequently, pH was adjusted to 8 using 5N sodium hydroxide, and the resulting solution was stirred at room temperature in a dark place, dialyzed (12-14 KDa cutoff) in distilled water for 48 hours and freeze-dried, thereby preparing HA-ald-MA.

1-4. Fabrication of HA-MA/HA-ald-MA Blend-Based Cryogel Scaffold 100 mg of the HA-MA and 100 mg of the HA-ald-MA, which had been prepared by the methods in Examples 1-1 and 1-3, respectively, were dissolved in phosphate buffered saline (PBS) at various ratios at 4° C. to have a concentration of 10 mg/mL, thereby preparing mixed solutions with various ratios. In addition, 30 mg of ammonium persulfate (USB Corporation, USA) was added to the mixed solution and mixed, and 60 μL of N,N,N',N'-tetramethylethylenediamine (Sigma-Aldrich, South Korea) was added to the mixed solution and completely mixed to induce a crosslinking reaction between HA-MA and HA-ald-MA. The mixture was rapidly transferred to a PDMS mold and stored for 24 hours at −20° C., thereby fabricating a cryogel scaffold including HA-MA/HA-ald-MA. The scaffold was sterilized using a 70% ethanol solution, and then washed three times with PBS.

1-5. Characterization

Figure 13:
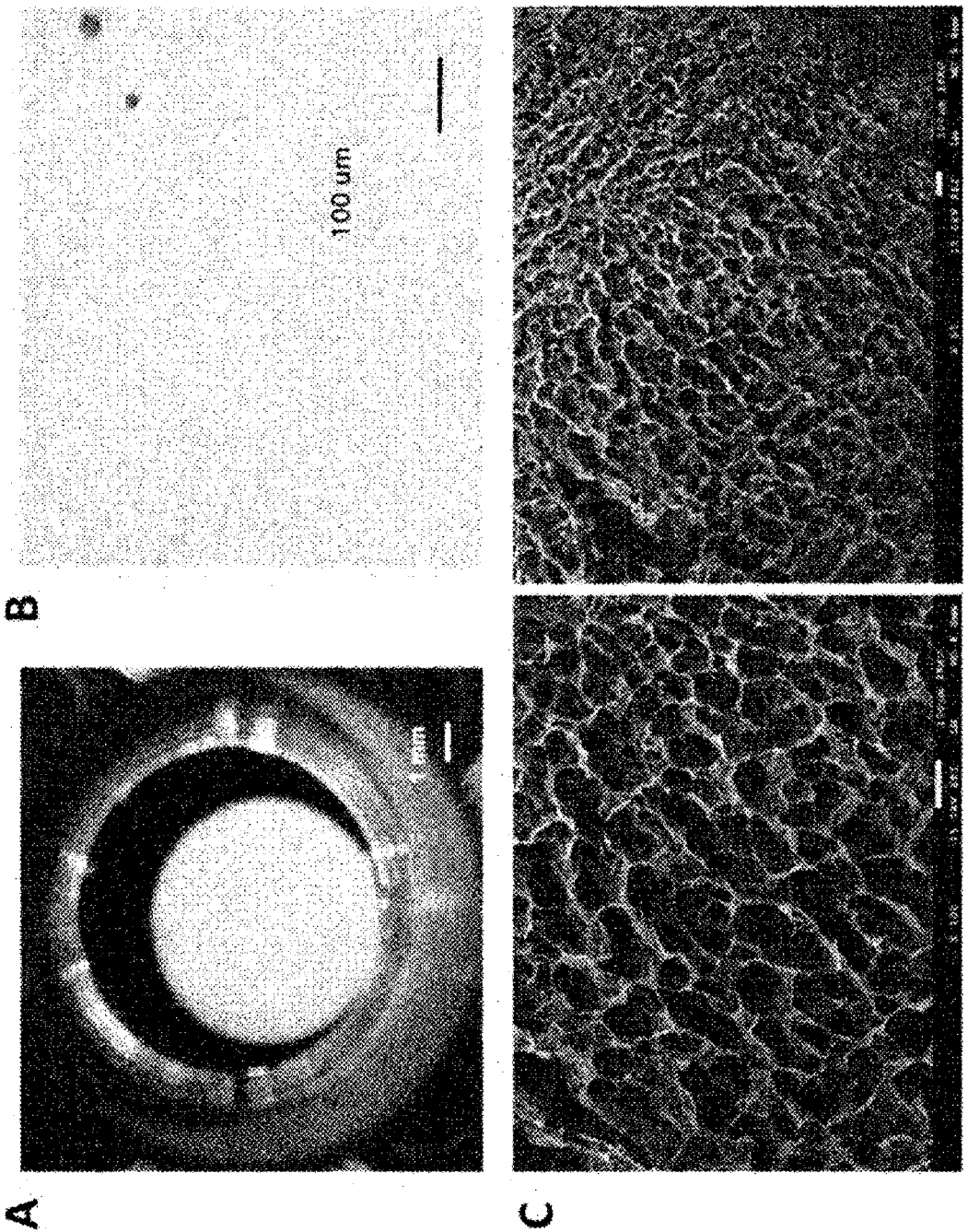
FIG. 13 is a set of images of the appearance (A) and pore structures (B and C) of a cryogel scaffold containing HA-MA and HA-ald-MA.
Figure 14:
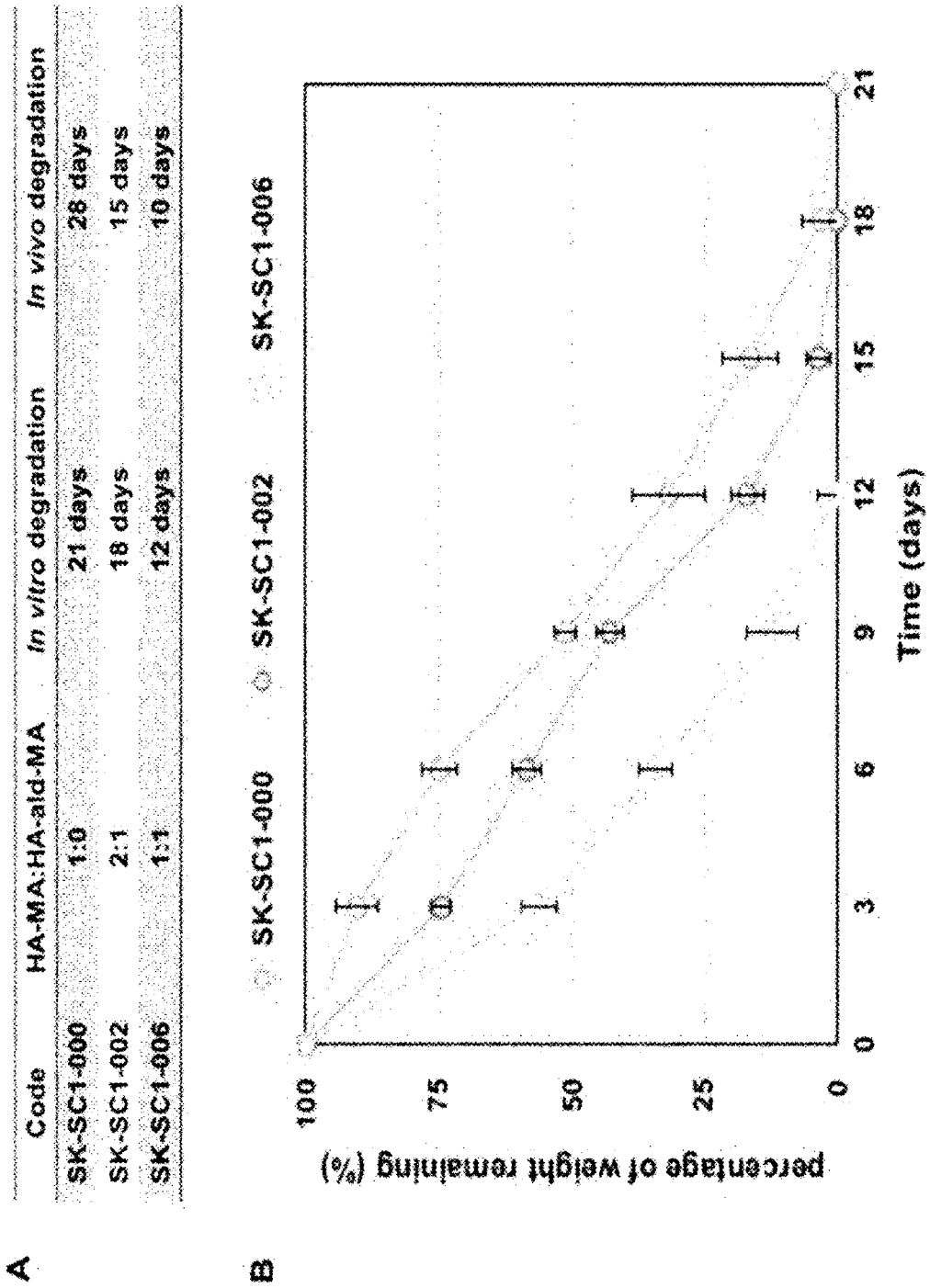
FIG. 14 is a table (A) showing in vitro and in vivo degradation properties of cryogel scaffolds based on a HA-MA/HA-ald-MA blend with various mixing ratios and a graph (B) showing the degree of degradation over time under an in vitro condition.
Figure 15:
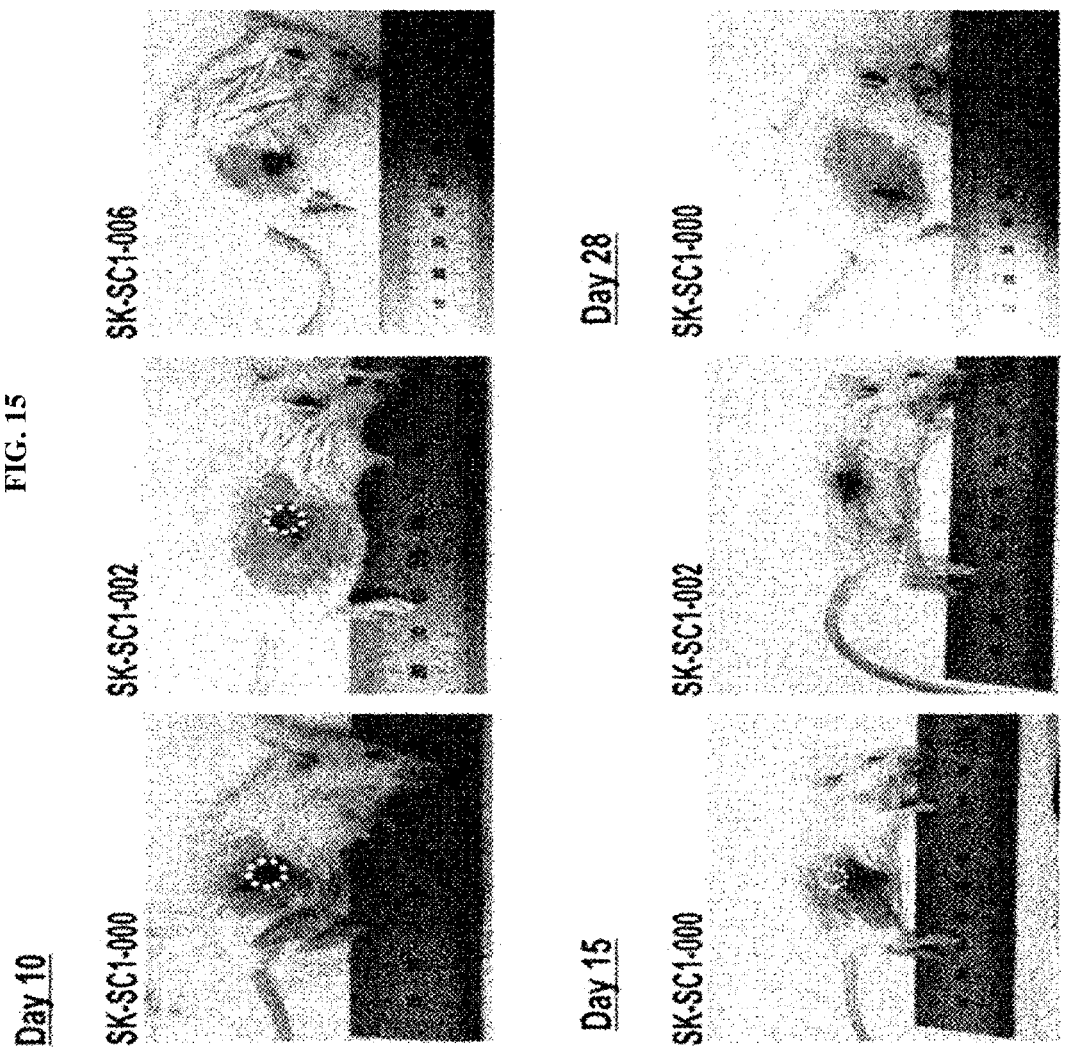
FIG. 15 is a set of images confirming shapes of scaffolds degraded for 10, 15 and 28 days after the subcutaneous implantation of the cryogel scaffolds based on HA-MA/HA-ald-MA blend(s) with various mixing ratios into mice.

The polymer synthesized in each step was dissolved in $D_2O$ at a concentration of 10 mg/mL, and then 1H NMR spectra (Unity Inova, 500 MHz, Varian Technology, USA) were measured. The results are shown in FIGS. 12A to 12D. The structure of the freeze-dried scaffold was cut into sections using an optical microscope (Olympus), and observed using a scanned electron microscope (JSM6700F, JEOL Ltd., Japan). The result is shown in FIG. 13. To measure biodegradability of the scaffold in an in vitro environment, the fabricated scaffold was immersed in 1 mL of PBS or hyaluronidase (10 U/mL), the remaining undegraded scaffold was filtered over time (every 3 days), freeze-dried and weighed. The result is shown in FIG. 14. Subsequently, to measure biodegradability of the scaffold in an in vivo environment, the fabricated scaffold was washed three times or more using a 70% EtOH solution and distilled water and subcutaneously injected into Balb/c mice (female, 6-week-old, Charles River Laboratories, South Korea), and morphological changes of the scaffold after 10, 15 and 28 days were observed. The result is shown in FIG. 15.

Example 2

Fabrication of Cryogel Scaffold Consisting of Hyaluronic Acid/Collagen

Figure 6:
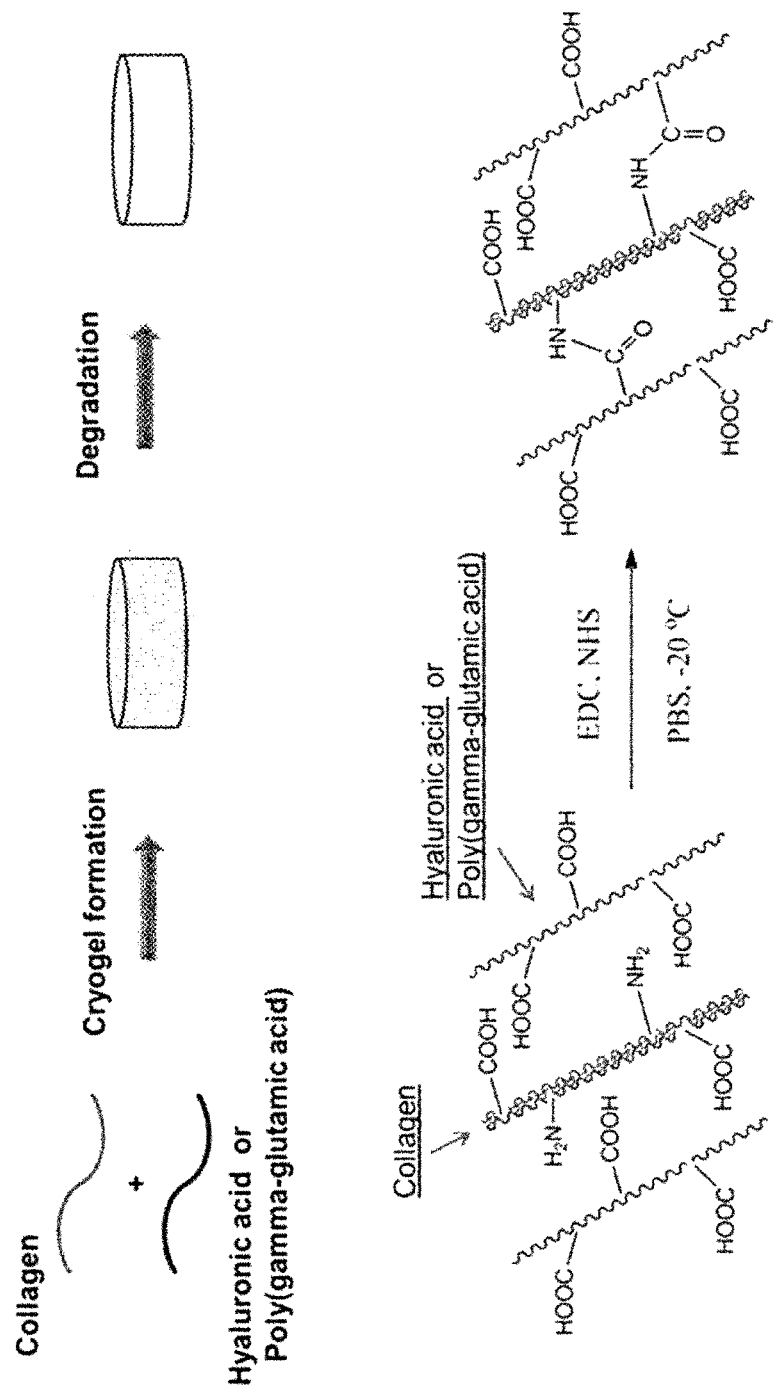
FIG. 6 schematically illustrates a method of fabricating a cryogel scaffold capable of adjusting degradability, which includes collagen and hyaluronic acid or poly(gamma-glutamic acid), and the adjustment of degradability thereof.
Figure 7:
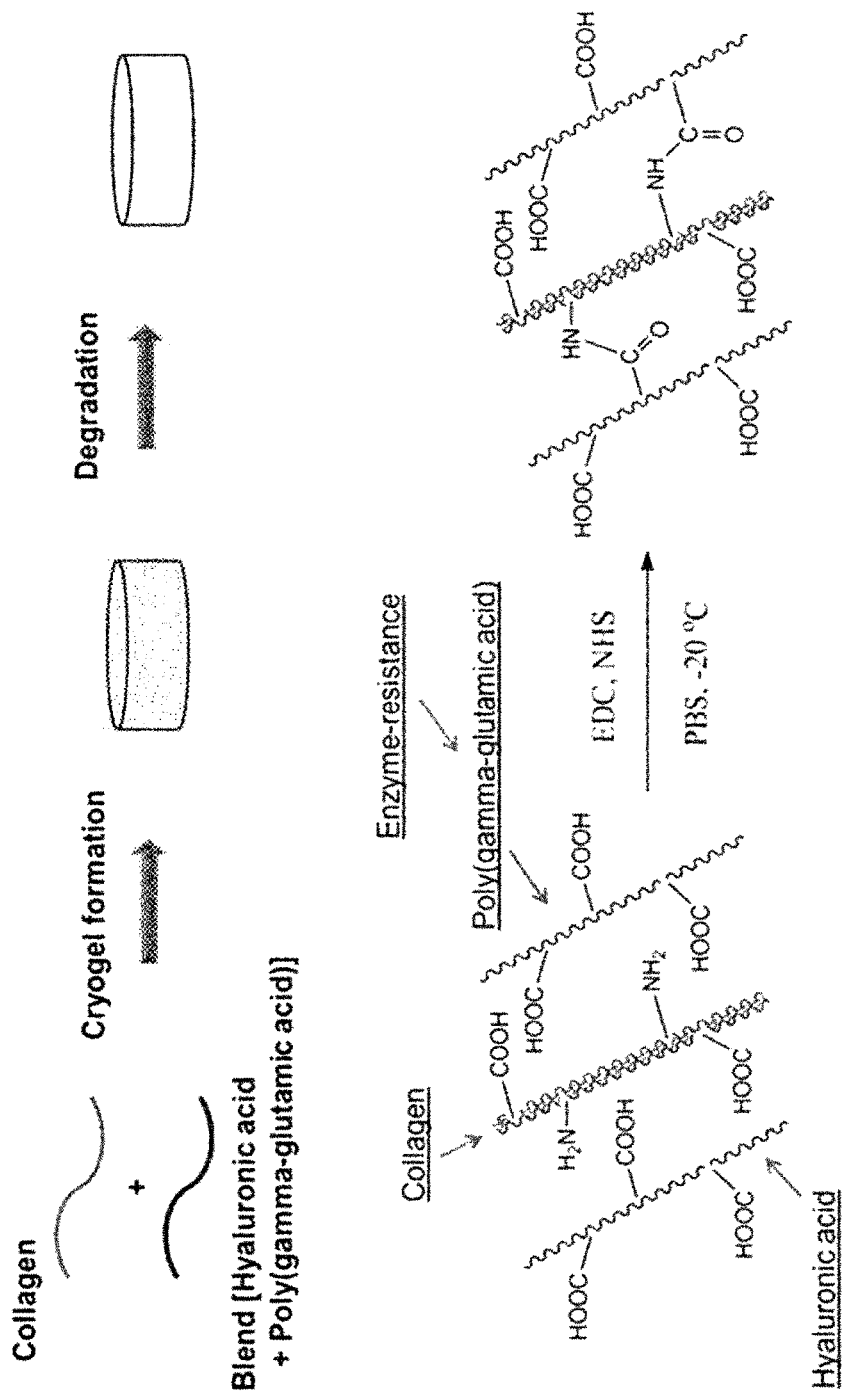
FIG. 7 illustrates a method of fabricating a cryogel scaffold capable of adjusting degradability, which includes collagen, hyaluronic acid and poly(gamma-glutamic acid), and the adjustment of degradability thereof.
Figure 17:
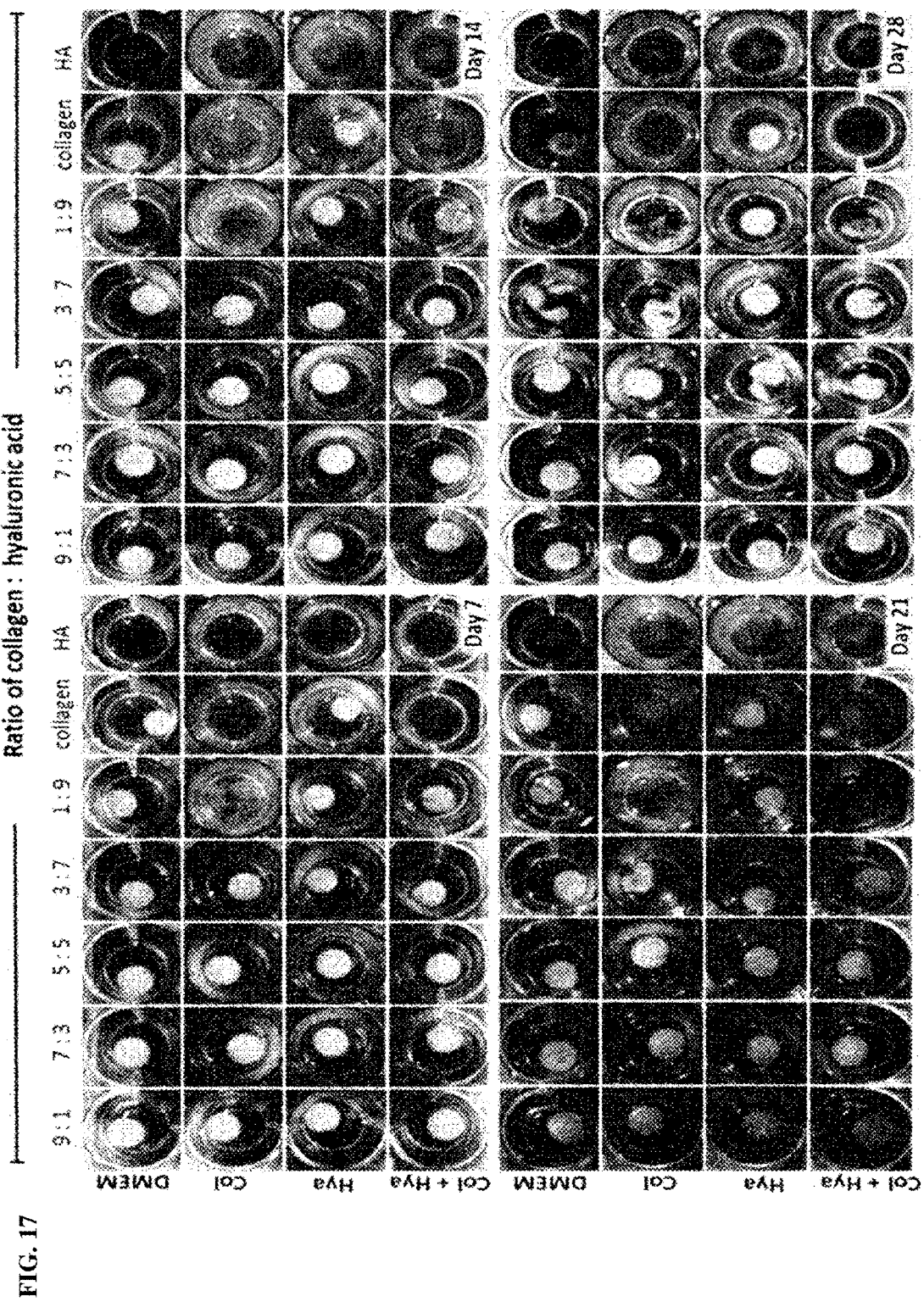
FIG. 17 is a set of images observing the degradation behavior of hyaluronic acid/collagen blend-based cryogel scaffolds fabricated through mixing with various ratios and crosslinking under an in vitro condition.
Figure 18:
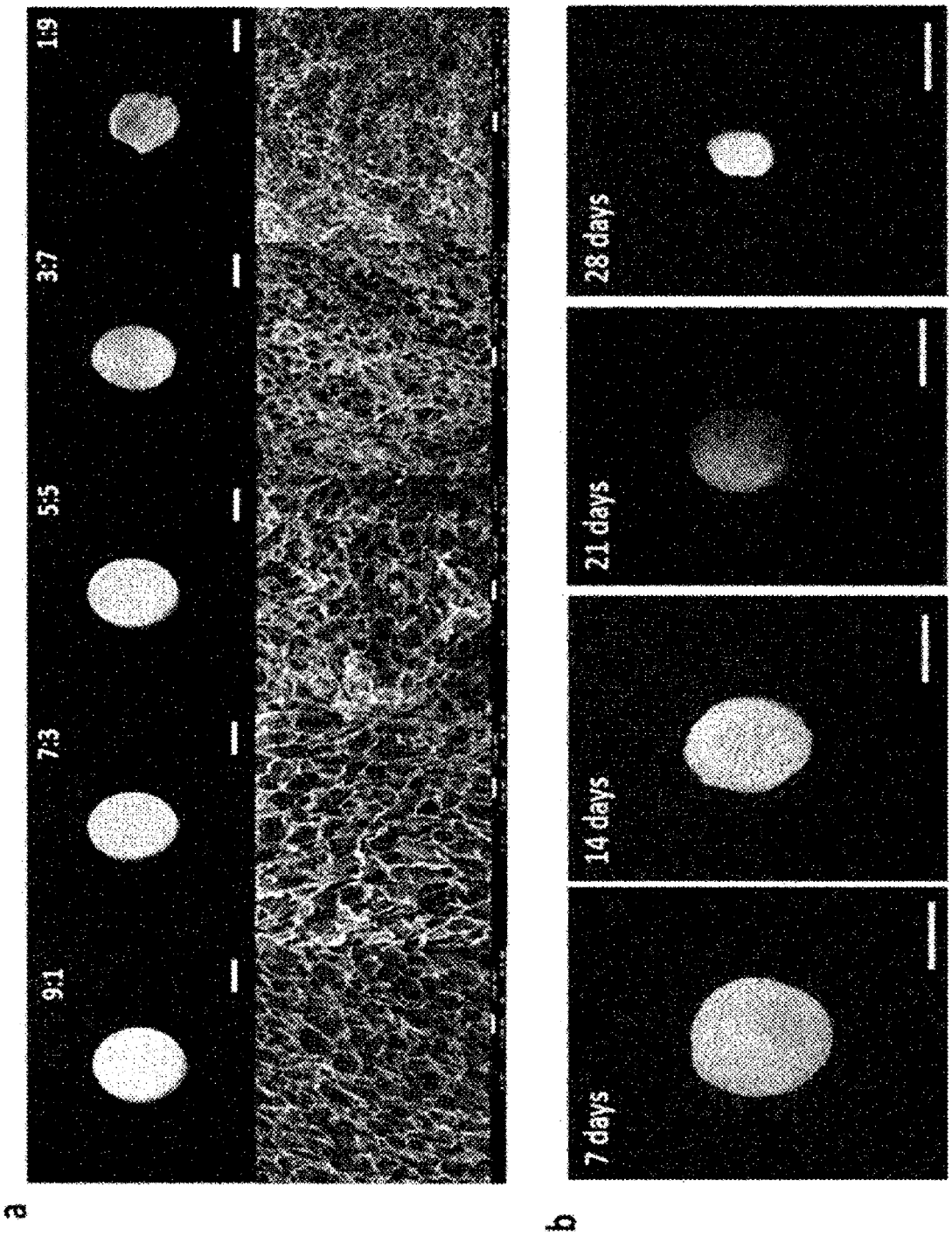
FIG. 18 is (A) a set of scanning electron microscopy images of hyaluronic acid/collagen blend-based cryogel scaffolds fabricated by mixing with various ratios and crosslinking and (B) images showing the degradation behavior of a 5:5 blend scaffold under an in vivo condition.

Collagen (type I, Bioland, Cheonan, South Korea) was dissolved in sterilized PBS at 10 mg/mL (overnight at 4° C.), hyaluronic acid (HA, 500 kDa, Bioland, Chungnam, South Korea) was dissolved in sterilized PBS at 10 mg/mL, and the collagen and the hyaluronic acid were mixed at various volume ratios and then stirred using a magnetic stirrer at 4° C. and 500 rpm for 12 hours. 250 μL of the mixed solution (scaffold solution) was put into a PDMS mold, frozen for 9 hours at −20° C. and freeze-dried for 12 hours. The sample was immersed in a 2 mL of an ethanol solution containing 50 mM EDC/20 mM NHS for 12 hours at −20° C., washed five times for 15 minutes using DI and freeze-dried again for 12 hours, thereby fabricating a cryogel scaffold consisting of hyaluronic acid/collagen (FIG. 6). To measure biodegradability of the scaffold in an in vitro environment, the fabricated scaffold was immersed in collagenase or hyaluronidase, and the degradability of the scaffold was observed after 7, 14, 21 and 28 days. The result is shown in FIG. 17. Subsequently, to measure the biodegradability of the scaffold in an in vivo environment, the fabricated scaffold was washed three times or more using a 70% EtOH solution and distilled water, and then subcutaneously injected into Balb/c mice (female, 6-week-old, Charles River Laboratories, South Korea). In addition, morphological changes over time were observed, and the result is shown in FIG. 15. FIG. 18 shows (A) scanned electron microscope images of hyaluronic acid/collagen cryogel scaffolds fabricated by mixing with various ratios and crosslinking and (B) the degradation behavior of a 5:5 blend scaffold under an in vivo condition (subcutaneous implantation into mouse).

Example 3

Fabrication of Cryogel Scaffold Consisting of Collagen/Poly-Gamma Glutamic Acid

Figure 16:
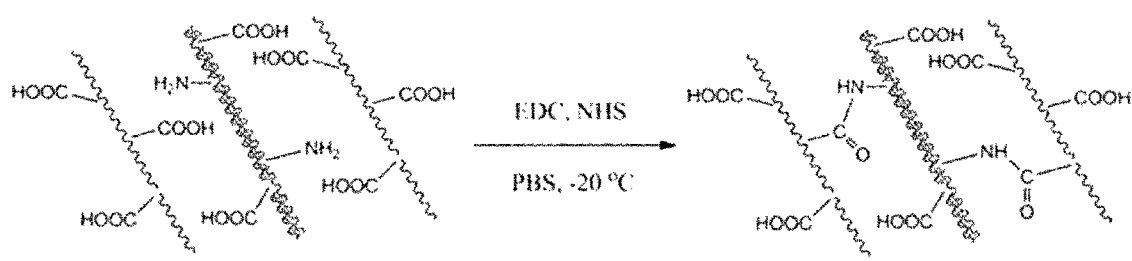
FIG. 16 illustrates a chemical crosslinking reaction for fabricating a cryogel scaffold containing collagen and poly(gamma-glutamic acid).
Figure 19:
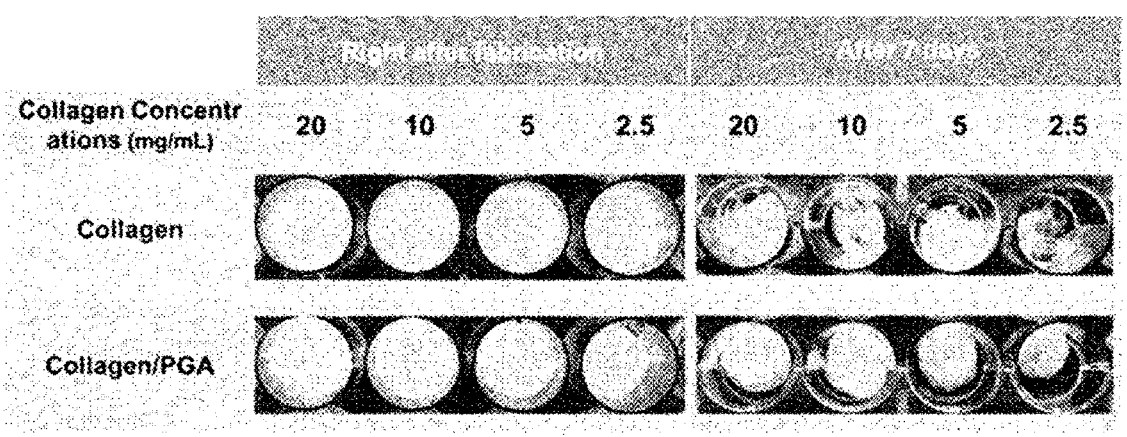
FIG. 19 is a set of images showing the degradation behavior of collagen/poly(gamma-glutamic acid) blend-based cryogel scaffolds formed by crosslinking reactions between collagen solutions with various concentrations and poly(gamma-glutamic acid) under an in vitro condition (collagenase).

Collagen (type I, Bioland, Cheonan, South Korea) was dissolved in sterile PBS at 10 mg/mL (overnight at 4° C.). Poly(gamma-glutamic acid)(PGA, 500 kDa, Bioleaders, Daejeon, South Korea) was dissolved in sterile PBS at a concentration of 10 mg/mL, and the collagen and the poly (gamma-glutamic acid) were mixed at various volume ratios, and stirred using a magnetic stirrer at 4° C. and 500 rpm for 12 hours. 250 μL of the mixed solution (scaffold solution) was put into a PDMS mold, frozen for 9 hours at −20° C., and then freeze-dried for 12 hours. The sample was immersed in 2 mL of an ethanol solution containing 50 mM EDC/20 mM NHS for 12 hours at −20° C., washed with DI for 15 minutes five times, and freeze-dried for 12 hours, thereby fabricating a cryogel scaffold consisting of collagen/poly(gamma-glutamic acid) (FIG. 16). To measure biodegradability of the scaffold in an in vitro environment, the fabricated scaffold was immersed in collagenase, and a change of degradability was observed over time. The result is shown in FIG. 19.

Example 4

Figure 20:
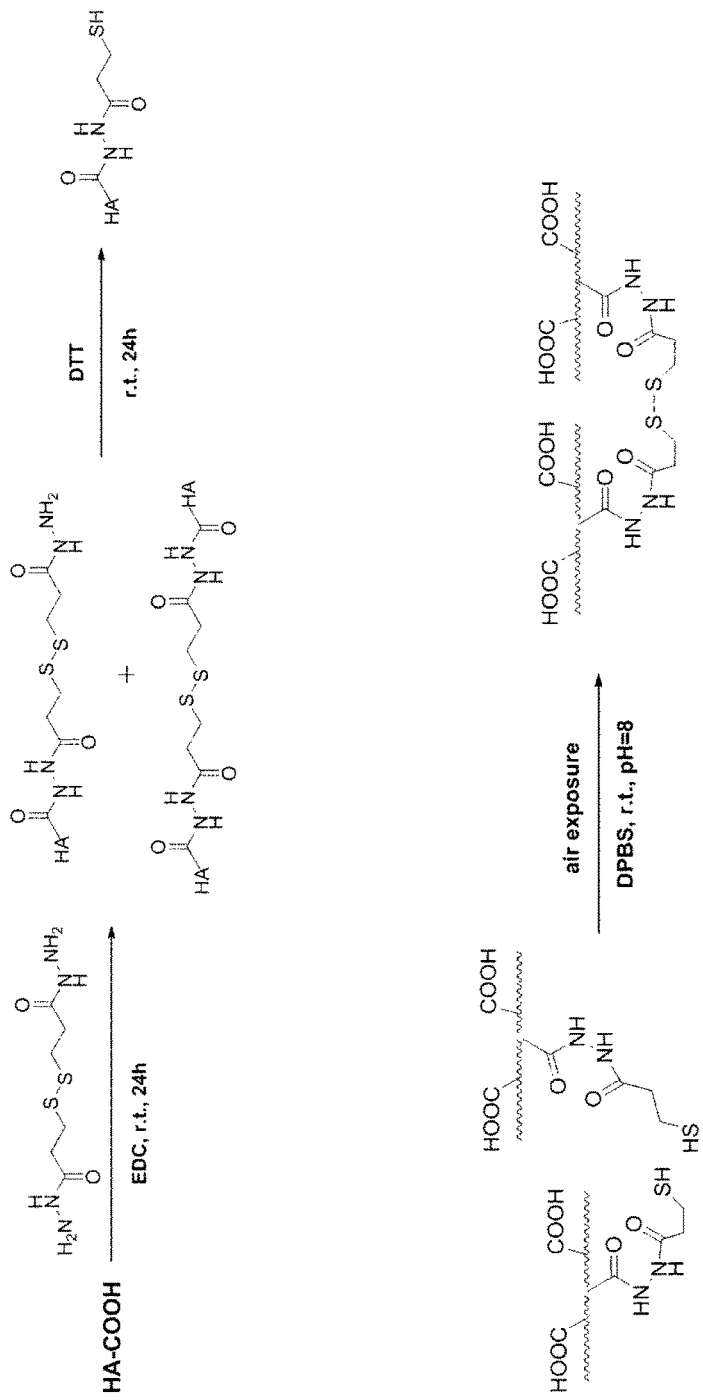
FIG. 20 illustrates a chemical crosslinking reaction for fabricating a thiolated HA-based cryogel scaffold.

Fabrication of Thiolated HA-Based Cryogel Scaffold 20.0 g of HA was dissolved in 2 L of water, and 23.8 g of 3,3'-dithiobis(propanoic hydrazide) (DTP) was added while stirring the HA solution. Subsequently, pH was adjusted to 4.75 using 1.0N HCl, 19.2 g of EDC was added, and then the pH was adjusted to 4.75 using 1.0N HCl. Afterward, the pH was increased to 7.0 using 1.0N NaOH to terminate the reaction. In addition, 100 g of DTT (ca. 650 mmol; Diagnostic Chemicals Limited, Oxford, USA) was added, and the pH was increased to 8.5 using 1.0N NaOH, followed by stirring for 24 hours. Subsequently, 1.0N HCl was added to adjust the pH to 3.5, and the solution was transferred to dialysis tubing (Mw cutoff 3500), and dialyzed against low concentration HCl (pH=3.5, approximately 0.3 mM) containing 100 mM NaCl. Afterward, the resulting dialysate was dialyzed against low concentration HCl (pH=3.5) and centrifuged, and then the supernatant was freeze-dried. HA-DTPH was dissolved in DPBS at 3.0% (w/v), and the pH was adjusted to 8 using 1.0N NaOH. A gel prepared by reacting the mixture was reacted in a PDMS mold cooled to −20° C. for 18 hours was heated to room temperature to remove ice, thereby fabricating a scaffold. The fabricated scaffold was washed three times with PBS and 70% ethanol (FIG. 20).

Example 5

Adjustment of Degradability of Cryogel Scaffold by ROS Generation

Figure 8:
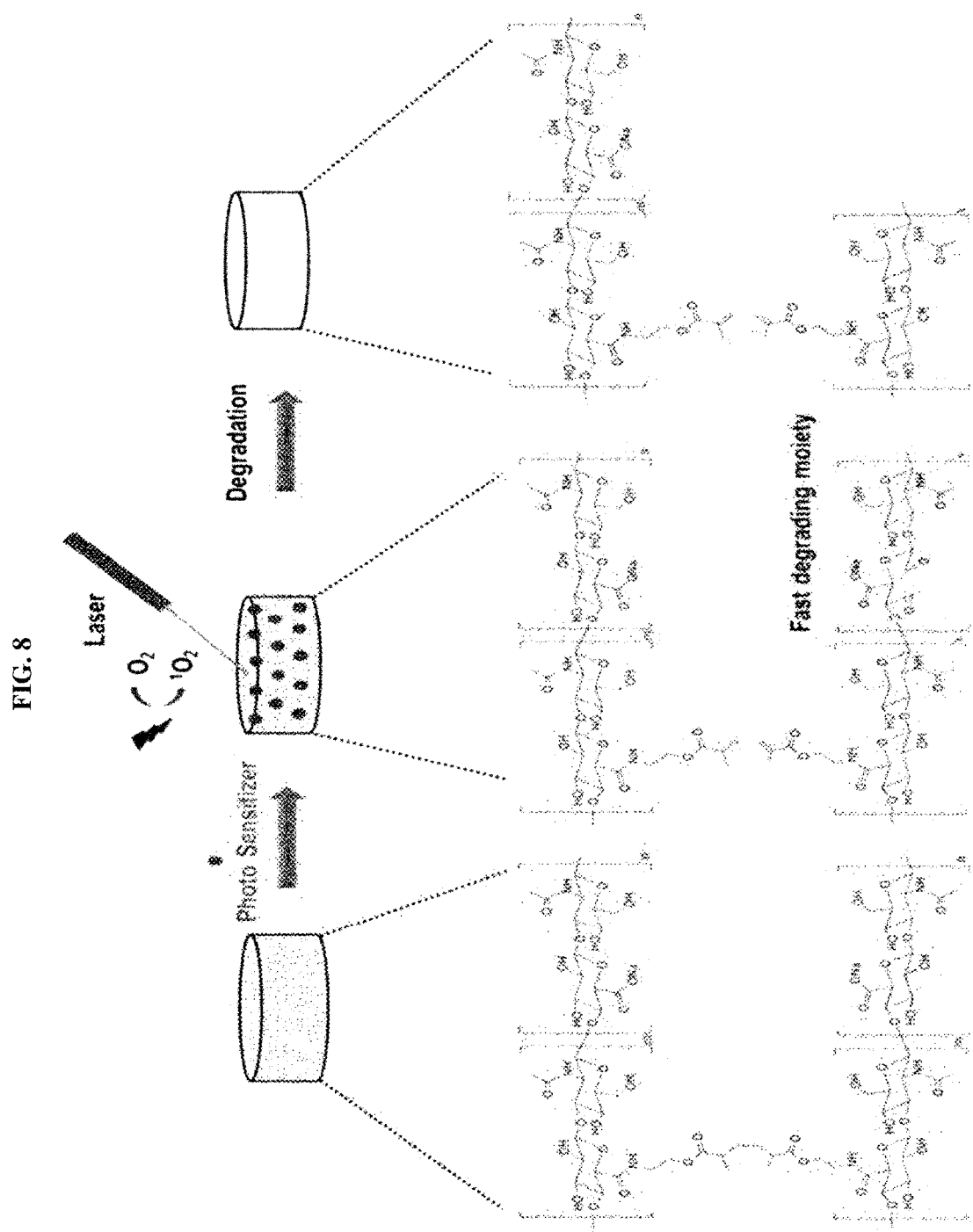
FIG. 8 illustrates a cryogel scaffold capable of adjusting degradability by ROS generation and adjustment of degradability thereof.

To measure the degradability of a cryogel scaffold by ROS generation through light illumination (FIG. 8), a photosensitizer (20 μg, Ce6) was loaded into the fabricated scaffold, 650-nm laser was applied, and then a weight change of the scaffold was measured every three days while the scaffold was stirred at 60 rpm and 37° C.

Example 6

Adjustment of Degradability of Cryogel Scaffold by Reduction

Figure 9:
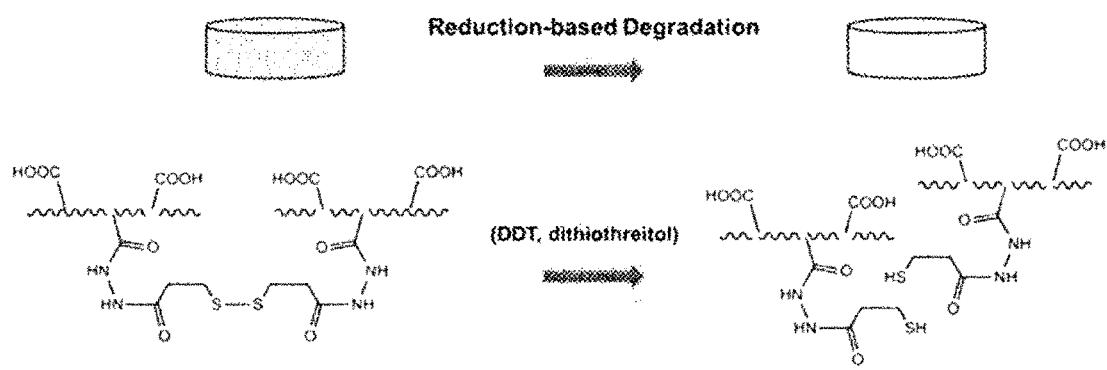
FIG. 9 illustrates a cryogel scaffold capable of adjusting degradability by a reductant (DTT) and adjustment of degradability thereof.

To measure the degradability of a cryogel scaffold by reduction (FIG. 9), the scaffold including a disulfide bond was treated with dithiothreitol (DDT), and then its weight change was measured every three days.

Example 7

Adjustment of Degradability of Cryogel Scaffold by Enzyme

Figure 10:
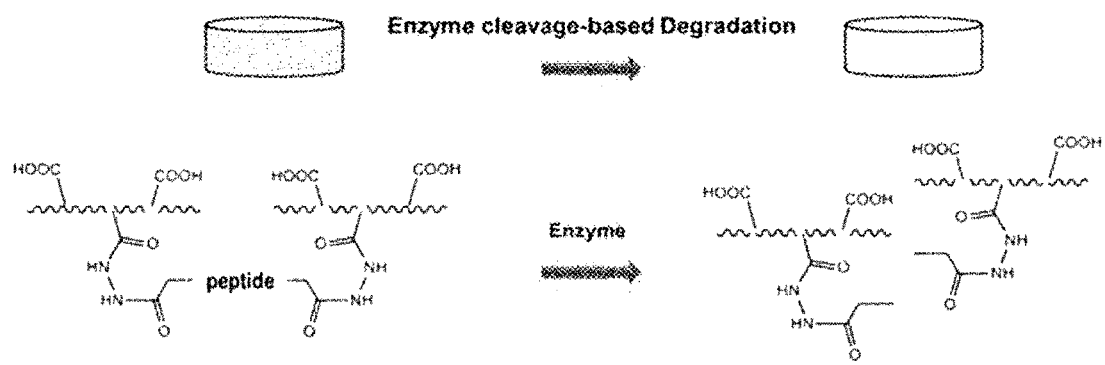
FIG. 10 illustrates a cryogel scaffold capable of adjusting degradability by an enzyme and adjustment of degradability thereof.

To measure the degradability of a cryogel scaffold by an enzyme (FIG. 10), the scaffold including an enzyme-cleavable peptide bond was treated with an enzyme, and then its weight change was measured every three days.

Example 8

Figure 1B:
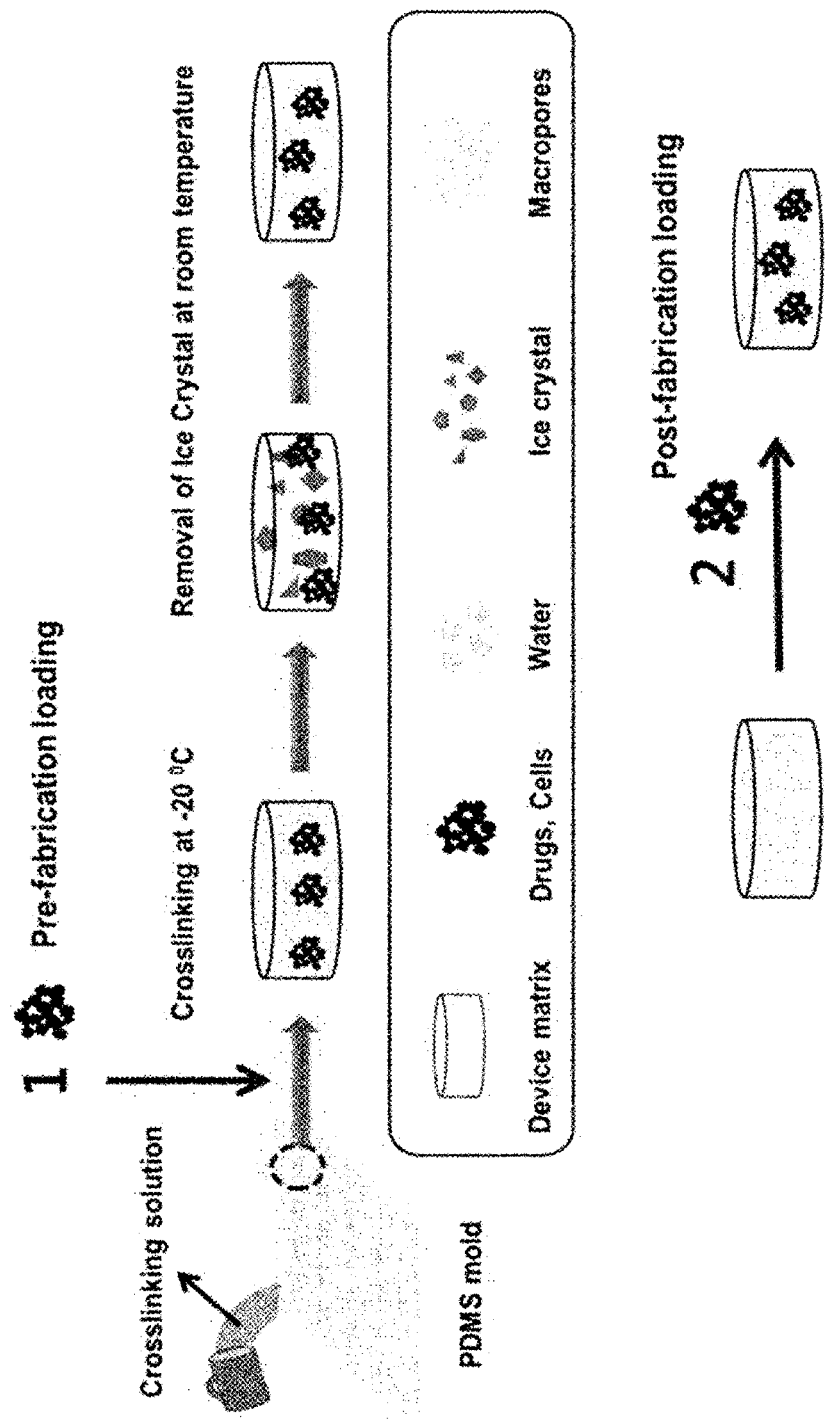
FIG. 1B illustrates a process of fabricating a soft bio-integrated device in which a drug is loaded into a cryogel scaffold.
Figure 21:
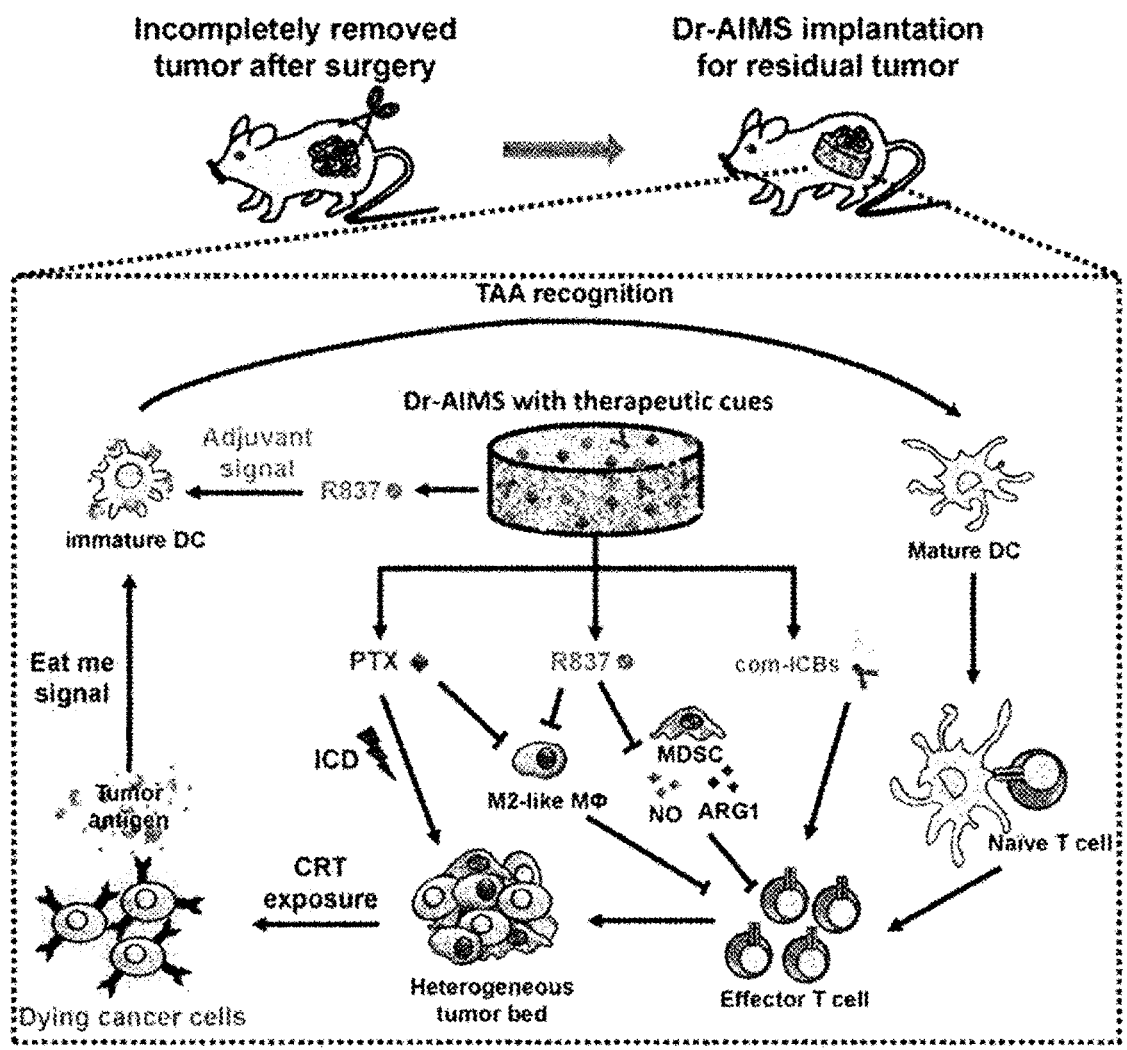
FIG. 21 illustrates the function of a soft bio-integrated device including a drug for inhibiting an immunosuppressive factor (immune checkpoint inhibitor), an immune-activating antibody, an anticancer agent and an immune-activating drug, which are inserted into the body.
Figure 22:
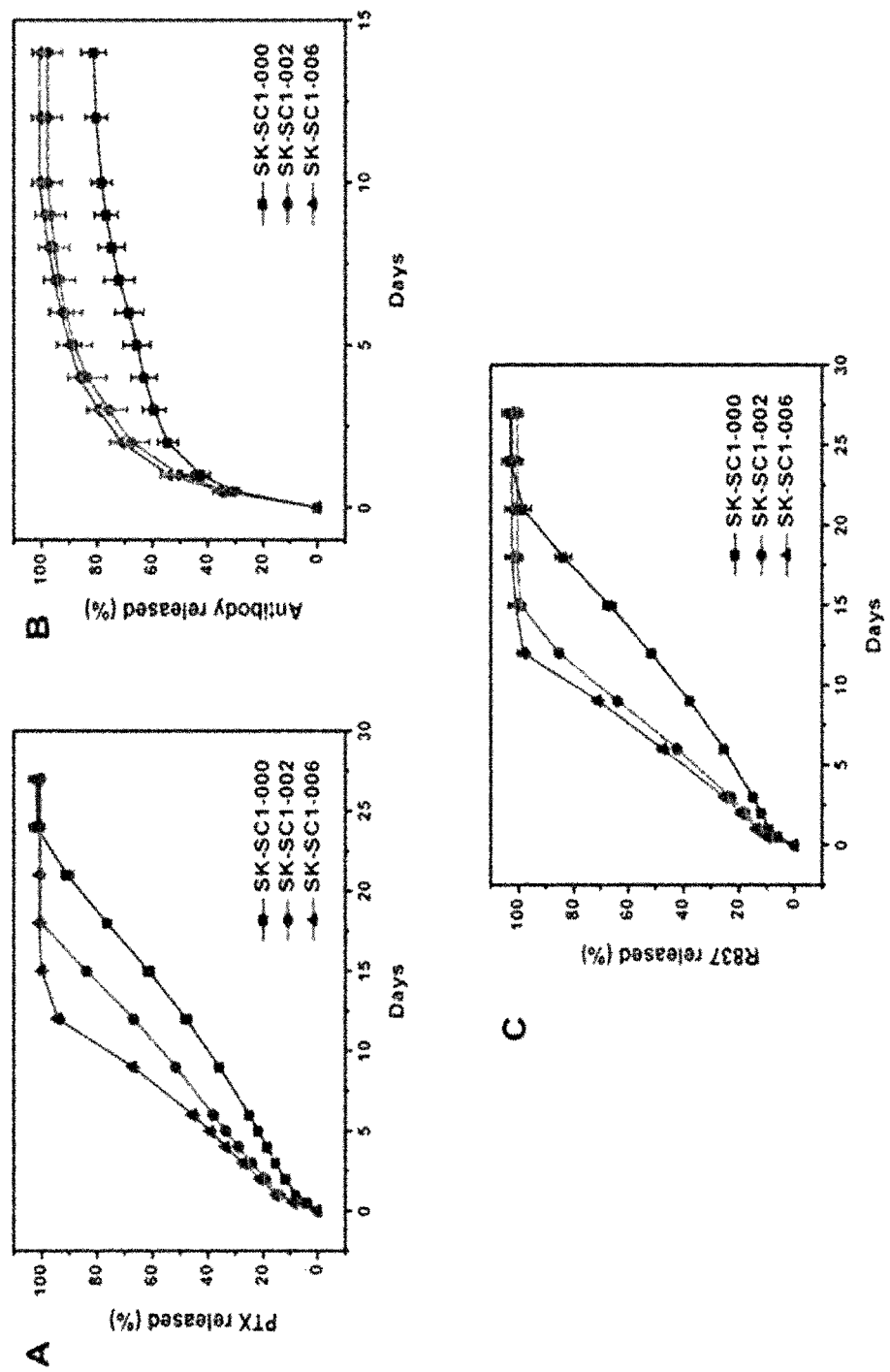
FIG. 22 is a set of graphs showing the release behavior of PTX (A), an antibody (anti-CTLA4) (B) and R837 (C), loaded into soft bio-integrated devices, which include cryogel scaffolds based on HA-MA/HA-ald-MA blend(s) with various mixing ratios.

Fabrication of Soft Bio-Integrated Device Including Immunosuppressive Factor-Controlling Drug (Immune Checkpoint Inhibitor), Immune Activating Antibody, Anticancer Agent and Immune-Activating Drug In this example, a soft bio-integrated device including R837 and selectively including PTX and/or Abs was fabricated to confirm the release behavior of each drug and the degradability thereof by an enzyme. Specifically, in the process of fabricating the HA-MA/HA-ald-MA scaffold in Example 1-4, an anticancer agent such as paclitaxel (PTX) and a toll-like receptor 7 agonist such as imiquimod (R837) serving to convert an M2 macrophage having an immunosuppressive function into an M1 macrophage were mixed in a mixed solution, followed by crosslinking. Anti-CTLA4 that can control an immunosuppressive checkpoint and an immune-activating antibody such as anti-OX40 were loaded into the crosslinking-completed scaffold, thereby fabricating a soft bio-integrated device (FIGS. 1B and 21). FIG. 14 shows the degradation behavior of the soft bio-integrated devices fabricated with various composition ratios (hyaluronic acid-methacrylate (HA-MA): hyaluronic acid-aldehyde methacrylate (HA-ald-MA)) by 10 U/mL HAdase. FIG. 22 shows the release behavior of PTX, antibodies (anti-CTLA4) and R837 loaded into the soft bio-integrated devices fabricated with various composition ratios (hyaluronic acid-methacrylate (HA-MA): hyaluronic acid-aldehyde methacrylate (HA-ald-MA)).

Example 9

Verification of Regulation of Immunosuppressive Factor and Anticancer Effect by Soft Bio-Integrated Device In this example, the regulation of an immunosuppressive factor and an anticancer effect were verified through cellular and animal experiments using soft bio-integrated devices (SK-SC1-002) in which PTX, antibodies (anti-CTLA4 and anti-OX40) and R837 were loaded.

9-1. Preparation and Culture of Cells

A dendritic cell line (DC 2.4), a macrophage cell line (Raw 264.7), a breast cancer cell line (4T1), and mouse bone marrow-derived dendritic cells (BMDCs) were used in in vitro experiments. The macrophage cell line (Raw 264.7) was cultured in DMEM supplemented with 10% FBS and a 1% antibiotic-antifungal agent, and the breast cancer cell line (4T1) and the dendritic cell line (DC 2.4) were cultured in RPMI1640 supplemented with 10% FBS and a 1% antibiotic-antifungal agent under 5% carbon dioxide at 37° C. The mouse BMDCs were isolated from the bone marrow, and differentiated under 5% carbon dioxide at 37° C. by adding 20 ng/mL GM-CSF to RPMI1640 supplemented with 10% FBS and a 1% antibiotic-antifungal agent solution.

9-2. Confirmation of Cytotoxicity of PTX and R837

MTS analysis is a method used to measure a cytotoxic effect of a drug by comparing cell viability. $1 \times 10^4$ cells were seeded in each well of a 96-well plate (Corning Costar, USA) and suspended in 100 uL of a medium. Drugs were dispersed in the cell culture medium at various concentrations (0.1 to 100 μg), and each well was treated with 100 uL each of the dispersed drugs, and then the cells were incubated under 5% carbon dioxide at 37° C. for 24 and 48 hours. After cell culture, 20 uL of a Cell Titer 96 Aqueous One Solution was added to each well, and the cells were incubated for 2 hours, followed by measuring absorbance at 490 nm using VersaMax (Molecular Devices, USA).

9-3. Activation and Maturation of BMDCs 1 mL of $1 \times 10^6$ mouse BMDCs differentiated by the method described in Example 9-1 was dispensed in each well in a 12-well plate (Corning Costar, USA). After treatment of each drug-loaded soft bio-integrated device, the cells were incubated under 5% carbon dioxide at 37° C. for 24 hours. Subsequently, a culture supernatant was collected by centrifugation, and then a cytokine present in the supernatant was analyzed using an ELISA kit (BD Biosciences, USA). To confirm a marker for mature mouse BMDCs, cells were collected, treated with fluorescence-conjugated antibodies CD40, CD80 and MHC2 (eBioscience, USA), and then incubated for 1 hour at 4° C. Each sample was washed with PBS twice, and then fixed with 4% paraformaldehyde. The prepared samples were analyzed using an Accuri™ flow cytometer (BD Biosciences, USA). The result is shown in FIG. 23.

Figure 23:
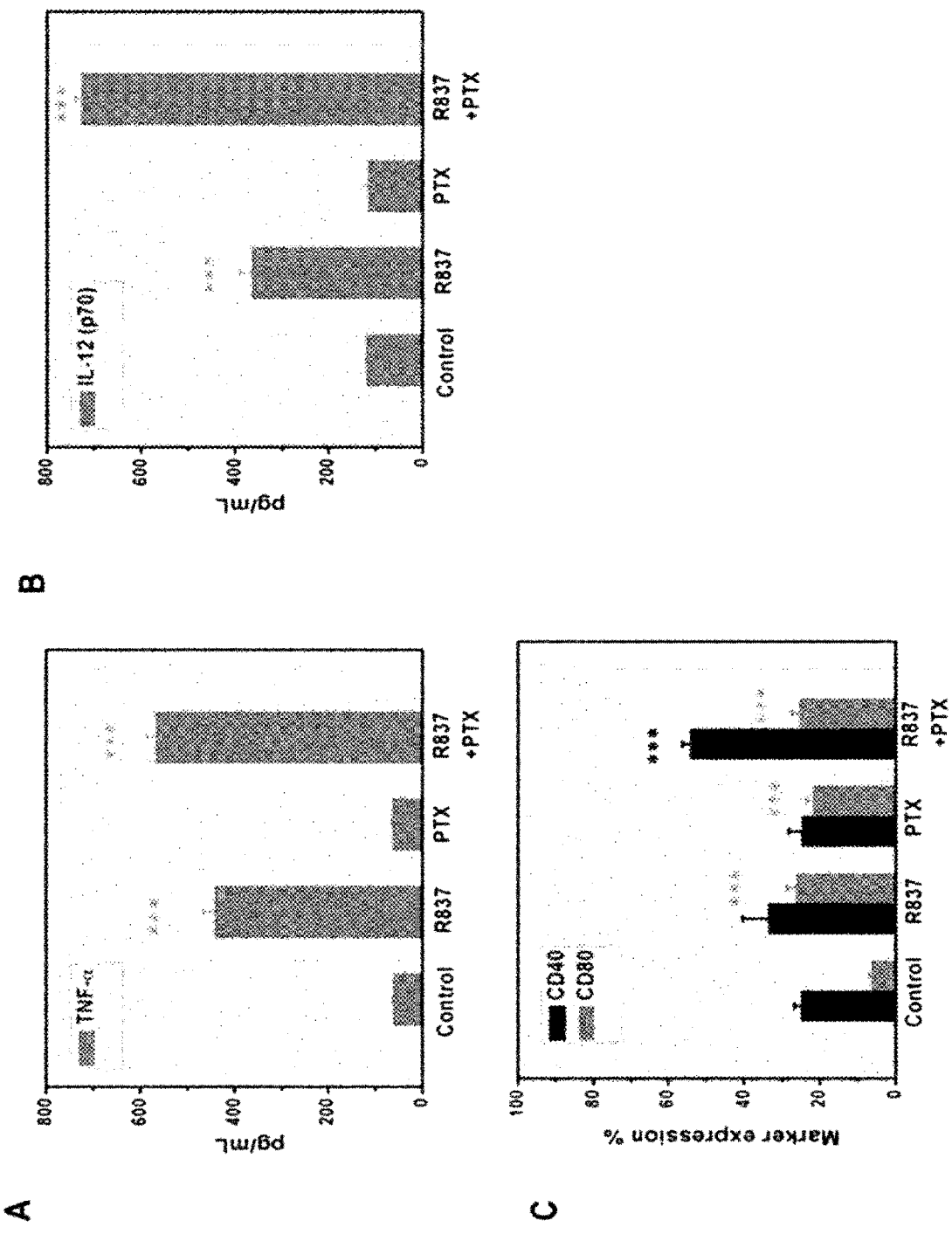
FIG. 23 is a set of graphs confirming activation effects of BMDC by soft bio-integrated devices (SK-SC1-002) in which PTX and an antibody (anti-CTLA4) and/or R837 are loaded.

As shown in FIG. 23, when activation effects of the mouse BMDCs by soft bio-integrated devices (SK-SC1-002) in which PTX, antibodies (anti-CTLA4 and anti-OX40) and/or R837 were loaded were verified, it can be confirmed that expression levels of TNF-α (A), IL-12 (p70) (B), CD40 and CD80 (C) increased the most in a group co-treated with PTX and R837.

9-4. Production of Breast Cancer Animal Models

Balb/c mice (female, 6-8 week-old) were maintained under a specific pathogen-free condition. Animal experiments were approved by the Institutional Animal Care and use Committee (IACUC) of the School of Medicine at Sungkyunkwan University, and followed the guidelines of the Association for Assessment and Accreditation of Laboratory Animal Care International (AAALAC International). For in vivo experiments, Balb/c mice were anesthetized by injection with 200 uL of a 2.5% Avertin solution (2,2,2-tribromoethanol, Sigma-Aldrich). $1 \times 10^6$ cells of the breast cancer cell line (4T1) were injected into the subcutaneous layer on the right flank of the anesthetized Balb/c mice, and a scaffold was implanted by surgery conducted when the cancer size became approximately 200 mm$^3$.

9-5. Flow Cytometry

Cancer and the spleen were isolated from the mouse produced in Example 9-4 and formed into single cells, and then antibodies were stained. Specifically, cancer tissue was sectioned using scissors, dissolved in RPMI1640, and treated with 1 mg/mL of collagenase D (Sigma-Aldrich, South Korea), followed by incubating the tissue at 80 rpm and 37° C. for 1 hour. Subsequently, undissolved tissue was removed using a nylon mesh, thereby obtaining cancer cells. Spleen cells were obtained by grinding the tissue using a grinder, separating the tissue fragments using a nylon mesh, and performing centrifugation. Subsequently, the obtained cancer cells and spleen cells were added to a red blood cell (RBC) lysis buffer, incubated at 37° C. for 10 minutes, and treated with the cell culture medium twice as much as the treated RBC lysis buffer to inactivate the RBC lysis buffer. The cells were washed with PBS twice, labeled with specific fluorescence-conjugated antibodies, and then fixed with 4% paraformaldehyde. The prepared cell samples were analyzed using an Accuri™ flow cytometer (BD Biosciences, USA).

Figure 24:
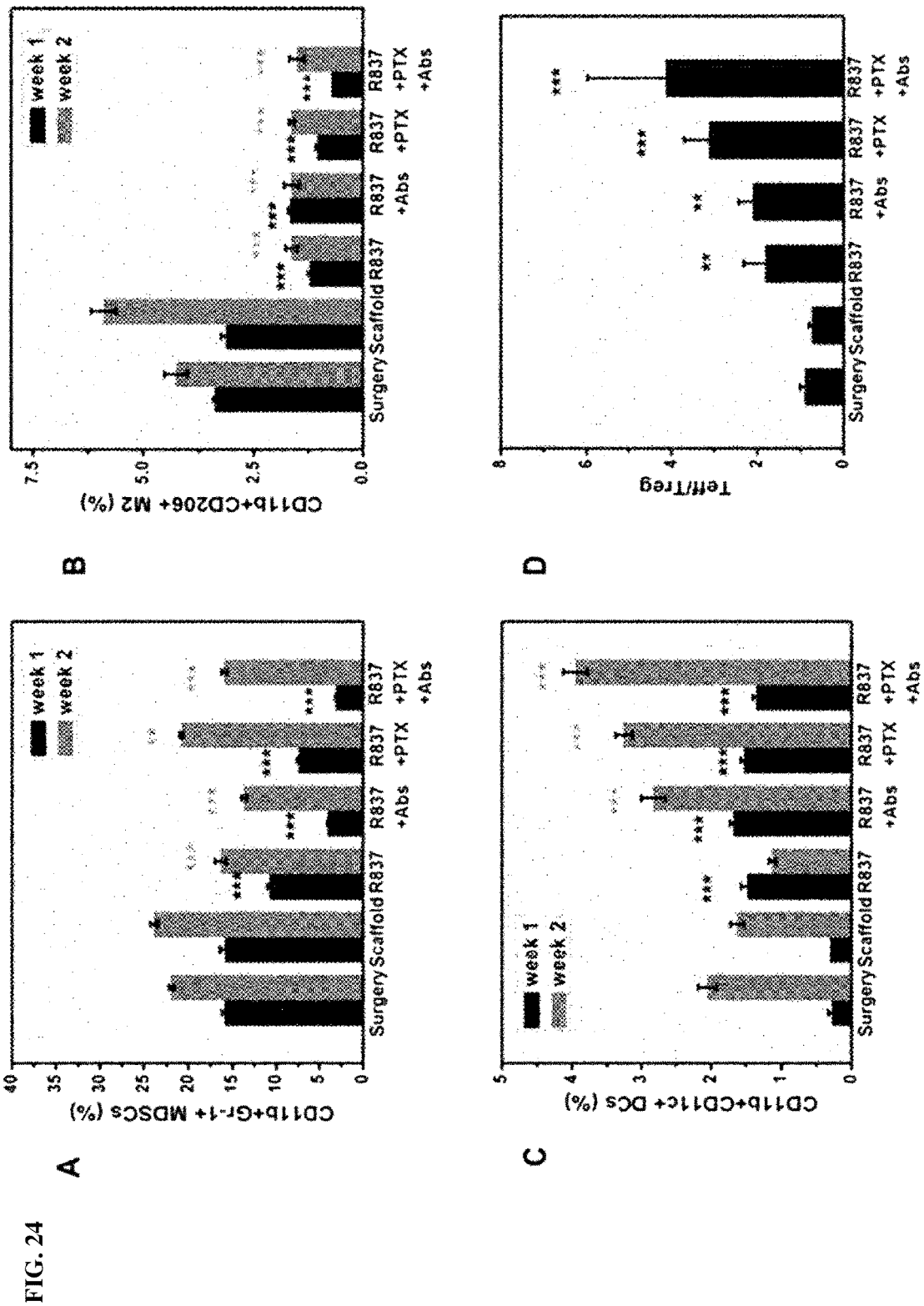
FIG. 24 is a set of graphs confirming the distribution of immunosuppressive cells and immune-activating cells in a solid tumor microenvironment after soft bio-integrated devices (SK-SC1-002) in which PTX and/or antibodies (anti-CTLA4 and anti-OX40) and R837 are loaded are implanted into breast cancer animal models.

As a result, after the PTX, antibodies (anti-CTLA4, anti-OX40) and R837-loaded soft bio-integrated devices (SK-SC1-002) were implanted into breast cancer models, it can be confirmed that, in a PTX+R837+Abs group (FIGS. 24A and 24B), near solid tumors, immunosuppressive cells such as MDSCs and M2 cells are significantly reduced, and immune-activating cells such as DCs and effector T cells increased (FIGS. 24C and 24D).

Figure 25:
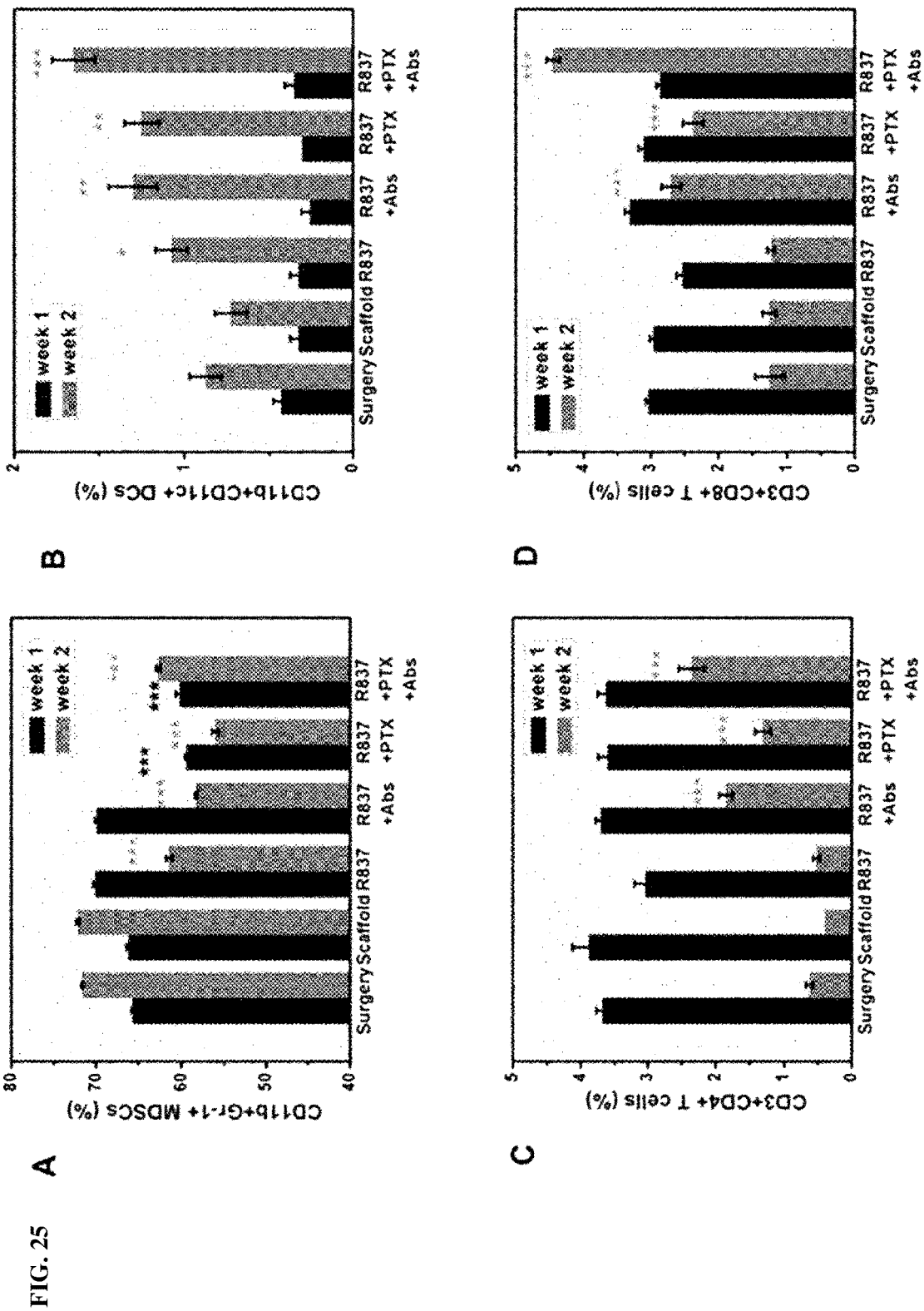
FIG. 25 is a set of graphs confirming the distribution of immunosuppressive cells and immune-activating cells in the spleen after soft bio-integrated devices (SK-SC1-002) in which PTX and/or antibodies (anti-CTLA4 and anti-OX40) and R837 are loaded are implanted into breast cancer animal models.

In addition, in the spleens of animal models in which the PTX, antibodies (anti-CTLA4 and anti-OX40) and R837-loaded soft bio-integrated devices (SK-SC1-002) were implanted into breast cancer models, it can also be confirmed that, in a PTX+R837+Abs group, immunosuppressive cells such as MDSCs were significantly reduced (FIG. 25A) and immune-activating cells such as DCs, CD4+ and CD8+ T cells were increased (FIGS. 25B, 25C and 25D).

Figure 26:
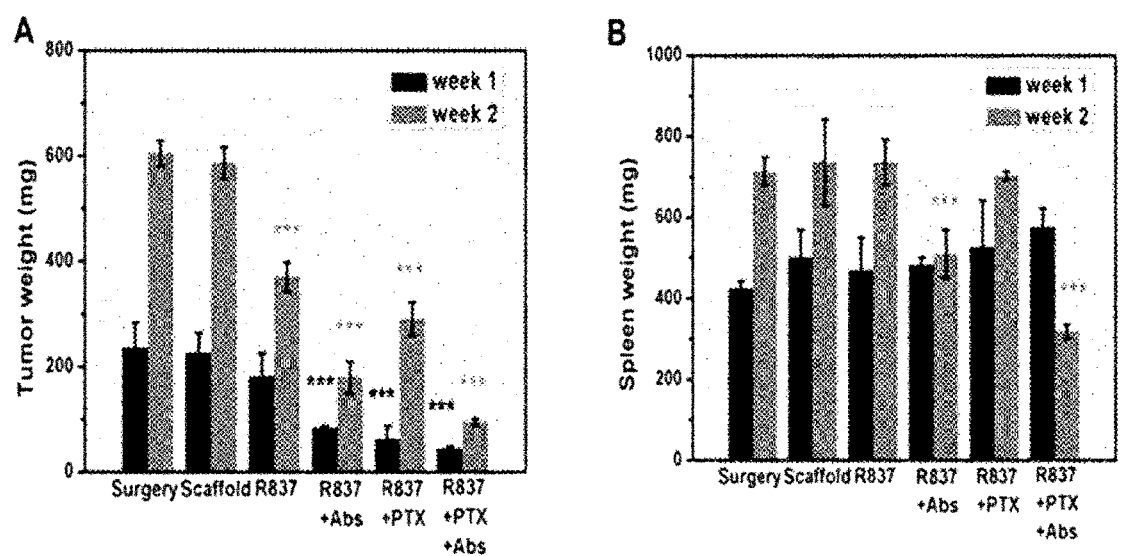
FIG. 26 is a set of graphs confirming weights of a solid tumor (A) and the spleen (B), measured 1 and 2 weeks after soft bio-integrated devices (SK-SC1-002) in which PTX and/or antibodies (anti-CTLA4 and anti-OX40) and R837 are loaded are implanted into breast cancer animal models.

In addition, when weights of solid tumors and spleens were measured one week and two weeks after PTX, antibodies (anti-CTLA4 and anti-OX40) and R837-loaded soft bio-integrated devices (SK-SC1-002) were implanted into breast cancer models, it was also confirmed that the smallest weights are shown in a PTX+R837+Abs group, and thus the most excellent cancer therapeutic effect is exhibited (FIG. 26).

Figure 27:
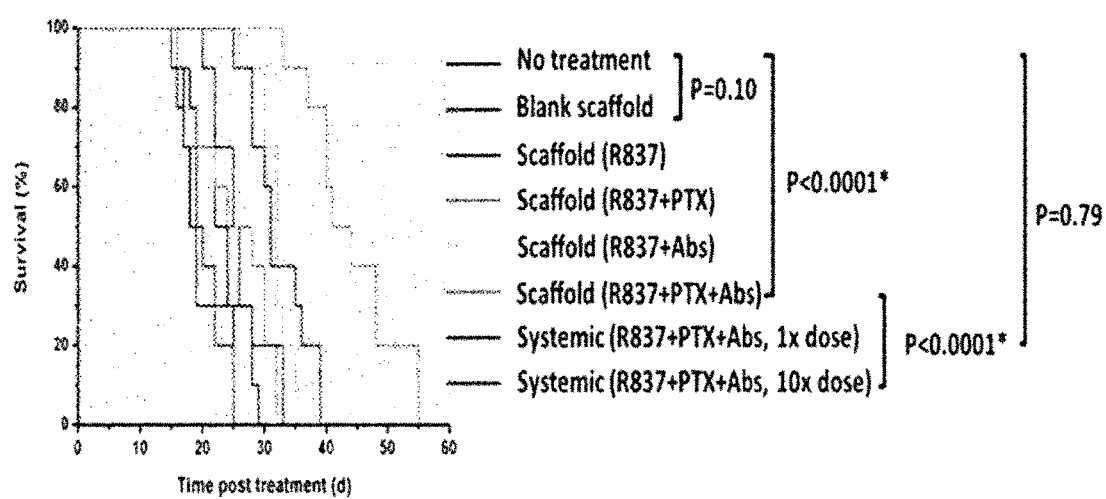
FIG. 27 is a graph confirming survival rates after soft bio-integrated devices (SK-SC1-002) in which PTX and/or antibodies (anti-CTLA4 and anti-OX40) and R837 are loaded are implanted into breast cancer animal models.

In addition, when survival rates were measured after the PTX, antibodies (anti-CTLA4 and anti-OX40) and R837-loaded soft bio-integrated devices (SK-SC1-002) were implanted into breast cancer models, it can be confirmed that the highest survival rate was exhibited in the soft bio-integrated device group including PTX+R837+Abs (FIG. 27).

9-6. Statistical Analysis

The difference between groups was analyzed by ANOVA, and average values were compared by the Student's t-test. Significance is indicated by P<0.05, <0.01 or <0.001. Animal survival rates were compared by the log-rank test using GraphPad Prism 5.0 (GraphPad Software, USA).

Example 10

Figure 28:
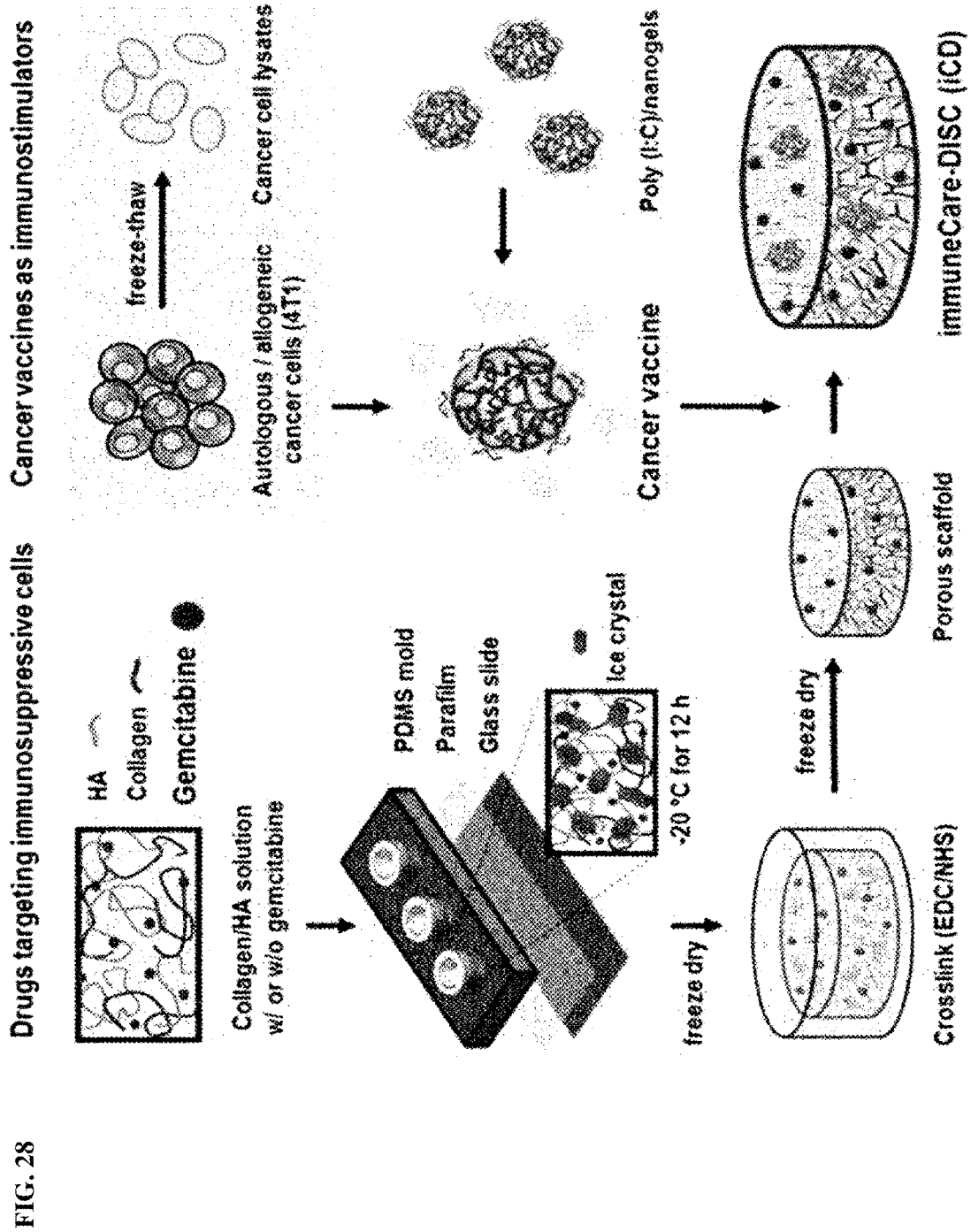
FIG. 28 illustrates a process of fabricating soft bio-integrated devices (immuneCare-DISC) in which an MDSC death-inducing drug, a cancer vaccine and an immunoactivator are loaded.

Fabrication of Soft Bio-Integrated Devices in which a Drug for Removing Immunosuppressive Cells (MDSCs), Cancer Antigen and Immune-Activating Adjuvant were Loaded In the process of fabricating a hyaluronic acid/collagen scaffold as described in Example 2, a drug for removing immunosuppressive cells (MDSCs), such as gemcitabine (GEM), was mixed with the mixed solution and then crosslinking was performed, thereby fabricating a soft bio-integrated device including GEM. Soft bio-integrated devices including GEM, a cancer vaccine and an immunoadjuvant were fabricated by further loading cancer cell lysates and an immunosuppressive adjuvant (immunoadjuvant, poly(I:C)-loaded nanogel) into the soft bio-integrated device obtained by freeze-drying (FIG. 28).

Example 11

Method of Evaluating Cancer Therapeutic Effects of Soft Bio-Integrated Devices in which a Drug for Removing Immunosuppressive Cells (MDSCs), Cancer Antigen and Immune-Activating Adjuvant were Loaded 11-1. Mice and Cell Lines BALB/c mice (6-week-old, female) were purchased from Orient Bio (Sungnam, Korea), and maintained under pathogen-free conditions. Animal experiments were approved by the Institutional Animal Care and use Committee (IACUC) of the School of Medicine at Sungkyunkwan University, and followed the guidelines of the Association for Assessment and Accreditation of Laboratory Animal Care International (AAALAC International). A 4T1 breast cancer cell line was cultured in RPMI medium containing 10% FBS (Thermo Scientific), $5 \times 10^5$ M 2-mercaptoethanol (Sigma-Aldrich), 50 IU/mL penicillin and 50 μg/mL streptomycin (Thermo Scientific).

11-2. Fabrication of Gemcitabine-Loaded Soft Bio-Integrated Device and Measurement of Gemcitabine Loading Efficiency In the process of fabricating a hyaluronic acid/collagen scaffold as described in Example 2, gemcitabine (2 mg/scaffold) was uniformly mixed with a collagen-hyaluronic acid mixed solution and crosslinked at a low temperature, thereby fabricating a gemcitabine-loaded soft bio-integrated device. Subsequently, the loading efficiency of gemcitabine according to the ratio of hyaluronic acid and collagen was measured.

11-3. Fabrication of Soft Bio-Integrated Device in which 4T1 Cell Lysate and Poly(I:C)/Nanogel were Loaded To obtain a 4T1 cell lysate, $1 \times 10^7$ 4T1 cells/mL were rapidly frozen using liquid nitrogen and then thawed at 37° C., which was repeated five times, and the resulting product was centrifuged at 490×g for 10 minutes to obtain a supernatant of the cell lysate. A protein concentration was analyzed using BCA assay (Pierce Biotechnology). Six hours before implantation into a space from which a tumor was removed, 500 µg of the cell lysate was uniformly dropped on a scaffold and stored at 4° C., thereby fabricating a 4T1 cell lysate-loaded soft bio-integrated device. Subsequently, to load poly(I:C)/nanogel into the scaffold, first, a nanogel solution was uniformly dropped into a poly(I:C) solution, and the mixed solution was reacted for 2 hours. The ratio was a weight ratio of 1:2 (nanogel:poly(I:C)). The poly(I:C)/nanogel (100 µg of poly(I:C)) was uniformly dropped on the 4T1 cell lysate-loaded soft bio-integrated device and stored at 4° C. for 6 hours, thereby fabricating a soft bio-integrated device in which the 4T1 cell lysate and the poly(I:C)/nanogel were loaded.

11-4. Confirmation of In Vitro Drug Release Behavior of Soft Bio-Integrated Device A scaffold in which gemcitabine, rhodamine-attached poly(I:C)/nanogel, and a 4T1 cell lysate were loaded was added to 1 mL of PBS (pH 7.4), and stored at 37° C. and 90 rpm. Every selected time interval, the original culture medium was obtained and exchanged with a fresh medium. An amount of gemcitabine released from the scaffold was measured using absorbance (275 nm, UV-1800; Shimadzu, Kyoto, Japan), the rhodamine-attached poly(I:C) was measured according to the protocol of the 5'EneTag™ Nucleic Acid Labeling System (Vector Laboratories), and the 4T1 cell lysate was measured using the BCA assay method (Pierce Biotechnology). Specifically, a fluorescence spectrometer (PerkinElmer) was used to detect and analyze fluorescence at 552 nm (excitation) and 575 nm (emission) from the poly(I:C)/nanogel attached to rhodamine released from the scaffold.

11-5. Acquisition of BMDCs and Confirmation of Activation of Dendritic Cells using Poly(I:C)/nanogel and 4T1 Lysate Muscle tissue was carefully removed after collecting the shin and femur of a mouse, and the obtained bones were immersed and sterilized in 70% ethanol for 1 minute and then washed with PBS. Both ends of each bone were cut, and then the bone marrow was washed with an RPMI medium using a 26 G needle syringe. After centrifugation at 490×g for 5 minutes, bone marrow cells were obtained by removing RBCs using an RBC lysis buffer. The obtained bone marrow cells were cultured in a 100-mm Petri dish containing an RPMI medium supplemented with FBS, penicillin, streptomycin and a granulocyte macrophage colony-stimulating factor (GM-CSF; R&D Systems), and after 7 days, the cultured BMDCs were used in an experiment.

The BMDCs, at a density of $2\times10^6$ cells/well, were incubated with poly(I:C)/nanogel (10 µg/mL of poly(I:C)) and a 4T1 cell lysate in a 6-well plate. After 24 hours, a supernatant was obtained, and IL-6 and TNF-α were detected using ELISA (BD Biosciences). Subsequently, a BMDC activation marker was analyzed using an Accuri™ flow cytometer. Antibodies used herein were FITC-anti-CD11b, PE-anti-CD11c, APC-anti-CD40, and APC-anti-CD80 (BD Pharmingen).

11-6. Confirmation of In Vitro Gemcitabine Effect

Gemcitabine induces apoptosis of myeloid-derived-suppressor cells (MDSCs) in vitro. The spleen was extracted from a mouse harboring 4T1 tumors for 28 days, the extracted spleen was ground, and RBCs were removed therefrom using an RBC lysis buffer. The RBC-removed spleen cells were re-dispersed in a MACS buffer (PBS, 0.5% BSA, 2 mM MEDTA), MDSCs were isolated using an MDSC isolation kit (Miltenyi Biotec). The isolated myeloid-derived-suppressor cells were seeded in a 6-well plate at a density of $2\times10^6$ cells/well, and incubated with various concentrations of gemcitabine. The gemcitabine-induced apoptosis of the MDSCs was assessed according to the protocol of an FITC Annexin V Apoptosis kit (BD Biosciences).

In addition, the activation of BMDCs using a gemcitabine-treated 4T1 breast cancer cell line was confirmed. The 4T1 cells were cultured with 1 µg/mL gemcitabine in a 6-well plate at a density of $2\times10^6$ cells/well. The gemcitabine-induced apoptosis of the 4T1 breast cancer cells was assessed according to the protocol of the FITC Annexin V Apoptosis kit (BD Biosciences). After 24 hours, a supernatant was collected, and then incubated with BMDCs. A BMDC activation marker was analyzed using an Accuri™ flow cytometer. Antibodies used herein were FITC-anti-CD11c and APC-anti-CD80 (BD Pharmingen).

11-7. Procedure for Implanting Soft Bio-Integrated Device

When $1\times10^6$ 4T1 cells were injected and the size of a growing tumor became 300 mm$^3$ on day 14 after injection, the tumor was partially resected. A mouse was anesthetized using 2,2,2-tribromoethanol. The surgical site was sterilized with 70% ethanol, and 90% of the tumor was resected so that 10% of the tumor remained. A scaffold was implanted near the remaining part of the tumor.

11-8. Confirmation of In Vivo Effect caused by Implantation of Soft Bio-Integrated Device To confirm the maturation of dendritic cells by a soft bio-integrated device, a drug-free scaffold or a scaffold in which poly(I:C)/nanogel and a 4T1 lysate were loaded was implanted into the side of a BALB/c mouse. The scaffold was isolated on day 7 and day 14 after implantation, and the isolated scaffold was degraded at 37° C. for 1 hour using collagenase D (Worthington), thereby obtaining cells. The obtained cells were filtered using a 70-µm strainer (BD Biosciences) and washed with PBS. Dendritic cell markers such as CD86 and CD11c antibodies were used, and analyzed using an Accuri™ flow cytometer.

Subsequently, to confirm a change in secretion patterns of cytokines and chemokines by a soft bio-integrated device, IL-12, IL-6 and CCL-2 concentrations in scaffold-implanted sites were measured. Specifically, peripheral tissue (100 mg) of the scaffold-implanted site was resected, and homogenized using 1 mL of a protein extraction buffer containing a protease inhibitor. The cytokines and the chemokines were measured by ELISA according to the manufacturer's protocol.

Afterward, to confirm dendritic cells migration to a lymph node by a soft bio-integrated device, a scaffold in which rhodamine-attached poly(I:C)/nanogel and an FITC lysate were loaded was implanted into the side of a mouse, and after 3 days and 7 days, cells were obtained by isolating an inguinal lymph node of the mouse and degrading the lymph node using collagenase D, and then filtered through a 70-µm strainer. And then, dendritic cells having FITC and rhodamine fluorescent signals were analyzed using a flow cytometer.

11-9. Confirmation of In Vivo Anticancer Effect by Implantation of Soft Bio-Integrated Device On day 7 and day 14 after tumor removal and implantation of a soft bio-integrated device, a mouse was sacrificed, and a tumor, the spleen and a lymph node of the sacrificed mouse were isolated to measure weights thereof.

The tumor and lymph node were cut into small pieces, dispersed in DMEM containing collagenase D, stored for 1 hour at 37° C. and 90 rpm, and then filtered through a 70-µm strainer. The spleen was physically disrupted, and then RBCs were removed using an RBC lysis buffer. The tumor and spleen dispersed as single cells by the above-described method were analyzed using APC-anti-CD11b and PE-anti-Gr1 antibodies to confirm myeloid-derived-suppressor cells and using APC-anti-CD3, PE-anti-CD4 and FITC-CD8 antibodies to confirm T cells. All antibodies were purchased from BD Pharmingen.

In addition, to measure an anticancer response ex vivo, the spleen and the lymph node were dispersed as single cells by the above-described method, cultured in a 12-well plate at a density of $2\times10^6$ cells/mL, and activated using 80 μg/mL of a 4T1 lysate. After 72 hours, a supernatant was collected, and IFN-γ (BD Biosciences) was measured by ELISA.

Figure 29:
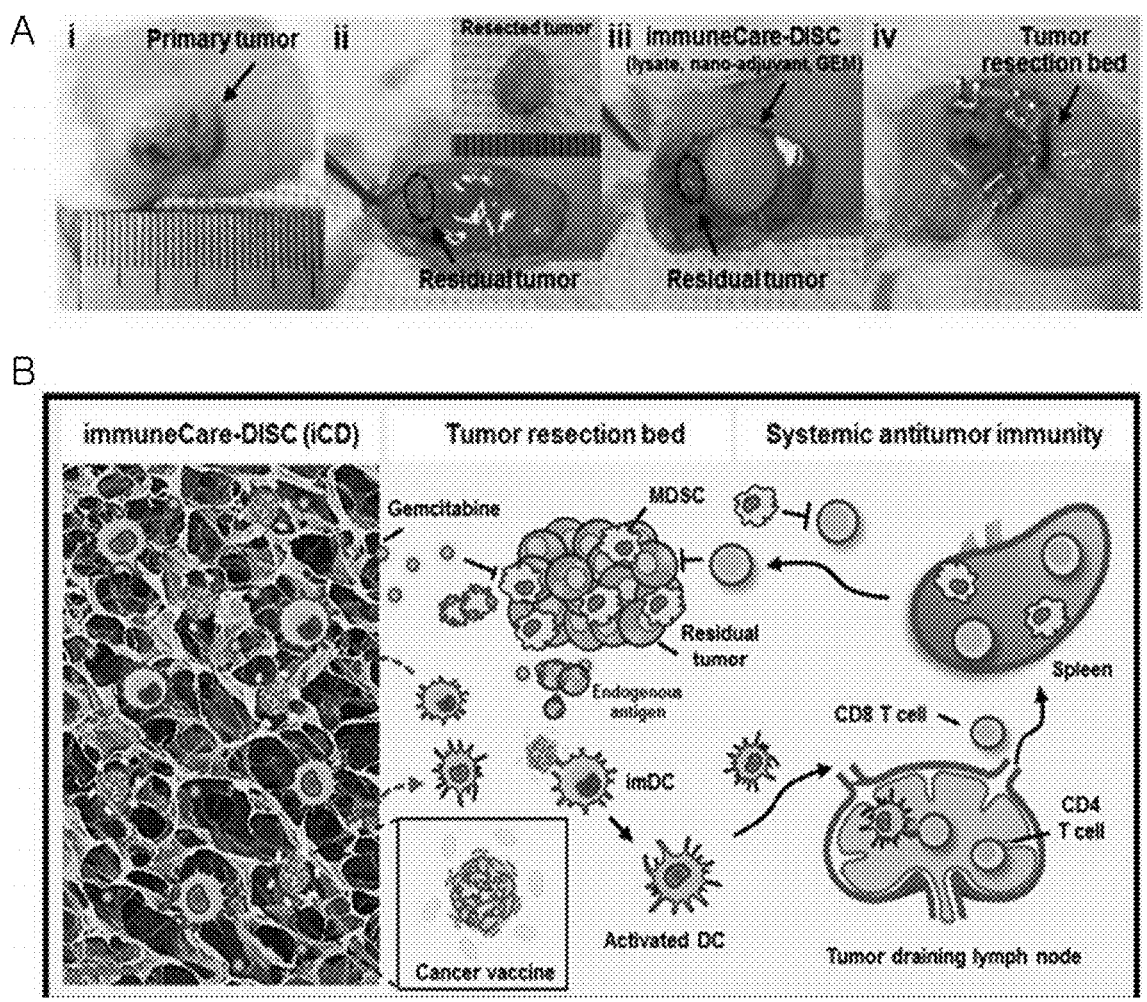
FIG. 29 is (A) a set of images showing a process of implanting soft bio-integrated devices in which an MDSC death-inducing drug, a cancer vaccine and an immunoactivator are loaded into breast cancer animal models and (B) a concept map of the control of an immunosuppressive environment and the induction of anticancer and immunotherapeutic effects using soft bio-integrated devices in which drugs are loaded. Among the images showing the process of implanting soft bio-integrated devices into breast cancer animal models, i) represents a tumor before resection on day 14 after tumor cells are implanted, and having a size of approximately 300 mm$^3$, ii) represents a resected tumor (approximately 90% of the entire tumor) after tumor resection and the remaining tumor in the body, iii) represents a soft bio-integrated device implanted into the tumor-resected site, and iv) represents the suture of a surgical wound after a soft bio-integrated device is implanted.

Moreover, to confirm tumor metastasis, on day 14 after the tumor removal, the mouse was sacrificed to confirm metastasis. The metastasis of cancer cells was confirmed using a method of bronchially injecting a 3 mL Indian ink. Specifically, the lungs were extracted and immersed in a Fekete solution (100 mL of 70% ethanol, 10 mL of 4% formaldehyde, and 5 mL of 100% acetic acid) for destaining 11-10. Verification of Results FIG. 29 shows images and a concept map illustrating the control of an immunosuppressive environment and the induction of an anticancer immune effect using a soft bio-integrated device in which a MDSC-controlling drug, a cancer antigen and an immunoactivator are loaded near a solid tumor. FIG. 29A illustrates a process of implanting a fabricated soft bio-integrated device into a breast cancer model (4T1). FIG. 29B illustrates a process of inducing a systemic anticancer effect exhibited through a lymph node and the spleen by controlling immunosuppressive cells, i.e., MDSCs, near a solid tumor into which gemcitabine (GEM) and a cancer vaccine released from an implanted soft bio-integrated device were implanted and activating antigen-presenting cells such as dendritic cells.

Figure 30:
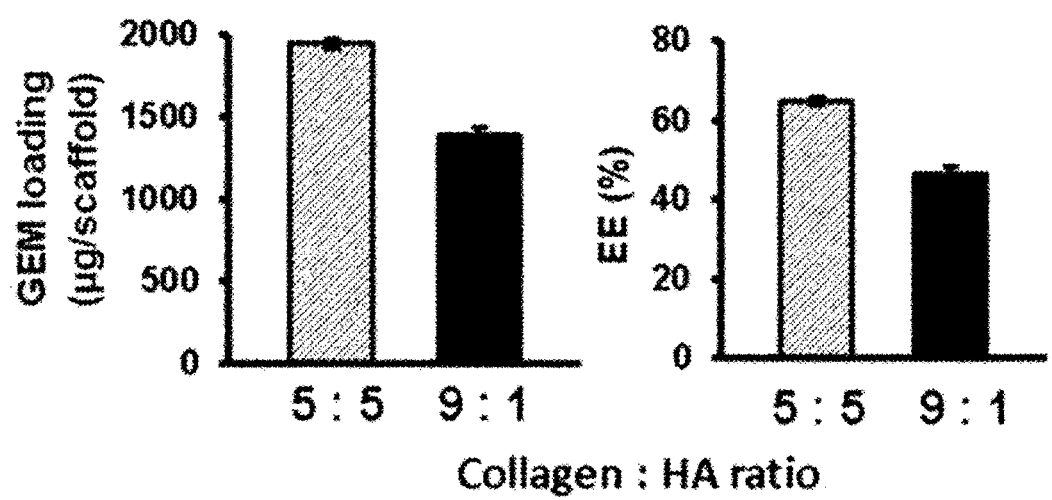
FIG. 30 is a set of graphs confirming differences in gemcitabine loading efficiency and loading amounts of soft bio-integrated devices according to the mixing ratios of collagen and hyaluronic acid.

FIG. 30 shows differences in gemcitabine loading efficiency and loading amounts of soft bio-integrated devices according to the mixing ratios of collagen and hyaluronic acid. As shown in FIG. 30, it can be confirmed that a gemcitabine loading amount was highest in a cryogel scaffold in which collagen and hyaluronic acid were mixed at 5:5.

Figure 31:
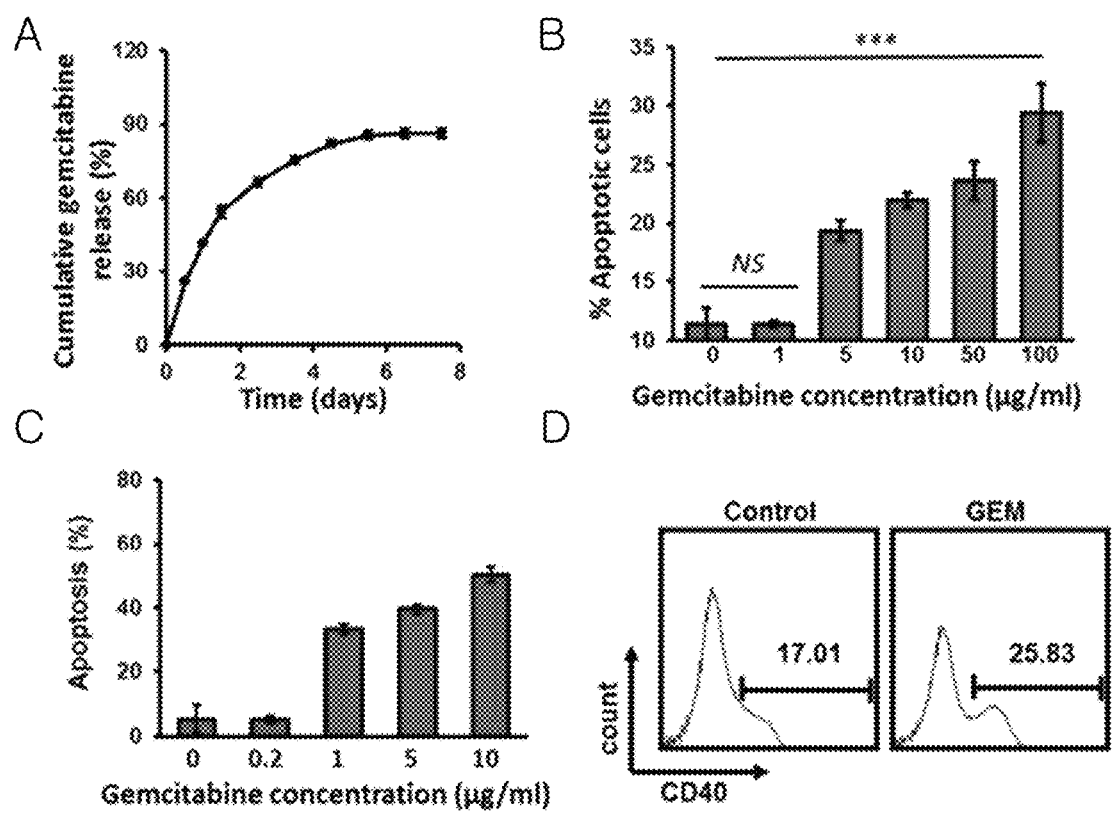
FIG. 31 is a set of graphs confirming the release behavior of gemcitabine released from a soft bio-integrated device and effects thereof on cancer cells and immune cells. A) shows cumulative gemcitabine released from a soft bio-integrated device for one week, B) shows a dead cell percentage of myeloid-derived-suppressor cells (MDSCs) according to a change in gemcitabine concentration, C) shows a dead cell percentage of a breast cancer cell line (4T1) according to a change in gemcitabine concentration, and D) shows flow cytometry results for comparing cell maturity of dendritic cells between a gemcitabine-treated breast cancer cell line (experimental group) and a control.

FIG. 31 shows the release behavior of gemcitabine released from a soft bio-integrated device and effects thereof on cancer cells and immune cells. As seen from FIG. 31A, according to the measurement of an accumulation amount of gemcitabine released from the scaffold for one week, approximately 90% of the gemcitabine was released from the scaffold within one week, and according to the result of measurement of a dead cell percentage of myeloid-derived-suppressor cells (MDSCs) according to a change in concentration of gemcitabine, a dead cell percentage increased as the gemcitabine concentration increased (FIG. 31B). In addition, as a result of measuring a dead cell percentage in a breast cancer cell line (4T1) according to the change in gemcitabine concentration, a dead cell percentage increased as the gemcitabine concentration increased (FIG. 31C). Subsequently, by flow cytometry for comparing cell maturity of dendritic cells in a breast cancer cell line (experimental group) treated with gemcitabine and a control, it can be confirmed that, in the experimental group, the cell maturity of the dendritic cells increased (FIG. 31D).

Figure 32:
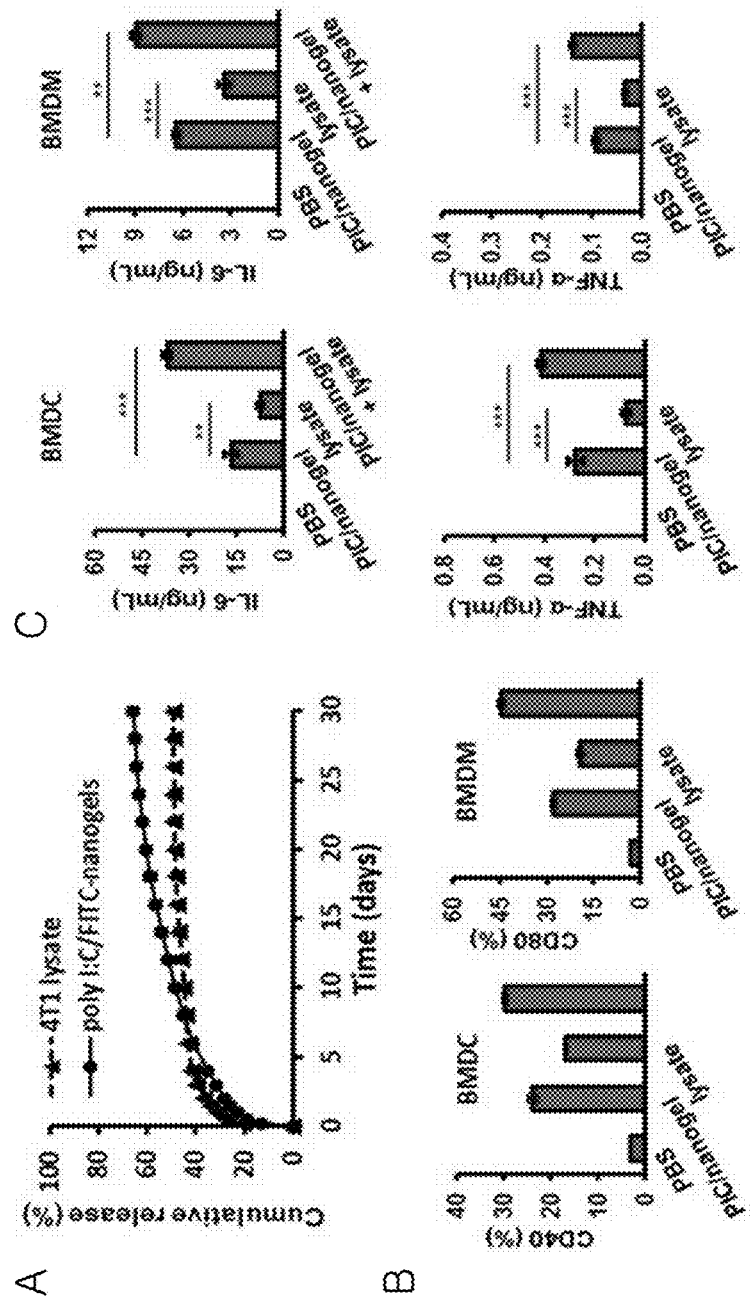
FIG. 32 is a set of graphs confirming the release behavior of a cancer vaccine released from a soft bio-integrated device and effects of activating immune cells (BMDCs and BMDMs). A) shows cumulative results of a breast cancer cell line lysate and poly I:C-nanogel, released from soft bio-integrated devices, B) shows flow cytometry results representing cell maturity (CD40 and CD80) of dendritic cells and macrophages after 24-hour incubation, and C) and D) shows results of measuring concentrations of cytokines (TNF-α and IL-6) released from dendritic cells and macrophages after 24-hour incubation.

FIG. 32 shows the release behavior of a cancer vaccine released from a soft bio-integrated device and effects of activating immune cells (BMDC and BMDM). As shown in FIG. 32, according to flow cytometry results representing cell maturity (CD40, CD80) of dendritic cells and macrophages after 24-hour incubation, it can be confirmed that, in an experimental group containing both of poly(I:C)-nanogel and a lysate, cell maturity increased due to a synergistic effect (FIG. 32B). In addition, as a result of measuring concentrations of cytokines (TNF-α, IL-6) released from dendritic cells and macrophages after 24-hour incubation, in an experimental group containing both of poly(I:C)-nanogel and a lysate, it can be confirmed that amounts of the secreted cytokines increased due to a synergistic effect (FIG. 32C).

Figure 33:
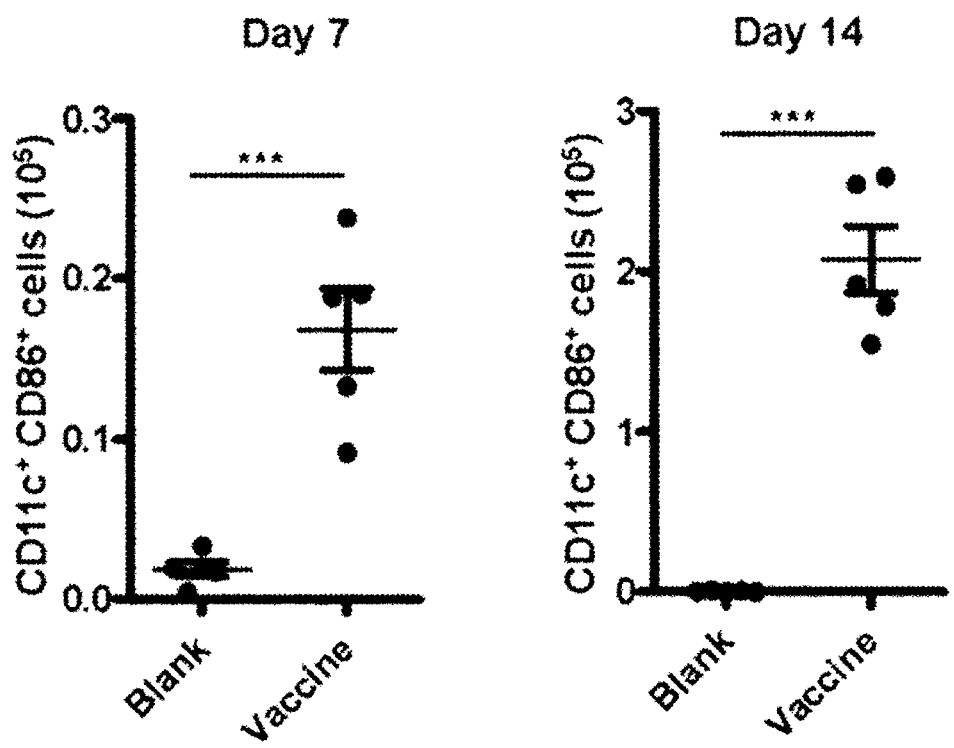
FIG. 33 is a set of graphs confirming cell maturity effects of dendritic cells over time by an in vivo implanted soft bio-integrated device. BLANK on the horizontal axis of the graph represents a soft bio-integrated device not containing a cancer antigen, and Vaccine represents a soft bio-integrated device containing a cancer antigen (poly(I:C)/nanogel(100 μg), 4T1 lysate(500 μg)) (n=5, *p<0.05, p<0.01, *p<0.005).

FIG. 33 shows cell maturity effects of dendritic cells over time by an in vivo implanted soft bio-integrated device, and it can be confirmed that an excellent effect of collecting and maturating dendritic cells was exhibited in a soft bio-integrated device containing a cancer antigen (vaccine) on day 7 and day 14.

Figure 34:
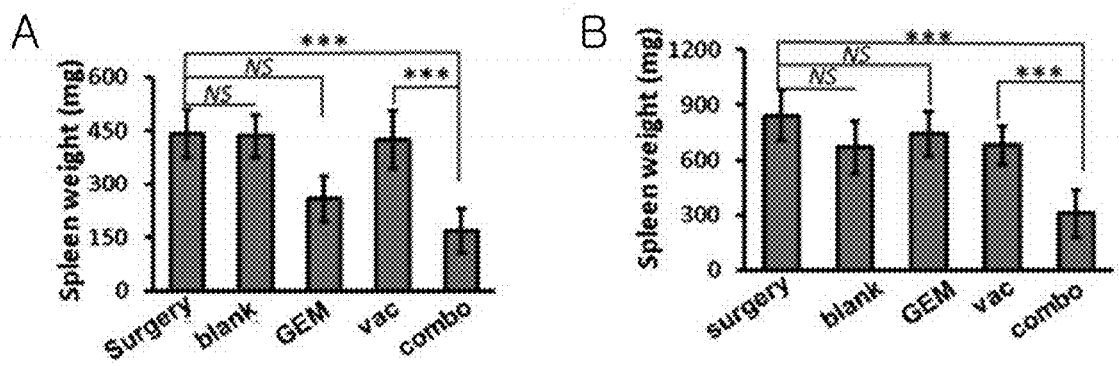
FIG. 34 shows results of comparing spleen weights on day 7 (A) and day 14 (B) after soft bio-integrated devices are implanted into breast cancer animal models (n=5, *p<0.05, p<0.01, *p<0.005).

In addition, as a result of comparing spleen weights on day 7 (A) and day 14 (B) after tumor resection and implantation of a soft bio-integrated device, it can be confirmed that, in an experimental group (combo) containing all of gemcitabine, poly(I:C)-nanogel and a cell lysate, synergistic immunity was exhibited and a spleen weight was not greatly increased (FIG. 34).

Figure 35:
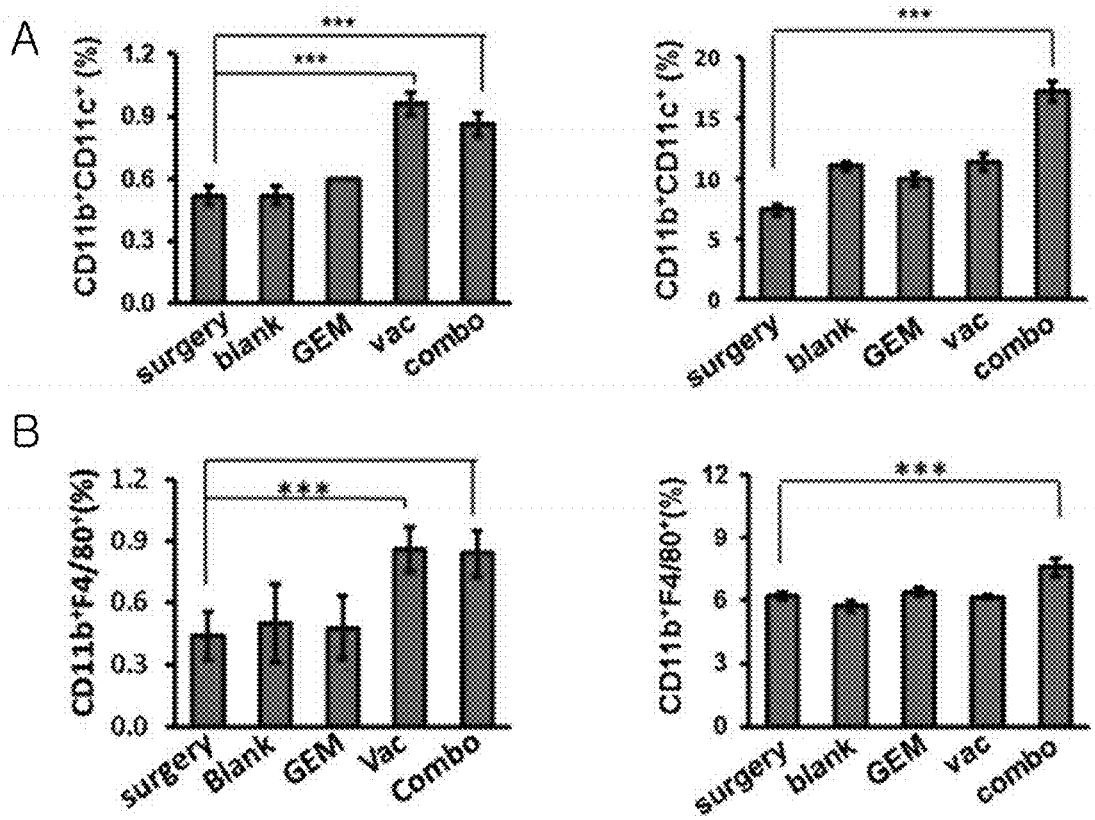
FIG. 35 shows results of comparing ratios of dendritic cells (A) and macrophages (B) in the tumor (red graph, left) and the spleen (blue graph, right) on day 14 after tumor resection and implantation of a soft bio-integrated device (n=5, *p<0.05, p<0.01, *p<0.005).

Subsequently, as a result of comparing proportions of dendritic cells (A) and macrophages (B) in the tumor and the spleen on day 7 and day 14 of the tumor resection and the implantation of a soft bio-integrated device, it can be confirmed that, in an experimental group containing all of gemcitabine, poly(I:C)-nanogel and a cell lysate and a vaccine-containing experimental group, proportions of dendritic cells and macrophages significantly increased (FIG. 35).

Figure 36:
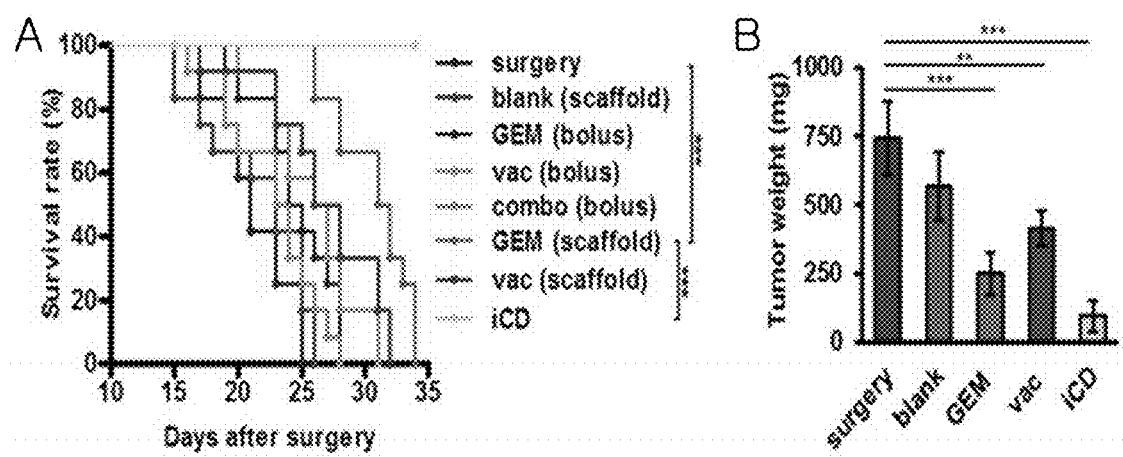
FIG. 36 shows (A) the result of a survival rate test after implantation of a soft bio-integrated device and (B) a result of comparing weights of recurring tumors (n=5, *p<0.05, p<0.01, *p<0.005).

Subsequently, as a result (A) of a viability test after the implantation of a soft bio-integrated device and a result (B) of comparing weights of recurring tumors on day 7 and day 14, it can be confirmed that, in an experimental group of a soft bio-integrated device (iCD) containing all of gemcitabine, poly(I:C)-nanogel and a cell lysate, the highest survival rate and the smallest weight of a solid tumor were exhibited (FIG. 36).

Figure 37:
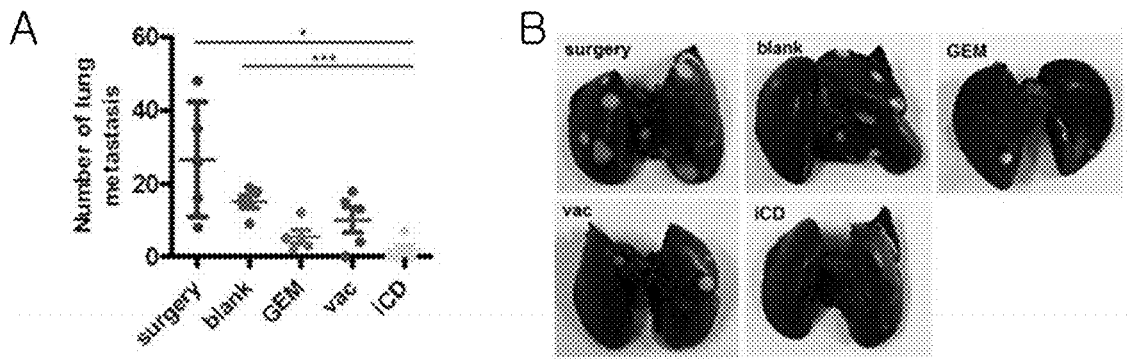
FIG. 37 shows the confirmation of an effect of preventing lung metastasis of cancer cells after implantation of a soft bio-integrated device. A) is a graph of comparing the number of metastatic lung tumor nodules (n=5, *p<0.05, p<0.01, *p<0.005), and B) is a set of images of lungs having tumors that have metastasized to the lungs.

Subsequently, as a result of observing an effect of preventing the lung metastasis of cancer cells after the implantation of a soft bio-integrated device, it can be confirmed that, in an experimental group of an soft bio-integrated device (iCD) containing all of gemcitabine, poly(I:C)-nanogel and a cell lysate, the number of tumor nodules that have metastasized to the lungs was smallest (FIG. 37).

Figure 38:
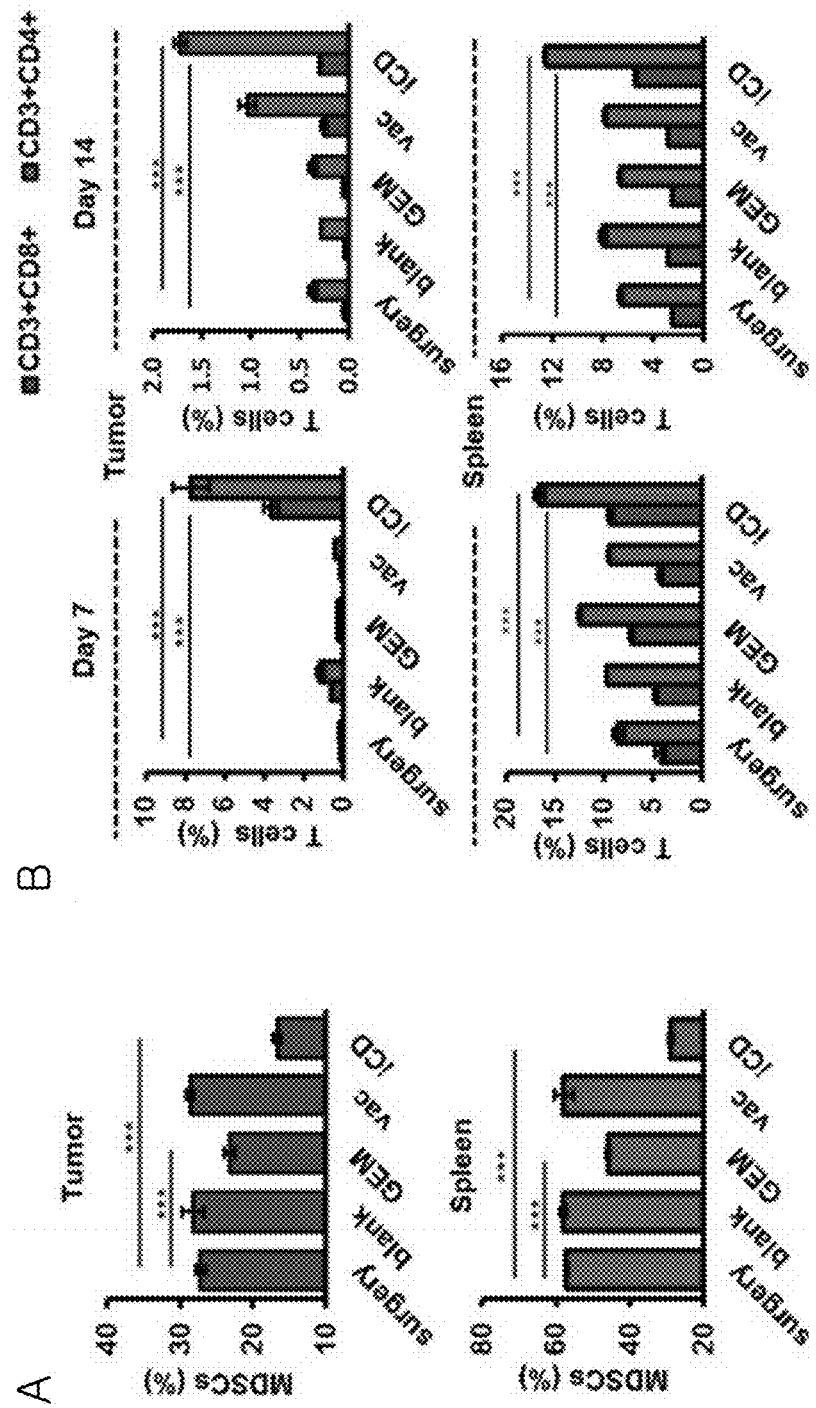
FIG. 38 is (A) a set of graphs confirming a change in proportion of myeloid-derived-suppressor cells (MDSCs) measured in a tumor (blue graph) and the spleen (red graph) after tumor resection and implantation of soft bio-integrated device and (B) a set of graphs confirming changes in proportions of CD8+ T cells and CD4+ T cells.

In addition, as seen from the change in proportion of MDSCs (FIG. 38A) and the proportions of CD8+ T cells and CD4+ T cells (FIG. 38B), measured in the tumor and the spleen on day 7 and day 14 after the tumor resection and the implantation of a soft bio-integrated device, it can be confirmed that, in an experimental group of a soft bio-integrated device containing all of gemcitabine, poly(I:C)-nanogel and a cell lysate, the MDSC proportion was significantly reduced. In addition, since gemcitabine has a function of killing MDSCs, it can be confirmed that, in a gemcitabine-treated experimental group, the MDSC proportion was reduced (FIG. 38A). In addition, from the CD8+ T and CD4+ T cell proportions measured in the tumor and the spleen on day 7 and day 14 after the tumor resection and the implantation of a scaffold, in an experimental group of a soft bio-integrated device containing all of gemcitabine, poly(I:C)-nanogel and a cell lysate, it can be confirmed that the T cell proportions increased (FIG. 38B).

Figure 39:
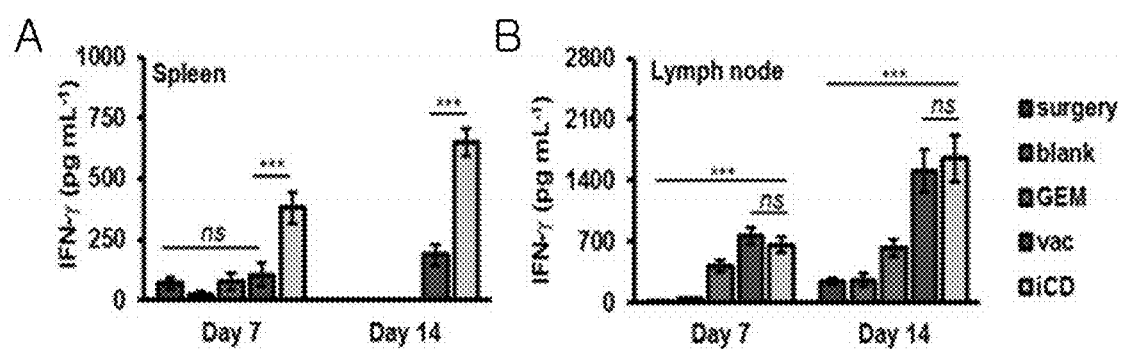
FIG. 39 is a set of graphs comparing concentrations of interferon gamma measured after cells are extracted from the spleen (A) and the lymph node (B) on day 7 and day 14 after tumor resection and implantation of a soft bio-integrated device, treated with a cancer vaccine and activated for 72 hours.

In addition, as a result of comparing interferon-gamma concentrations after cells were extracted from the spleen (FIG. 39A) and a lymph node (FIG. 39B) on day 7 and day 14 after the tumor resection and the implantation of a soft bio-integrated device, and treated with a lysate to activate the cells for 72 hours, it can be confirmed that, in an experimental group of a soft bio-integrated device containing all of gemcitabine, poly(I:C)-nanogel and a cell lysate, the interferon-gamma concentration most significantly increased.

Example 12

Figure 40:
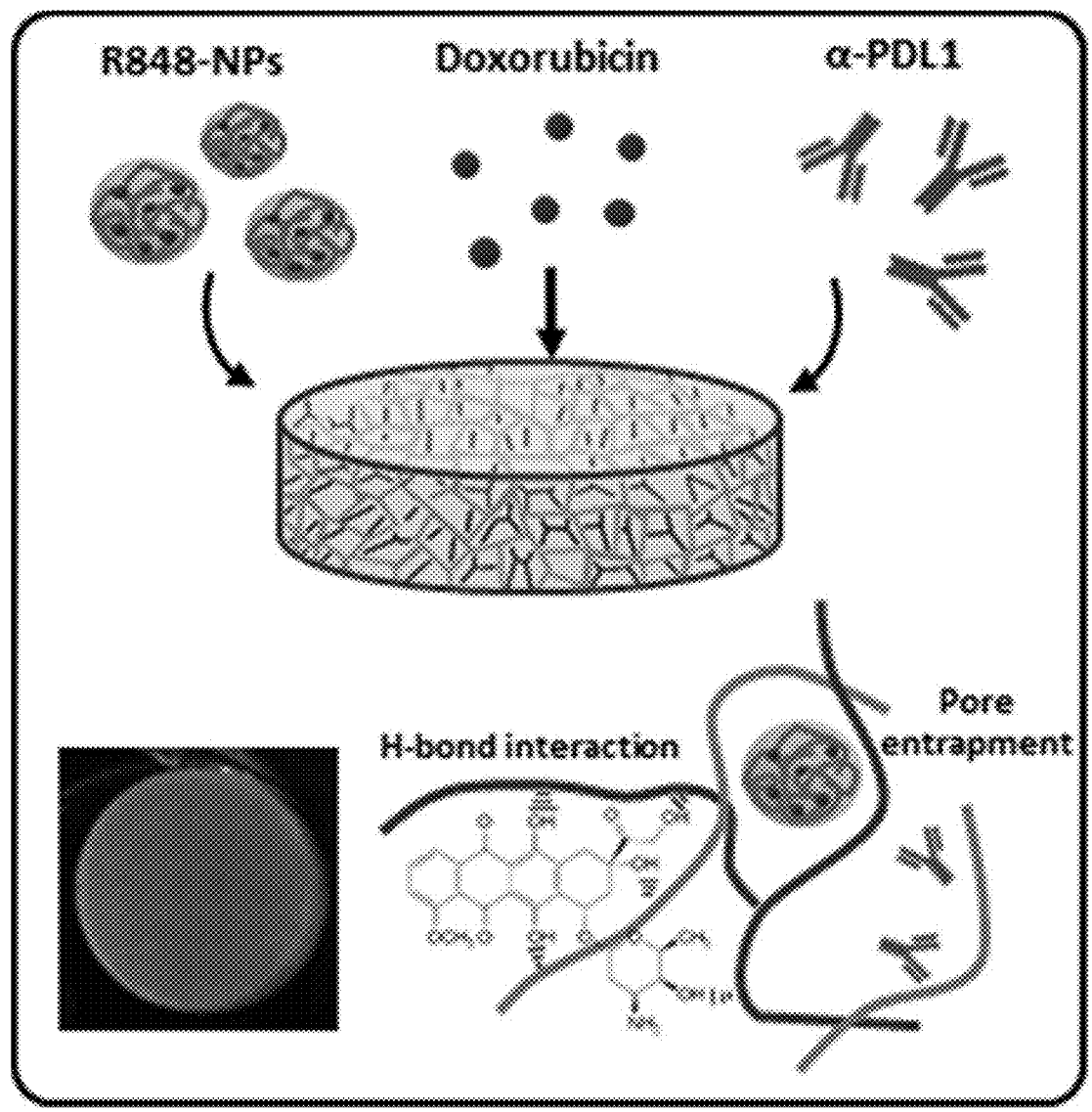
FIG. 40 illustrates a soft bio-integrated device in which an anticancer agent, a drug for regulating functions of immunosuppressive cells such as MDSCs and tumor-associated macrophages (TAMs), and a cancer immunosuppressive adjuvant are loaded.
Figure 41:
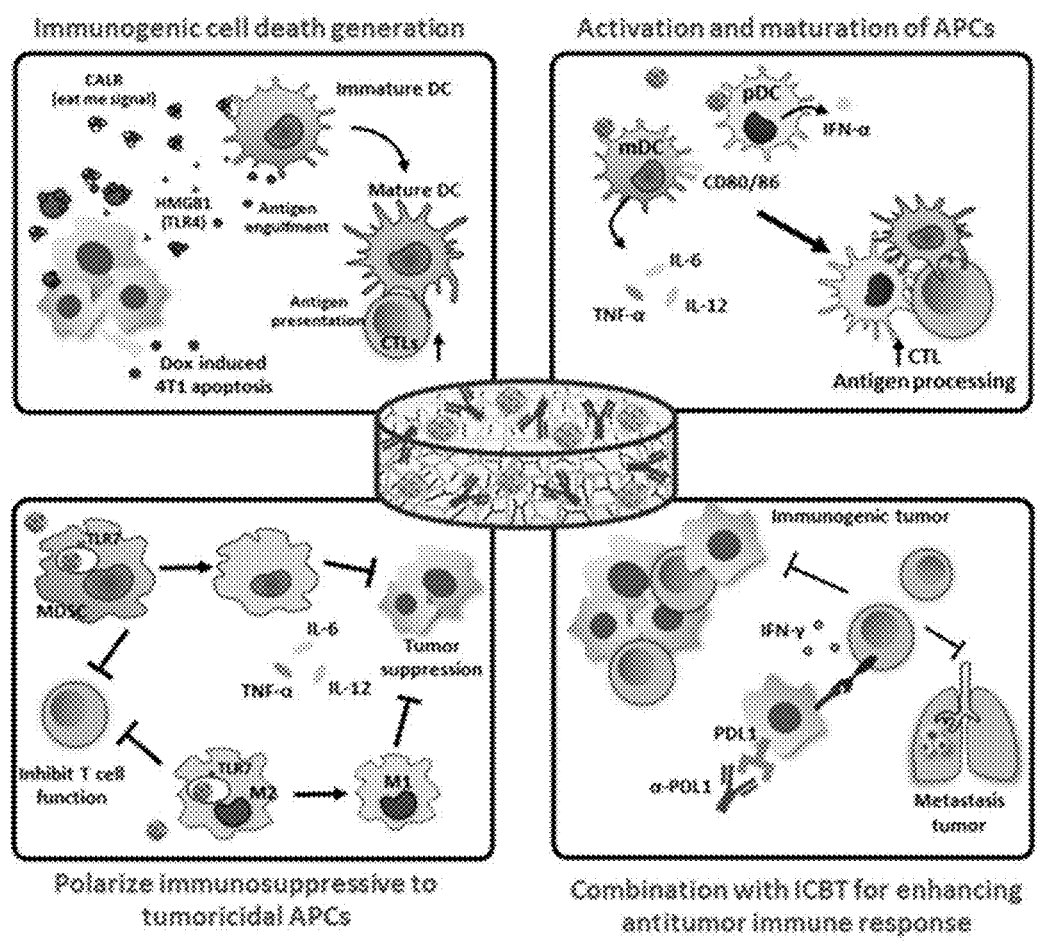
FIG. 41 illustrates immunogenic cell death caused by doxorubicin, the function of inducing the change of immunosuppressive cells, i.e., MDSCs, into antigen-presenting cells by resiquimod (R848) nanoparticles and controlling a TAM function (M2→M1 polarization), an immunosuppressive adjuvant function and the function of activating T cells by an immune checkpoint inhibitor, anti-PDL1.
Figure 42A:
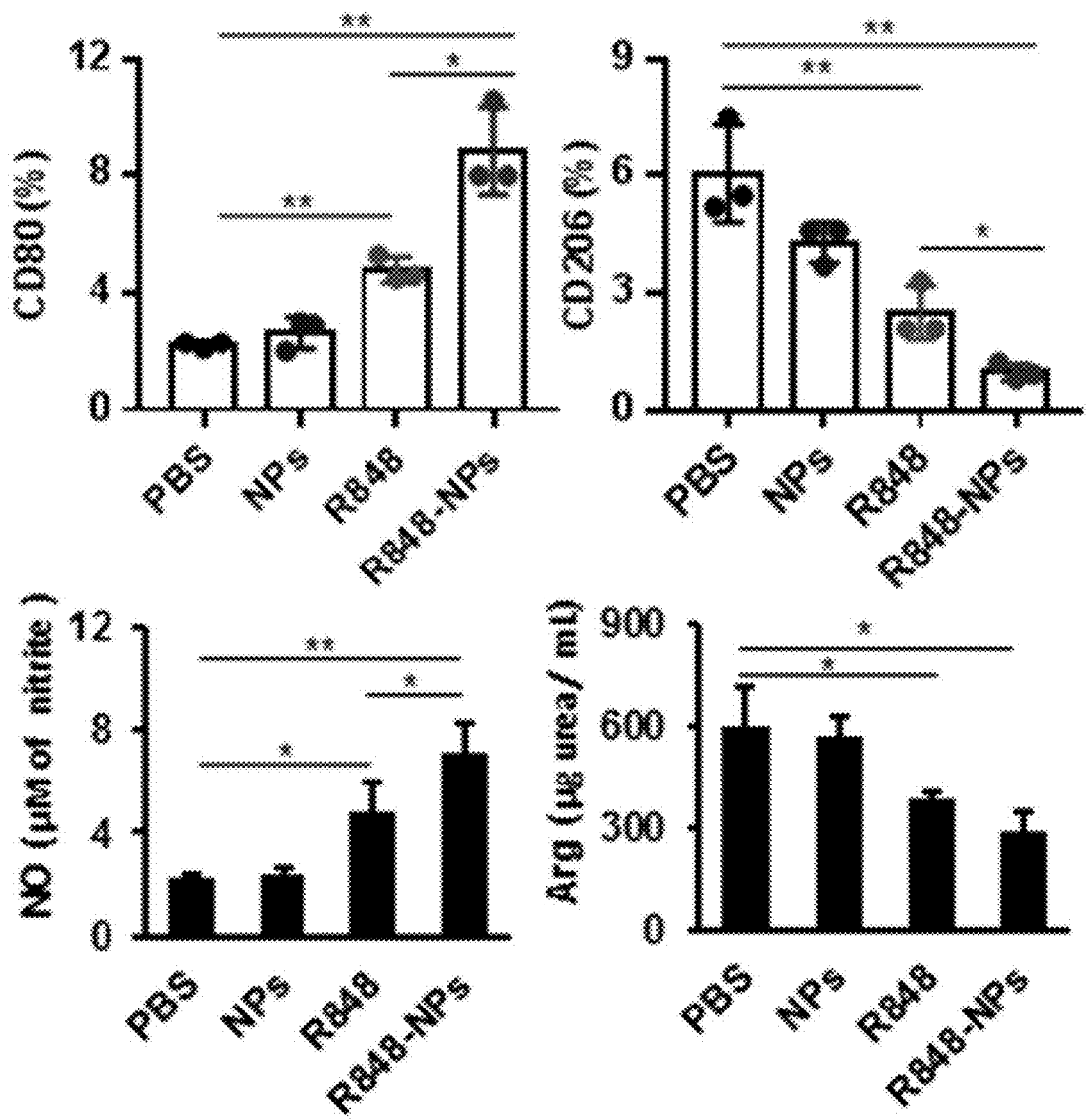
FIG. 42A shows the results of measuring surface markers (CD86/CD206) and an Arg/NO production rate to determine the tendency of M2 to M1 macrophage polarization in a resiquimod (R848)-treated group.
Figure 42B:
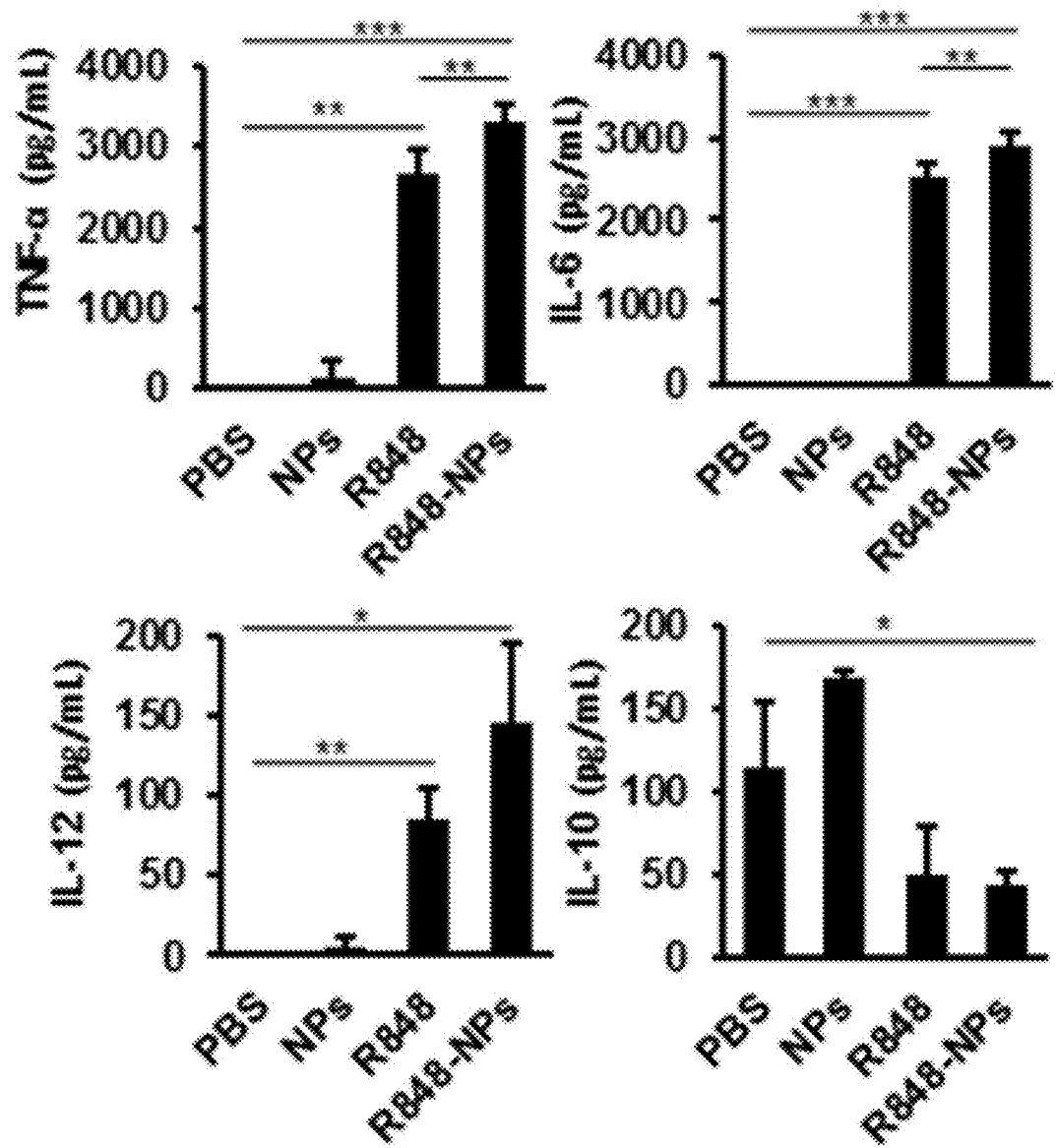
FIG. 42B shows the results of measuring the expression of cytokines.

Fabrication of Soft Bio-Integrated Device in Which Anticancer Agent, Drug for Regulating Functions of Immunosuppressive Cells Such as MDSCs and TAMs, Cancer Immunoactivating Adjuvant and Immune Checkpoint Inhibitor were Loaded and Evaluation of its Characteristics as Immune Anticancer Agent In the process of fabricating a hyaluronic acid/collagen scaffold in Example 2, a soft bio-integrated device including doxorubicin, which is an anticancer agent inducing immunogenic cell death, resiquimod (R848) nanoparticles, which have a multifunctional characteristics of controlling the functions of immunosuppressive cells such as MDSCs and TAMs and having an immune-enhancing adjuvant function as a TLR7 agonist, and anti-PDL1 as an immune checkpoint inhibitor in a mixed solution was fabricated (FIGS. 40 and 41). The characteristics of the fabricated soft bio-integrated device as an immune anticancer agent were evaluated by the methods described in Examples 9 and 11. As seen from FIGS. 42A and 42B, in a resiquimod-treated group, the tendency of macrophage polarization from M2 to M1 was able to be observed by measuring levels of surface markers (CD86/CD206) and Arg/NO generation (FIG. 42A) and cytokine expression levels (FIG. 42B). It can be observed that the level of an inflammatory cytokine associated with immune activation increased whereas the level of a cytokine associated with immunosuppression such as IL-10 decreased. In addition, it can be seen that, compared with pure resiquimod, M1 polarization caused by resiquimod (R848-NPs) loaded into the nanoparticles was improved.

Figure 43:
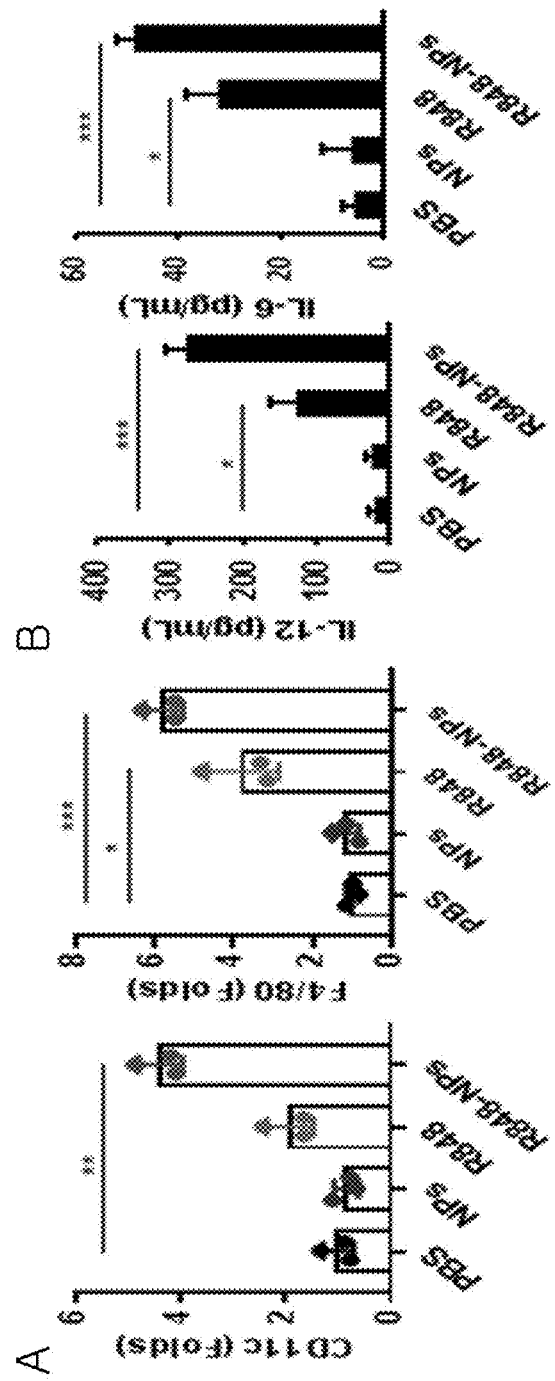
FIG. 43 shows the results measuring (a) the tendency of inducing a change of immune suppressor cells, MDSCs, into antigen-presenting cells such as dendritic cells and macrophages by resiquimod nanoparticles, and (b) expression variations of inflammatory cytokines by this change.
Figure 44:
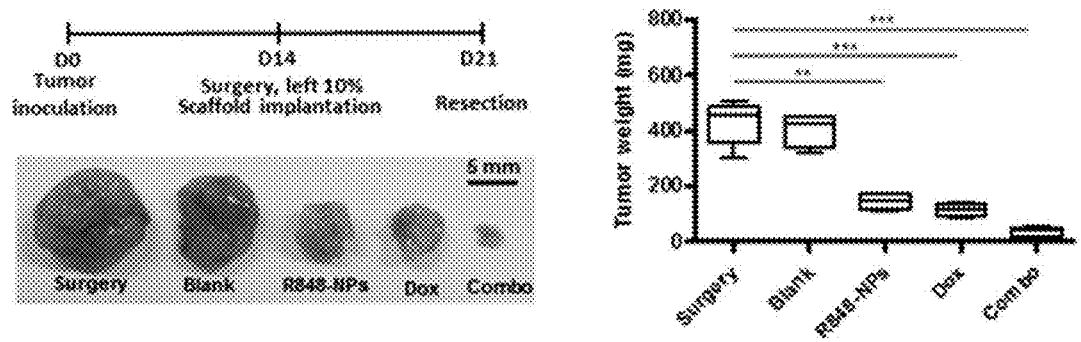
FIG. 44 shows the results of measuring weights of cancer tissues recurring after surgery to investigate anticancer effects in a group in which doxorubicin (Dox) or resiquimod (R848-NPs) is individually loaded into a soft bio-integrated device and a group (combo) in which a doxorubicin anticancer agent as well as resiquimod is further loaded into a soft bio-integrated device.
Figure 45:
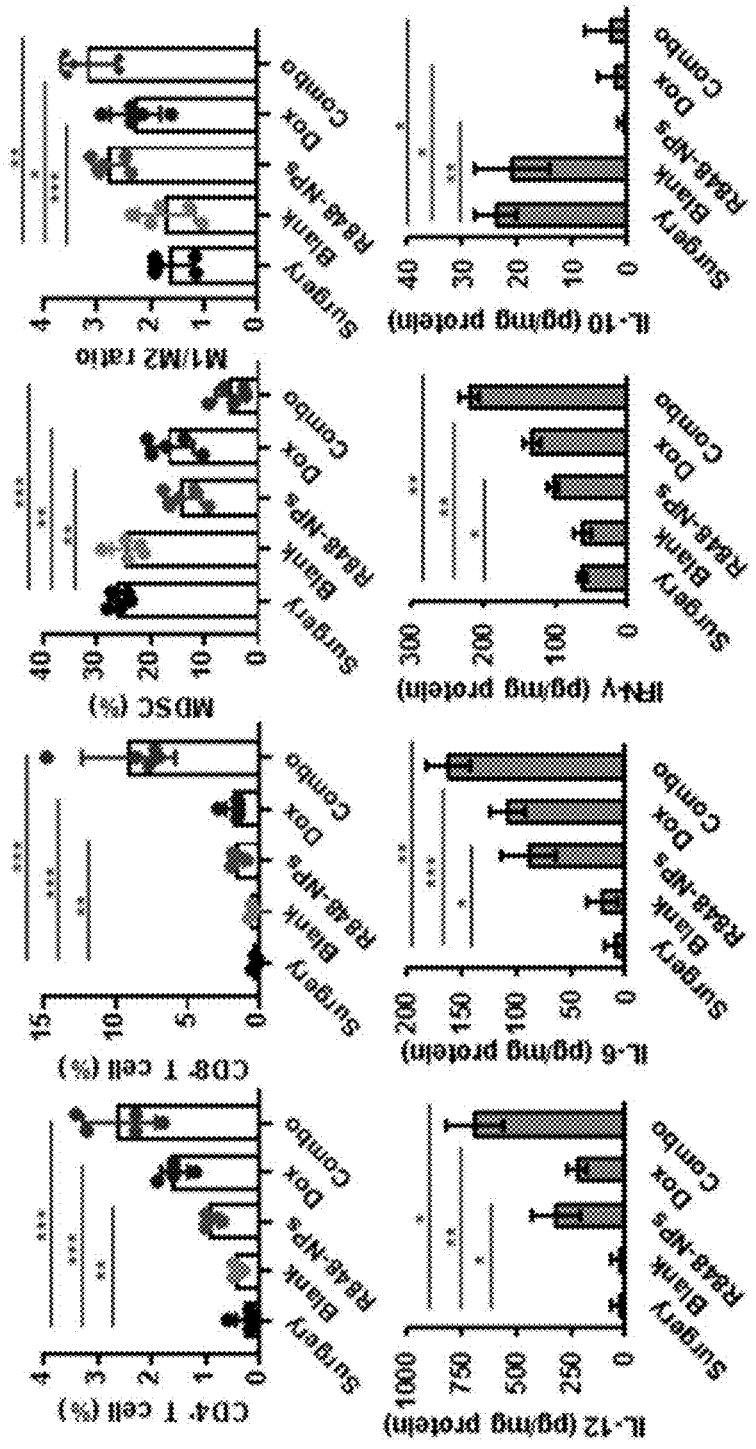
FIG. 45 shows the results of measuring the tendencies of increasing the numbers of T cells and M1 macrophages associated with cancer treatment and decreasing the numbers of MDSCs and M2 macrophages, which are immune suppressor cells due to the synergistic effect of doxorubicin and resiquimod, and variations of cytokines (IL-12, IL-6 and IFN-gamma) associated with an anticancer effect and cytokine (IL-10) associated with proliferation of cancer cells.
Figure 46:
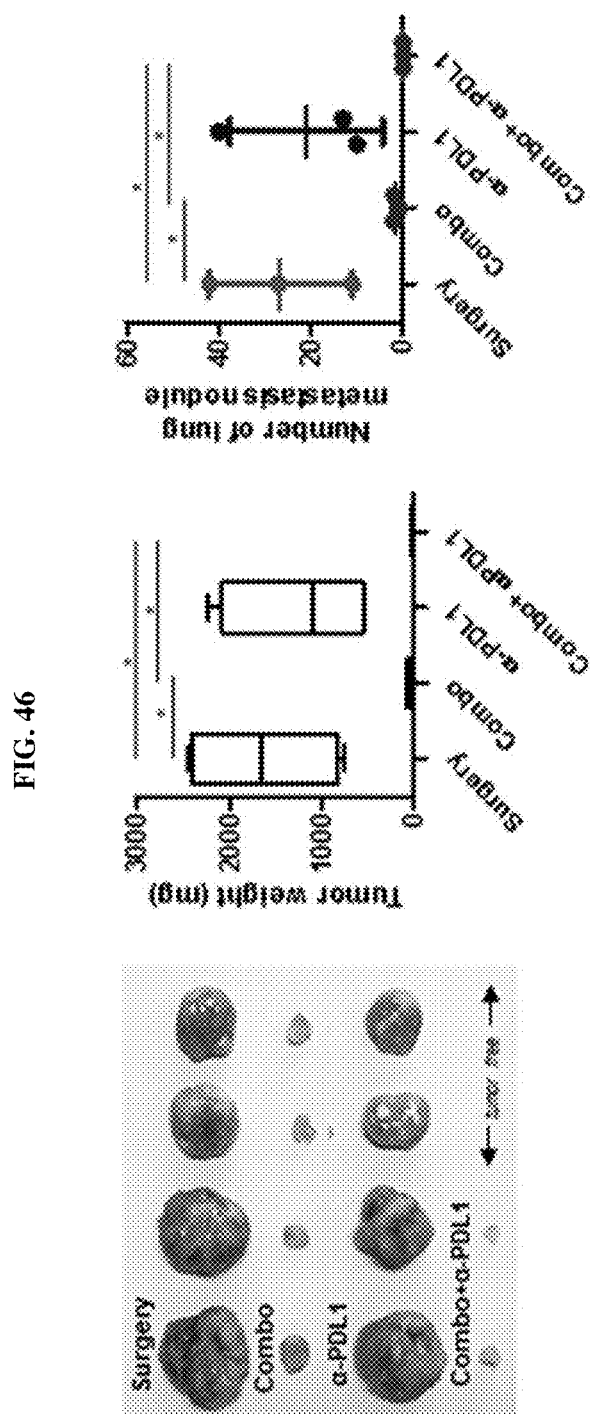
FIG. 46 shows the results of anticancer effects of a soft bio-integrated device (Combo) in which both of doxorubicin and resiquimod are loaded, a soft bio-integrated device (α-PDL1) in which only anti-PDL1 as an immune checkpoint inhibitor is loaded, and a soft bio-integrated device in which all of anti-PDL1, doxorubicin and resiquimod are loaded, respectively.
Figure 47:
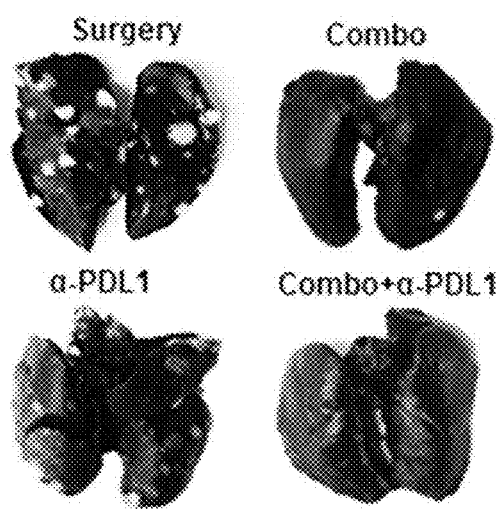
FIG. 47 shows the results of confirming lung metastasis of cancer cells in groups treated with a soft bio-integrated device (combo) in which both of doxorubicin and resiquimod are loaded, a soft bio-integrated device (α-PDL1) in which only anti-PDL1 as an immune checkpoint inhibitor is loaded, and a soft bio-integrated device in which all of anti-PDL1, doxorubicin and resiquimod are loaded, respectively.

In addition, it can be observed that induction of a change of immunosuppressive cells such as MDSCs into antigen-presenting cells such as dendritic cells and macrophages (FIG. 43A), caused by resiquimod nanoparticles, and the expression of inflammatory cytokines (FIG. 43B) caused by such a change were increased. It can be observed that, compared with the case in which doxorubicin or resiquimod is individually loaded, in a group (combo) in which a doxorubicin (Dox) anticancer agent is additionally loaded in a soft bio-integrated device, the recurrence of cancer after surgery was dramatically inhibited (FIG. 44). The above-described excellent anticancer effect can be inferred by increases in the numbers of T cells and M1 macrophages, associated with cancer treatment, and decreases in the numbers of immunosuppressive cells such as MDSCs and M2 macrophages due to a synergistic effect between doxorubicin and resiquimod (FIG. 45). It can be confirmed that, due to the increases in immunoactivating cells and the decreases in immunosuppressive cells, cytokines (IL-12, IL-6 and IFN-gamma) associated with an anticancer effect increased whereas a cytokine (IL-10) level, associated with the proliferation of cancer cells, decreased (FIG. 45). To verify a synergistic effect with an immune checkpoint inhibitor such as anti-PDL1, an anticancer effect was verified after anti-PDL1 was additionally loaded in a combo group in which both of doxorubicin and resiquimod appeared in the group in which anti-PDL1 was additionally loaded, and as seen from FIG. 46, in the group loaded with anti-PDL1 additionally, tumor-free mice were identified. And as seen from FIG. 47, it was confirmed that lung metastasis was also dramatically inhibited. These experimental results show that, in a tumor model having a slight effect of an immune checkpoint inhibitor such as anti-PDL1, a synergistic effect can be induced by a drug-loaded soft bio-integrated device.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

As a cryogel scaffold according to the present invention is fabricated at a low temperature by mixing two or more components with different degradabilities, it can have a degradability and/or a swelling ratio, which is (are) suitable for a use and a purpose by adjusting concentrations of the components and a mixing ratio of these components. Therefore, it is expected that the application of the cryogel scaffold will be expanded. In addition, it was confirmed that an effect of treating a solid tumor with a low therapeutic effect can be significantly improved by loading both of an anticancer agent and a drug for controlling an immunosuppressive action in the cryogel scaffold of the present invention, and thus it is expected that the cryogel scaffold of the present invention can be widely used in a variety of solid tumor treatments.

The invention claimed is:
1. A cryogel scaffold comprising a structure in which a first component and a second component are crosslinked,
wherein the first component is swollen when brought into contact with an aqueous solution, thereby increasing the volume of the scaffold, and the second component is a compound different from the first component, is crosslinkable with the first component and enables the control of degradability by an external stimulus after being crosslinked with the first component, and
wherein the first component is hyaluronic acid-methacrylate and the second component is hyaluronic acid-aldehyde methacrylate; or
wherein the first component is poly(gamma-glutamic acid)) and the second component is collagen.
2. The cryogel scaffold of claim 1, wherein the first component and the second component are contained at 10:90 to 90:10, 20:80 to 80:20, 30:70 to 70:30, 40:60 to 60:40, or 50:50 w/v %.
3. The cryogel scaffold of claim 1, wherein the structure in which the first component and the second component are crosslinked is formed at −25° C. to −4° C.
4. The cryogel scaffold of claim 1, wherein the external stimulus is one or more stimuli selected from the group consisting of a physiological condition in the body, light, a reductant and an enzyme.
5. A soft bio-integrated device comprising:
a cryogel scaffold comprising a structure in which a first component and a second component are crosslinked; and a drug, wherein the first component is swollen when brought into contact with an aqueous solution, thereby increasing the volume of the scaffold, wherein the second component is a compound different from the first component, is crosslinkable with the first component and enables the control of degradability by an external stimulus after being crosslinked with the first component, and wherein the drug is a drug for controlling an immunosuppressive action in a solid tumor microenvironment, and wherein the first component is hyaluronic acid-methacrylate and the second component is hyaluronic acid-aldehyde methacrylate; or wherein the first component is poly(gamma-glutamic acid)) and the second component is collagen.

6. The soft bio-integrated device of claim 5, wherein the drug suppresses the activity, survival or proliferation of myeloid-derived suppressor cells (MDSCs), regulatory T cells (Tregs), and/or tumor-associated macrophages (TAMs).

7. The soft bio-integrated device of claim 5, wherein the soft bio-integrated device further comprises one or more drugs selected from the group consisting of an anticancer agent, an immunosuppressive factor-controlling drug, a cancer vaccine, an immunoadjuvant, immune cells for cancer therapy, a drug for suppressing an immune checkpoint, an immune cell-activating cofactor, an antibody for cancer therapy, and a cytokine required for maintaining the activity of the immune cells for cancer therapy.

8. The soft bio-integrated device of claim 5, wherein the structure in which the first component and the second component are crosslinked is formed at −25 to −4° C.

9. The soft bio-integrated device of claim 5, wherein the soft bio-integrated device further comprises arginylglycylaspartic acid (RGD peptide) or an extracellular material (ECM)-derived material.

* * * * *